United States Patent
Chae et al.

(10) Patent No.: US 10,792,371 B2
(45) Date of Patent: *Oct. 6, 2020

(54) C-MET TARGETING COMPOUND-BIOACTIVE MATERIAL CONJUGATE AND USE THEREOF

(71) Applicant: Samsung Electronics Co., Ltd., Suwon-si, Gyeonggi-do (KR)

(72) Inventors: Su Young Chae, Suwon-si (KR); Sunghyun Kim, Hwaseong-si (KR); Eun Ko, Anyang-si (KR); Yun Ju Jeong, Hwaseong-si (KR); Jae Hyun Choi, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 290 days.

This patent is subject to a terminal disclaimer.

(21) Appl. No.: 15/884,963

(22) Filed: Jan. 31, 2018

(65) Prior Publication Data

US 2018/0236097 A1    Aug. 23, 2018

Related U.S. Application Data

(62) Division of application No. 14/485,062, filed on Sep. 12, 2014, now Pat. No. 9,889,206.

(30) Foreign Application Priority Data

Sep. 12, 2013 (KR) ........................ 10-2013-0109889

(51) Int. Cl.
    *C07K 16/00*       (2006.01)
    *A61K 39/00*       (2006.01)
    *A61K 47/68*       (2017.01)

(52) U.S. Cl.
    CPC ...... *A61K 47/6859* (2017.08); *A61K 47/6803* (2017.08); *A61K 47/6851* (2017.08)

(58) Field of Classification Search
None
See application file for complete search history.

(56) References Cited

U.S. PATENT DOCUMENTS

| | | | |
|---|---|---|---|
| 5,869,045 | A | 2/1999 | Hellstrom et al. |
| 8,501,917 | B2 | 8/2013 | Kim et al. |
| 9,745,376 | B2 | 8/2017 | Violette et al. |
| 2009/0175860 | A1 | 7/2009 | Stover et al. |
| 2011/0104176 | A1 | 5/2011 | Cheong et al. |
| 2013/0089542 | A1 | 4/2013 | Lee et al. |
| 2013/0315895 | A1 | 11/2013 | Farrell et al. |
| 2014/0154251 | A1 | 6/2014 | Lee et al. |
| 2014/0193431 | A1 | 7/2014 | Park et al. |

FOREIGN PATENT DOCUMENTS

| | | |
|---|---|---|
| EP | 2 143 441 A1 | 1/2010 |
| KR | 10-2008-0031049 A | 7/2009 |
| KR | 1020120134938 A | 12/2012 |
| KR | 1020130037153 A | 4/2013 |
| KR | 1020130054745 A | 5/2013 |
| KR | 1020130059114 A | 6/2013 |
| WO | WO 2003/100033 | 4/2003 |
| WO | WO 2007/008712 | 1/2007 |
| WO | WO 2012/003338 A1 | 1/2012 |

OTHER PUBLICATIONS

Bendig, "Humanization of Rodent Monoclonal Antibodies by CDR Grafting", Methods: A Companion to Methods in Enzymology, 8:83-93 (1995).
Byers, "What Can Randomized Controlled Trials Tell Us About Nutrition and Cancer Prevention?", CA Cancer J Clin, 49: 353-361 (1999).
Colman, "Effects of amino acid sequence changes on antibody-antigen interactions", Research in Immunology, 145: 33-36 (1994).
Granziero et al., "Adoptive immunotherapy prevents prostate cancer in a transgenic animal model", Eur., J. Immunol., 29: 1127-1138 (1999).
Kinoshita et al., "PSK enhances the efficacy of docetaxel in human gastric cancer cells through inhibition of nuclear factor-kB activation and surviving expression", International Journal of Oncology, 36:593-600 (2010).
Lee et al., "Cbl-independent degradation of Met: ways to avoid agonism of bivalent Met-targeting antibody", Oncogene, pp. 1-10 (2012).
Lu et al., "Single chain anti-c-Met antibody conjugated nanoparticles for in vivo tumor-targeted imaging and drug delivery", Biomaterials, 32: 3265-3274 (2011).
Paul, Fundamental Immunology, 3$^{rd}$ Edition, pp. 292-295 (1993).
Rudikoff et al., "Single amino acid substitution altering antigen-binding specificity", Proc. Natl. Acad. Sci. USA, 79: 1979-1983 (1982).
Office Action issued in Korean Patent Application No. 10-2013-0109889 dated Jan. 8, 2020.

*Primary Examiner* — Mark Halvorson
(74) *Attorney, Agent, or Firm* — Leydig, Voit & Mayer, Ltd.

(57) ABSTRACT

Provided is a conjugate including a c-Met targeting compound and a bioactive material and methods of use of the conjugate.

16 Claims, 14 Drawing Sheets
(1 of 14 Drawing Sheet(s) Filed in Color)

Specification includes a Sequence Listing.

C-MET TARGETING COMPOUND-BIOACTIVE MATERIAL CONJUGATE AND USE THEREOF

CROSS-REFERENCE TO RELATED APPLICATIONS

This application is a divisional of copending U.S. patent application Ser. No. 14/485,062 filed on Sep. 12, 2014, which in turn claims the benefit of Korean Patent Application No. 10-2013-0109889 filed on Sep. 12, 2013, in the Korean Intellectual Property Office, the entire disclosures of which are hereby incorporated by reference.

INCORPORATION BY REFERENCE OF ELECTRONICALLY SUBMITTED MATERIALS

Incorporated by reference in its entirety herein is a computer-readable nucleotide/amino acid sequence listing submitted herewith and identified as follows: One 135,571 byte ASCII (Text) file named "736582_ST25.TXT" created Jan. 24, 2018.

BACKGROUND

1. Field

Provided is a conjugate including a c-Met targeting compound and a bioactive material and methods of use of the conjugate.

2. Description of the Related Art c-Met is a hepatocyte growth factor (HGF) receptor, encoded by the oncogene c-met, functioning to mediate a wide spectrum of signals driven by its ligand HGF which binds to an extracellular domain of the c-Met receptor tyrosine kinase to induce the promotion of division, motility, morphogenesis and angiogenesis in various normal and cancer cells. In some cases, c-Met is involved, irrespective of its ligand HGF, in a variety of tumorigenesis including oncogenesis, metastasis, cancer cell migration, cancer cell invasion, and angiogenesis, therefore attracting a keen interest as a target protein for cancer therapy.

Particularly, c-Met is recognized as being of significance for personalized therapy as it is known to play a role in drug resistance with regard to the activity of conventional anti-cancer agents. Erbitux and Tarceva, both representative anticancer agents which target EGFR (ERBB1), perform their functions by blocking oncogenic mechanism-related signal transduction. Herceptin, a typical therapeutic for breast cancer, functions to block a signal pathway necessary for cell growth, targeting ERBB2 (HER2). However, recent studies on patients with resistance to the drugs reported that other signaling pathways responsible for cell growth are activated by detouring the action of the anticancer agents through the overexpression of c-Met. For this reason, c-Met is a target molecule to which many pharmaceutical companies pay keen attention, attempting to develop various drugs, for example, antibodies, which are designed to bind to c-Met to inhibit HGF signaling.

These c-Met targeting drugs are known to exhibit anticancer efficiency in various c-Met positive cancers. On the contrary, some c-Met targeting drugs (for example, antibodies) are observed to act as an agonist causative of the side effect (agonism) that they combine by themselves to induce the dimerization of c-Met, irrespective of the ligand, thereby initiating oncogenic signaling. In addition, another problem is the impotence of c-Met targeting drugs (for example, antibodies) in cancer cells which express the antigen c-Met at a low level. An antibody-drug conjugate (ADC) was also developed in which an antibody is conjugated with a drug was developed to synergize the targeting of the drug, but is disadvantageously ineffective in internalization.

SUMMARY

Provided is a conjugate including a c-Met targeting compound and a bioactive material, in which the c-Met targeting compound and the bioactive material are conjugated with each other.

Another embodiment provides a conjugate including an anti-c-Met antibody and a cytotoxic agent, in which the anti-c-Met antibody and the cytotoxic agent are conjugated with each other.

Another embodiment provides a pharmaceutical composition including the conjugate.

Another embodiment provides a composition useful for the prevention and/or treatment of a cancer, including the conjugate as an active ingredient.

Another embodiment provides a method for preventing and/or treating a cancer including administering the conjugate to a subject in need thereof.

Another embodiment provides a method for preparing an anti-c-Met antibody derivative having improved efficacy, including conjugating an anti-c-Met antibody with a cytotoxic agent.

Another embodiment provides a method for improving the efficacy of an anti-c-Met antibody, including conjugating the anti-c-Met antibody with a cytotoxic agent.

Another embodiment provides a method for preparing a cytotoxic agent derivative having improved internalization efficiency, including conjugating a cytotoxic agent with an anti-c-Met antibody.

Another embodiment provides a method for improving the internalization efficiency of a cytotoxic agent, including conjugating the cytotoxic agent with an anti-c-Met antibody.

Another embodiment provides a composition for the intracellular delivery of a bioactive material, including an anti-c-Met antibody.

Still another embodiment provides a method for intracellular delivery of a bioactive material, using an anti-c-Met antibody.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

One embodiment provides a conjugate including a c-Met targeting compound and a bioactive material, wherein the c-Met targeting compound and the bioactive material are conjugated with each other.

In an embodiment, the c-Met targeting compound may be an anti-c-Met antibody. The bioactive material may be selected from the group consisting of a cytotoxic agent, a radio-isotope, a contrast agent, and a combination thereof.

Another embodiment provides an antibody-drug conjugate (ADC) in which an anti-c-Met antibody and a cytotoxic agent are conjugated with each other.

In the antibody-drug conjugate, the anti-c-Met antibody and the cytotoxic agent may be conjugated by a chemical bond, e.g., a covalent bond. For example, the anti-c-Met antibody may be linked to the cytotoxic agent by thiol coupling (SH coupling) or amine coupling ($NH_2$ coupling). To this end, the drug may be derivatized with (further comprise) a functional group which allows for SH coupling or $NH_2$ coupling.

The functional group may be introduced into the drug directly or via a linker. The linker is sufficiently blood stream stable to prevent the drug from segregating from the antibody during the blood circulation of the conjugate in the body so that the drug can remain in a prodrug form until encountering the target, thereby not only producing minimal damage on normal tissues, but also allowing for the cytotoxic agent to be specifically dissociated from the prodrug in cancer cells or tissues thereby exhibiting cytotoxic activity. So long as it exhibits these functions, any linker can be used.

In an embodiment, the cytotoxic agent may be a derivative into which a functional group capable of thiol (SH) coupling or amine ($NH_2$) coupling is introduced directly or via a linker.

Figure 1:
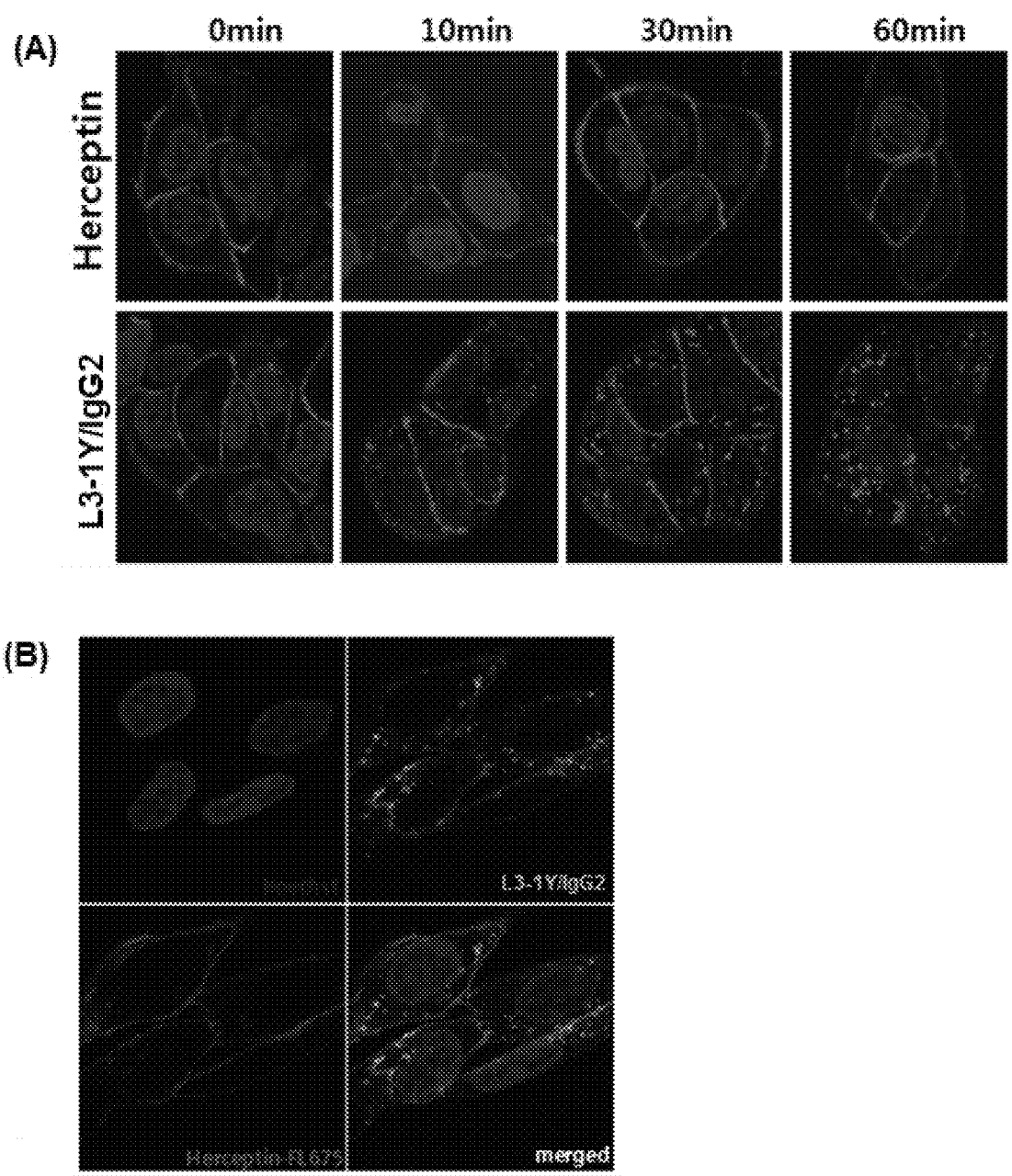
FIG. 1 is a series of fluorescent images showing internalization behaviors of an anti-c-Met antibody and Herceptin.

The anti-c-Met antibody specifically recognizes and binds to c-Met, followed by internalization into cells (see FIG. 1). Due to these characteristics, the anti-c-Met antibody can help a bioactive material conjugated thereto, such as a cytotoxic agent, a radio-isotope, and/or a contrast agent, enter target cells, improving the intracellular performance of action of the bioactive material, e.g., the cytotoxicity of the cytotoxic agent, the intended intracellular efficacy of the radio-isotope, or the contrasting efficiency of the contrast agent.

In addition, the antibody-drug conjugate produces at least additive and possibly synergistic effects of the antibody and the drug. When the bioactive material is a cytotoxic agent, the conjugate not only synergistically inhibits cancer cells against which the anti-c-Met antibody is active, but can also exert an anticancer effect on even cancer cells either for which the anti-c-Met antibody may cause a side effect (agonism) or on cancer cells resistant to the anti-c-Met antibody. Given the bioactive material, the anti-c-Met antibody can expand the spectrum of its applicability. On the other hand, when a cytotoxic agent (e.g., an anticancer agent) with the problem of, for example, hepatotoxicity, is applied as a conjugate with the anti-c-Met antibody, a significant reduction in hepatotoxicity is observed (see Example 6 and FIG. 12).

Another embodiment provides a pharmaceutical composition including the conjugate as an active ingredient.

A particular embodiment provides a pharmaceutical composition for the prevention and/or treatment of a cancer, including as an active ingredient an antibody-drug conjugate (ADC) in which an anti-c-Met antibody and a cytotoxic agent are conjugated with each other.

Still another embodiment provides a method for preventing and/or treating a cancer, including administering an antibody-drug conjugate in which an anti-c-Met antibody and a cytotoxic agent are conjugated with each other, to a subject in need of preventing and/or treating a cancer. The antibody-drug conjugate may be administered in amounts that are pharmaceutically effective, which amount may be determined by the skilled medical practitioner or medical researcher. The method may further include, prior to the administration step, a step of identifying a subject in need of preventing and/or treating a cancer. The step of identifying may be conducted by any manner and/or methods known to the relevant field for identifying whether or not a subject needs the prevention and/or treatment of cancer. For example, the step of identifying may include diagnosing a subject to have a cancer, or identifying a subject who is diagnosed as a cancer subject.

In this context, the subject is intended to encompass all animals that need the prophylaxis and/or therapy of cancer, whether urgently or potentially, and cells derived therefrom. For example, all mammals including primates such as humans and monkeys, and rodents such as mice and rats, cells or tissues derived (isolated) therefrom, and cultures of the cells or tissues may fall into the scope of the subject. For example, a patient with cancer, or cancer cells or tissues derived (isolated) from such patients, or a culture thereof may be a subject.

Taking advantage of the efficient internalization of an anti-c-Met antibody, another embodiment provides a pharmaceutical composition for the intracellular delivery of a cytotoxic agent, including an antibody-drug conjugate in which the anti-c-Met antibody and the cytotoxic agent are conjugated with each other. An additional embodiment provides a method for delivering a cytotoxic agent into a cell, including administering an antibody-drug conjugate in which an anti-c-Met antibody and the cytotoxic agent are conjugated with each other, to a subject in need of intracellular delivery of the cytotoxic agent. The delivery method may further include determining whether the subject is in need of the intracellular delivery of the cytotoxic agent before the administration.

In this context, the subject is intended to encompass all animals in need of the intracellular delivery of the cytotoxic agent, and cells or tissues derived (separated) therefrom. For example, all mammals including primates such as humans and monkeys, and rodents such as mice and rats, cells or tissues derived (isolated) therefrom, and cultures of the cells or tissues may fall into the scope of the subject. For example, a patient with cancer, or cancer cells or tissues derived (isolated) from the patients, or a culture thereof may be a subject.

As well as being effective in intracellular delivery, as elucidated herein, the antibody-drug conjugate is designed to detour problems attributed to the agonism of the anti-c-Met antibody and resistance to the drug, and to produce a significant reduction in hepatotoxicity, thereby exhibiting excellent anticancer activity against a broad spectrum of cancer cells.

Another embodiment provides a method for preparing an anti-c-Met antibody derivative (antibody-drug conjugate) by conjugating an anti-c-Met antibody with a cytotoxic agent. The conjugating step may comprise chemically (e.g., covalently) bonding an anti-c-Met antibody and a cytotoxic agent. The anti-c-Met antibody derivative may lead to not only a synergistic improvement in anticancer efficacy, but also a reduction in the side effect (agonism) of the anti-c-Met antibody and/or in resistance to the drug.

Another embodiment provides a method for potentiating (or improving) an anti-c-Met antibody, including conjugating the anti-c-Met antibody with a cytotoxic agent. The term "potentiating (or improving)" used in the context of the anti-c-Met antibody herein, is intended to pertain to increasing the anticancer activity of the anti-c-Met antibody in combination with the cytotoxic agent, and to reducing the side effect (agonism) of the anti-c-Met antibody and/or overcoming resistance to the drug.

Another embodiment provides a method for enhancing the intracellular delivery of a cytotoxic agent, including conjugating the cytotoxic agent to an anti-c-Met antibody, or a method for preparing a cytotoxic agent derivative (antibody-drug conjugate) with a high intracellular delivery potential.

The method for preparing an anti-c-Met antibody derivative, the method for potentiating an anti-c-Met antibody, and the method for enhancing the intracellular delivery of a cytotoxic agent may further include introducing a functional group capable of thiol coupling or amine coupling into an esterificable group, e.g., an OH group, of the cytotoxic agent, directly or via an intracellularly cleavable linker, prior to the conjugation of the cytotoxic agent to the anti-c-Met.

Any biocompatible substance that could perform a function in vivo may be used as the bioactive material. For example, it may be selected from the group consisting of various chemical drugs, peptides, proteins, and nucleic acids (DNA, RNA), and a combination thereof.

So long as it is cytotoxic, particularly, to cancer cells, any cytotoxic agent may be used. Various chemical drugs (e.g., anticancer agents), peptide drugs, protein drugs, and nucleic acids (e.g., antisense oligonucleotides, siRNA, shRNA, microRNA, aptamers, etc.) fall within the scope of the cytotoxic agent. Examples of the cytotoxic agent may be at least one selected from the group consisting of maytansine, auristatin based drugs, calicheamicin based drugs, pyrrolobenzodiazepine based drugs, duocarmycin, docetaxel, doxorubicin, carboplatin (paraplatin), cisplatin, cyclophosphamide, ifosfamide, nidran, nitrogen mustard, mechlorethamine HCl, bleomycin, mitomycin C, cytarabine, fluorouracil, gemcitabine, trimetrexate, methotrexate, etoposide, vinblastine, vinorelbine, alimta, altretamine, procarbazine, paclitaxel (Taxol), taxotere, topotecan, irinotecan, radioisotopes, and the like, but are not limited thereto.

The cytotoxic agent may be derivatized by introducing a functional group capable of forming a chemical bond (e.g., an ester linkage) with the antibody, for example, a functional group capable of thiol coupling, amine coupling or reductive amination (linking between amine and aldehyde) thereinto, either directly or via a linker which is cleavable within cells.

The functional group may be selected from the group consisting of, but not limited to, maleimide compounds, pyridyldithio compounds, N-hydroxysuccinimide compounds, derivatives thereof, aldehydes, and a combination thereof. So long as it can form a chemical bond with the anti-c-Met antibody (or an amino acid residue of the anti-c-Met antibody), any compound may be used as the functional group.

By way of example, the functional group capable of thiol coupling may be a compound which can react or form a bond with the thiol group of a cysteine residue of the anti-c-Met antibody. It may be selected from the group consisting of, but not limited to, maleimide compounds, pyridyldithio compounds, and a combination thereof. The functional group capable of amine coupling may be a compound that can form an amine bond with an amino acid residue, such as lysine, of the anti-c-Met antibody. It may be at least one selected from the group consisting of, but not limited to, N-hydroxysuccinimide compounds and derivatives thereof, and aldehydes. So long as it can form an amine bond with an amino acid residue such as a primary amine, lysine, and/or N-terminal amine from the anti-c-Met antibody, any compound may be used. For example, it may be an aldehyde, but is not limited thereto.

The functional group may be introduced (grafted) to the drug either via a suitable linker or directly. As well as being sufficiently stable to blood stream to prevent the segregation of the drug from the antibody during the blood circulation of the conjugate in the body so as for the drug to remain in remain in a prodrug form until encounter with the target, thereby producing possibly minimal damage on normal tissues, the linker should be cleaved in an acidic condition such as in cancer cells or cancer tissues or by a peptidase or protease in cancer cells or cancer tissues to release the cytotoxic agent to exhibit cytotoxicity after internalization into the cancer cells or cancer tissues. For example, the linker may be selected from the group consisting of, but not limited to, an amino acid, an amino acid derivative, a peptide (for example, available as a substrate of protease or peptidase) containing 1 to about 10 amino acids (for example, 2 to about 10 amino acids), an alkyl of C1 to C12, a hydrophilic spacer containing 1 to about 12 ethylene glycol units ($-CH_2CH_2-O-$), and a combination thereof with a linkage therebetween. For example, when the linkage between the antibody and the drug is a thiol coupling, the linker may be selected from the group consisting of, but not limited to, an amino acid, a peptide (for example, available as a substrate of protease or peptidase) containing 1 to about 10 amino acids (for example, 2 to about 10 amino acids), an alkyl of C1 to C12, and a combination thereof with a linkage therebetween. For amine coupling, the linker may be, but not limited to, a hydrophilic spacer containing 1 to about 12 ethylene glycol units ($-CH_2CH_2-O-$). A reductive amination-based linker between the antibody and the drug may be selected from the group consisting of, but not limited to, an amino acid, an amino acid derivative, a peptide (for example, available as a substrate of protease or peptidase) containing 1 to about 10 amino acids (for example, 2 to about 10 amino acids), a hydrophilic spacer containing 1 to about 12 ethylene glycol units ($-CH_2CH_2-O-$), and a combination thereof with a linkage therebetween.

As for the amino acid derivative, it may be in various forms such as neurotransmitters, hormones, metabolic intermediates, etc. Examples of the amino acid derivatives include GABA (Gamma-Amino Butyric Acid), serotonin, melatonin, thyroxine, indole acetate, citrulline, omitine, a carboxy-substituted amino acid (e.g., carboxylglutamate, etc.), a hydroxyl-substituted amino acid (e.g., hydroxyproline, hydroxylysine, allo-hydroxylysine, etc.), a phospho-substituted amino acid (e.g., phosphoserine, etc.), a C1~C4 alkyl-substitued amino acid (e.g., ethylglycine, ethylasparagine, methylglycine, methylisoleucine, methyllysine, methylvaline, etc.), aminoadipic acid, aminopropionic acid, aminobutyric acid, aminocapronic acid, aminoheptanic acid, aminoisobutyric acid, aminopimelic acid, diaminobutyric acid, desmosine, isodesmosine, diaminopimelic acid, diaminopropionic acid, norvaline, norleucine, alloisoleucine, and a combination thereof, but are not limited thereto.

In one embodiment, a docetaxel derivative (III) capable of amine coupling with an antibody may be prepared through derivatization as illustrated in the following Reaction Scheme 1 (see upper panel of FIG. 2):

[Reaction Scheme 1]

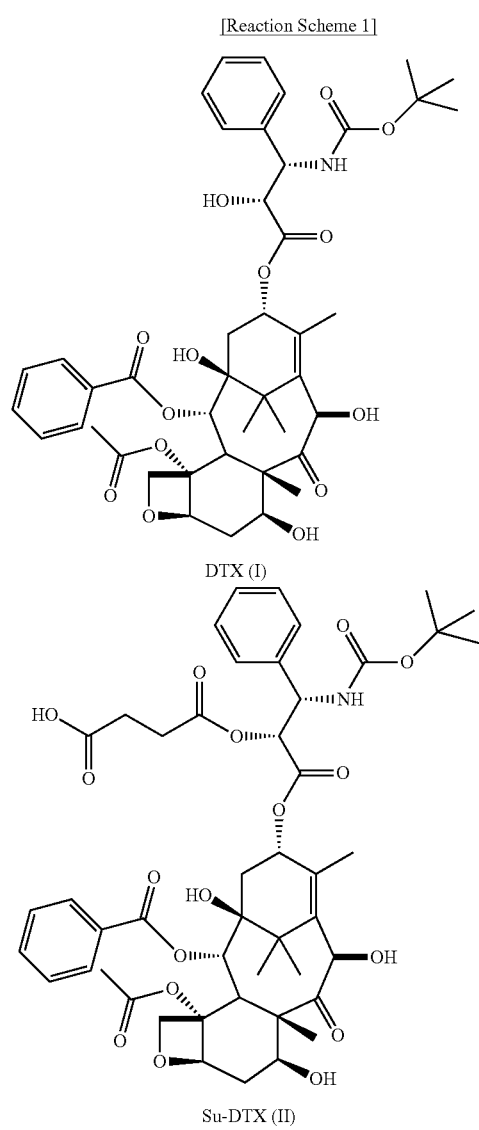

In another embodiment, the derivatization of docetaxel for thio coupling is carried out as illustrated in the following Reaction Scheme 2 to give a docetaxel derivative (VI) capable of thiol coupling with an antibody (see lower panel of FIG. 2):

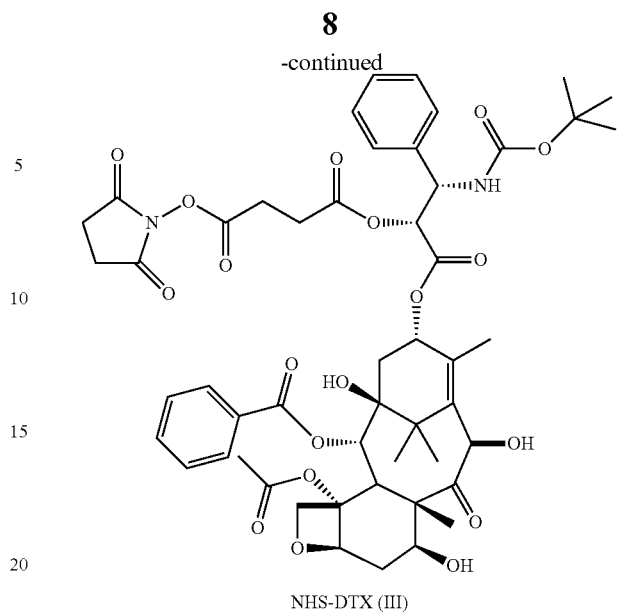

[Reaction Scheme 2]

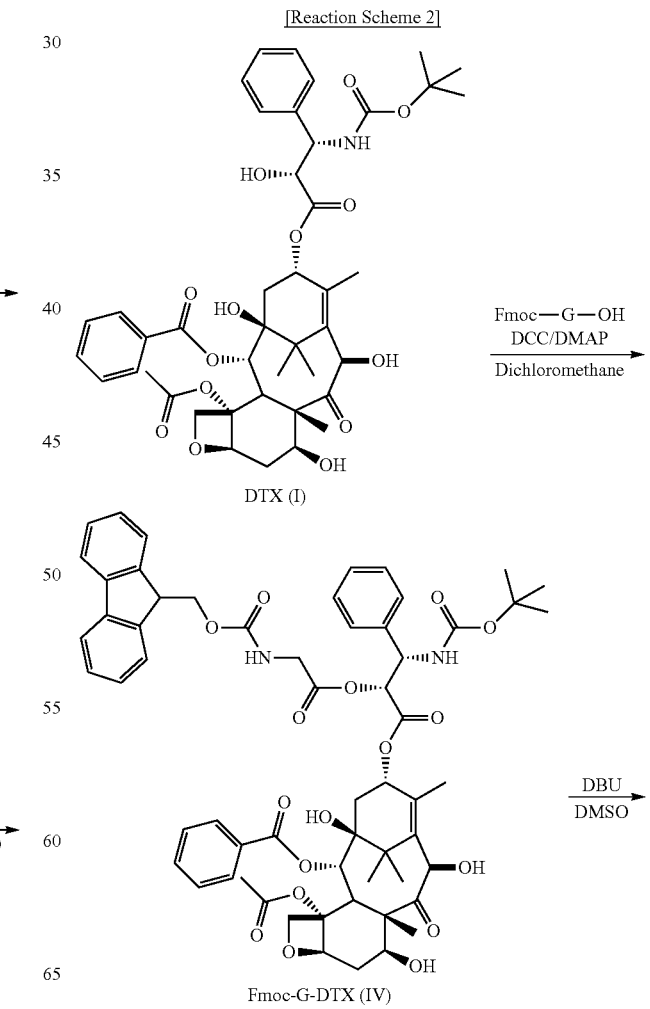

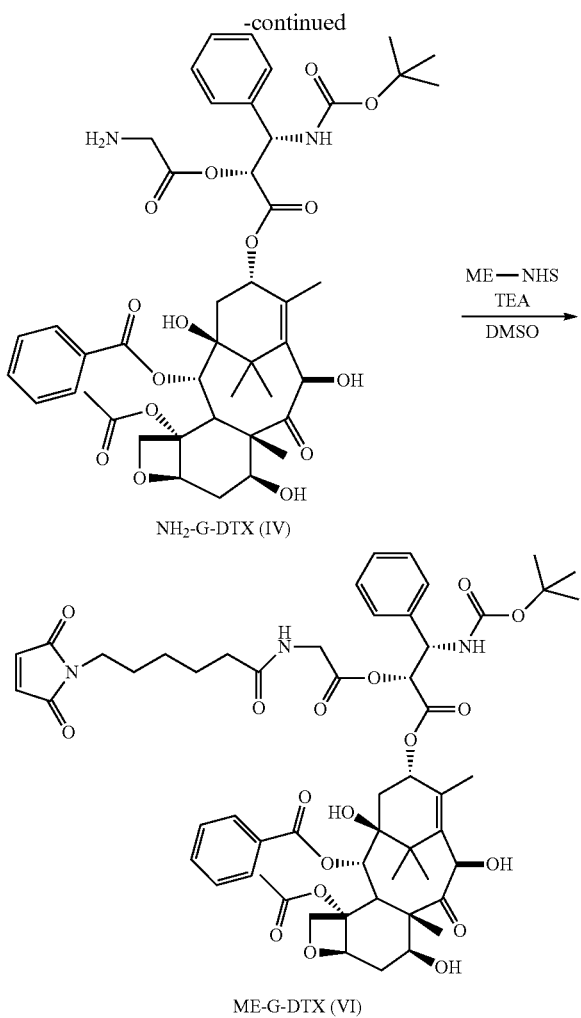

NH₂-G-DTX (IV)

ME-G-DTX (VI)

In a particular embodiment, the anti-c-Met antibody or an antigen binding fragment thereof may be any type of antibody capable of specifically recognizing and/or binding to c-Met, or an antigen-binding fragment thereof. The antigen-binding fragment of the anti-c-Met antibody may be selected from the group consisting of a complementarity determining region (CDR), fragment including CDR and Fc region, scFv, (scFv)₂, Fab, Fab', and F(ab')₂ of the anti-c-Met antibody. The anti-c-Met antibody may also include a variant of the antibody. The variant of the antibody may be any isotype of antibodies derived from human and other animals and/or one including any Fc region of antibodies derived from human and other animals, having a mutated hinge wherein at least one amino acid is changed, deleted or added. Unless stated otherwise, the anti-c-Met antibody may include the variants of the antibody as well as the antibody with no variation. In a particular embodiment, the anti-c-Met antibody may recognize a specific region of c-Met, e.g., a specific region in the SEMA domain, as an epitope. It may be any antibody or antigen-binding fragment that acts on c-Met to induce c-Met intracellular internalization and degradation.

The "c-Met" or "c-Met proteins" refer to receptor tyrosine kinases that bind to hepatocyte growth factors (HGF). The c-Met proteins may be those derived from all kinds of species, particularly a mammal, for example, those derived from a primate such as human c-Met (e.g. NP_000236), monkey c-Met (e.g., *Macaca mulatta*, NP_001162100), and the like, or those derived from a rodent such as mouse c-Met (e.g., NP_032617.2), rat c-Met (e.g., NP_113705.1), and the like. These proteins may include, for example, polypeptides encoded by the nucleotide sequence identified as GenBank Accession Number NM_000245, or proteins encoded by the polypeptide sequence identified as GenBank Accession Number NM 000236, or extracellular domains thereof. The receptor tyrosine kinase c-Met is involved in several mechanisms including cancer incidence, cancer metastasis, cancer cell migration, cancer cell penetration, angiogenesis, etc.

c-Met, a receptor for hepatocyte growth factor, may be divided into three portions: extracellular, transmembrane, and intracellular. The extracellular portion is composed of an α-subunit and a β-subunit which are linked to each other through a disulfide bond, and contains a SEMA domain responsible for binding HGF, a PSI domain (plexin-semaphorins-integrin homology domain) and an IPT domain (immunoglobulin-like fold shared by plexins and transcriptional factors domain). The SEMA domain of c-Met protein may have the amino acid sequence of SEQ ID NO: 79, and is an extracellular domain that functions to bind HGF. A specific region of the SEMA domain, that is, a region including the amino acid sequence of SEQ ID NO: 71, which corresponds to amino acids 106 to 124 of the SEMA domain (SEQ ID NO: 79), is a loop region between the second and the third propellers within the epitopes of the SEMA domain. It may act as an epitope for the anti-c-Met antibody.

The term "epitope," as used herein, refers to an antigenic determinant, a part of an antigen recognized by an antibody. In one embodiment, the epitope may be a region including 5 or more consecutive or non-consecutive amino acid residues within the SEMA domain (SEQ ID NO: 79) of c-Met protein, for instance, 5 to 19 consecutive or non-consecutive amino acid residues within the amino acid sequence of SEQ ID NO: 71 which corresponds to a range from amino acids. 106 to 124 within the SEMA domain (SEQ ID NO: 79) of a c-Met protein. For example, the epitope may be a polypeptide having 5 to 19 consecutive amino acids of the amino acid sequence of SEQ ID NO: 71, which sequence includes the amino acid sub-sequence EEPSQ (SEQ ID NO: 73) that serves as an essential element for the epitope. For example, the epitope may be a polypeptide comprising, consisting essentially of, or consisting of the amino acid sequence of SEQ ID NO: 71, SEQ ID NO: 72, or SEQ ID NO: 73.

The epitope including the amino acid sequence of SEQ ID NO: 72 corresponds to the outermost part of the loop between the second and third propellers within the SEMA domain of a c-Met protein, and the epitope including the amino acid sequence of SEQ ID NO: 73 is a site to which the antibody or an antigen-binding fragment most specifically binds.

Thus, the anti-c-Met antibody may specifically bind to an epitope which has 5 to 19 consecutive amino acids of the amino acid sequence of SEQ ID NO: 71, which consecutive amino acids include SEQ ID NO: 73 as an essential element. For example, the anti-c-Met antibody may specifically bind to an epitope including the amino acid sequence of SEQ ID NO: 71, SEQ ID NO: 72, or SEQ ID NO: 73.

In one embodiment, the anti-c-Met antibody or an antigen-binding fragment thereof may include:

at least one heavy chain complementarity determining region (CDR) selected from the group consisting of CDR-H1 including the amino acid sequence of SEQ ID NO: 4; CDR-H2 including the amino acid sequence of SEQ ID NO: 5 or SEQ ID NO: 2, or including an amino acid sequence of 8 to 19 consecutive amino acids within SEQ ID NO: 2 including amino acid residues from $3^{rd}$ to $10^{th}$ positions of SEQ ID NO: 2; and CDR-H3 including the amino acid sequence of SEQ ID NO: 6 or SEQ ID NO: 85, or including an amino acid sequence of 6 to 13 consecutive amino acids within SEQ ID NO: 85 including amino acid residues from $1^{st}$ to $6^{th}$ positions of SEQ ID NO: 85, or a heavy chain variable region including the at least one heavy chain complementarity determining region;

at least one light chain complementarity determining region (CDR) selected from the group consisting of CDR-L1 including the amino acid sequence of SEQ ID NO: 7, CDR-L2 including the amino acid sequence of SEQ ID NO: 8, and CDR-L3 including the amino acid sequence of SEQ ID NO: 9 or SEQ ID NO: 15 or SEQ ID NO: 86 or SEQ ID NO: 89, or including an amino acid sequence of 9 to 17 consecutive amino acids within SEQ ID NO: 89 including amino acid residues from $1^{st}$ to $9^{th}$ positions of SEQ ID NO: 89, or a light chain variable region including the at least one light chain complementarity determining region;

a combination of the at least one heavy chain complementarity determining region and the at least one light chain complementarity determining region; or a combination of the heavy chain variable region and the light chain variable region.

Herein, the amino acid sequences of SEQ ID NOS: 4 to 9 are respectively represented by the following Formulas I to VI, below:

Formula I
(SEQ ID NO: 4)
$Xaa_1$-$Xaa_2$-Tyr-Tyr-Met-Ser, wherein $Xaa_1$ is absent or Pro or Ser, and $Xaa_2$ is Glu or Asp, Formula II
(SEQ ID NO: 5)
Arg-Asn-$Xaa_3$-$Xaa_4$-Asn-Gly-$Xaa_5$-Thr, wherein $Xaa_3$ is Asn or Lys, Xaa is Ala or Val, and $Xaa_5$ is Asn or Thr, Formula III
(SEQ ID NO: 6)
Asp-Asn-Trp-Leu-$Xaa_6$-Tyr, wherein $Xaa_6$ is Ser or Thr, Formula IV
(SEQ ID NO: 7)
Lys-Ser-Ser-$Xaa_7$-Ser-Leu-Leu-Ala-$Xaa_8$-Gly-Asn-$Xaa_9$-$Xaa_{10}$-Asn-Tyr-Leu-Ala wherein $Xaa_7$ is His, Arg, Gln, or Lys, $Xaa_8$ is Ser or Trp, $Xaa_9$ is His or Gln, and $Xaa_{10}$ is Lys or Asn, Formula V
(SEQ ID NO: 8)
Trp-$Xaa_{11}$-Ser-$Xaa_{12}$-Arg-Val-$Xaa_{13}$ wherein $Xaa_{11}$ is Ala or Gly, $Xaa_{12}$ is Thr or Lys, and $Xaa_{13}$ is Ser or Pro, and Formula VI
(SEQ ID NO: 9)
$Xaa_{14}$-Gln-Ser-Tyr-Ser-$Xaa_{15}$-Pro-$Xaa_{16}$-Thr wherein $Xaa_{14}$ is Gly, Ala, or Gln, $Xaa_{15}$ is Arg, His, Ser, Ala, Gly, or Lys, and $Xaa_{16}$ is Leu, Tyr, Phe, or Met.

In one embodiment, the CDR-H1 may include an amino acid sequence selected from the group consisting of SEQ ID NOS: 1, 22, 23, and 24. The CDR-H2 may include an amino acid sequence selected from the group consisting of SEQ ID NOS: 2, 25, and 26. The CDR-H3 may include an amino acid sequence selected from the group consisting of SEQ ID NOS: 3, 27, 28, and 85. The CDR-L1 may include an amino acid sequence selected from the group consisting of SEQ ID NOS: 10, 29, 30, 31, 32, 33, and 106. The CDR-L2 may include an amino acid sequence selected from the group consisting of SEQ ID NOS: 11, 34, 35, and 36. The CDR-L3 may include an amino acid sequence selected from the group consisting of SEQ ID NOS: 12, 13, 14, 15, 16, 37, 86, and 89.

In another embodiment, the anti-c-Met antibody or an antigen-binding fragment thereof may include:

a heavy variable region including a polypeptide (CDR-H1) including an amino acid sequence selected from the group consisting of SEQ ID NOS: 1, 22, 23, and 24, a polypeptide (CDR-H2) including an amino acid sequence selected from the group consisting of SEQ ID NOS: 2, 25, and 26, and a polypeptide (CDR-H3) including an amino acid sequence selected from the group consisting of SEQ ID NOS: 3, 27, 28, and 85;

a light variable region including a polypeptide (CDR-L1) including an amino acid sequence selected from the group consisting of SEQ ID NOS: 10, 29, 30, 31, 32, 33 and 106, a polypeptide (CDR-L2) including an amino acid sequence selected from the group consisting of SEQ ID NOS: 11, 34, 35, and 36, and a polypeptide (CDR-L3) including an amino acid sequence selected from the group consisting of SEQ ID NOS 12, 13, 14, 15, 16, 37, 86, and 89; or a combination of the heavy variable region and the light variable region.

In one embodiment, the anti-c-Met antibody or antigen-binding fragment may include a heavy chain variable region including an amino acid sequence of SEQ ID NO: 17, 74, 87, 90, 91, 92, 93, or 94 and a light chain variable region including an amino acid sequence of SEQ ID NO: 18, 19, 20, 21, 75, 88, 95, 96, 97, 98, 99 or 107.

In one embodiment, the anti-c-Met antibody may be a monoclonal antibody. The monoclonal antibody may be produced from a hybridoma cell line deposited with Accession No. KCLRF-BP-00220, which binds specifically to the extracellular region of c-Met protein (refer to Korean Patent Publication No. 2011-0047698, the disclosure of which is incorporated in its entirety herein by reference).

The anti-c-Met antibody may include all the antibodies defined in Korean Patent Publication No. 2011-0047698.

By way of further example, the anti-c-Met antibody or the antibody fragment may include:

a heavy chain including the amino acid sequence selected from the group consisting of the amino acid sequence of SEQ ID NO: 62 (wherein the amino acid sequence from amino acid residues from the $1^{st}$ to $17^{th}$ positions is a signal peptide), or the amino acid sequence from the 18th to $462^{nd}$ positions of SEQ ID NO: 62; the amino acid sequence of SEQ ID NO: 64 (wherein the amino acid sequence from the $1^{st}$ to $17^{th}$ positions is a signal peptide) or the amino acid sequence from the $18^{th}$ to $461^{st}$ positions of SEQ ID NO: 64; and the amino acid sequence of SEQ ID NO: 66 (wherein the amino acid sequence from the $1^{st}$ to $17^{th}$ positions is a signal peptide), or the amino acid sequence from the $18^{th}$ to $460^{th}$ positions of SEQ ID NO: 66; and a light chain including the amino acid sequence selected from the group consisting of the amino acid sequence of SEQ ID NO: 68 (wherein the amino acid sequence from the $1^{st}$ to $20^{th}$ positions is a signal peptide) or the amino acid sequence from the $21^{st}$ to $240^{th}$ positions of SEQ ID NO: 68; the amino acid sequence of SEQ ID NO: 70 (wherein the amino acid sequence from the $1^{st}$ to $20^{th}$ positions is a signal peptide) or the amino acid sequence from the $21^{st}$ to $240^{th}$ positions of SEQ ID NO: 70, and the amino acid sequence of SEQ ID NO: 108.

For example, the anti-c-Met antibody may be selected from the group consisting of:

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 108;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 108; and an antibody including a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 108.

In particular embodiment, the anti-c-Met antibody may include a heavy chain including the amino acid sequence from the $18^{th}$ to $460^{th}$ positions of SEQ ID NO: 66 and a light chain including the amino acid sequence from the $21^{st}$ to $240^{th}$ positions of SEQ ID NO: 68.

The polypeptide of SEQ ID NO: 70 is a light chain including the human kappa (κ) constant region, and the polypeptide with the amino acid sequence of SEQ ID NO: 68 is a polypeptide obtained by replacing histidine at position 62 (corresponding to position 36 of SEQ ID NO: 68 according to kabat numbering) of the polypeptide with the amino acid sequence of SEQ ID NO: 70 with tyrosine. The production yield of the antibodies may be increased by the replacement. The polypeptide with the amino acid sequence of SEQ ID NO: 108 is a polypeptide obtained by replacing serine at position 32 of SEQ ID NO: 108 (corresponding to position 52 of SEQ ID NO: 68, which corresponds to position 27e according to kabat numbering in the amino acid sequence from amino acid residues 21 to 240 of SEQ ID NO: 68; positioned within CDR-L1) with tryptophan. By such replacement, antibodies and antibody fragments including such sequences exhibits increased activities, such as c-Met biding affinity, c-Met degradation activity, Akt phosphorylation inhibition, and the like.

In an embodiment, the anti-c-Met antibody may include a light chain complementarity determining region including the amino acid sequence of SEQ ID NO: 106, a light chain variable region including the amino acid sequence of SEQ ID NO: 107, or a alight chain including the amino acid sequence of SEQ ID NO: 108.

Animal-derived antibodies produced by immunizing non-immune animals with a desired antigen generally invoke immunogenicity when injected to humans for the purpose of medical treatment, and thus chimeric antibodies have been developed to inhibit such immunogenicity. Chimeric antibodies are prepared by replacing constant regions of animal-derived antibodies that cause an anti-isotype response with constant regions of human antibodies by genetic engineering. Chimeric antibodies are considerably improved in an anti-isotype response compared to animal-derived antibodies, but animal-derived amino acids still have variable regions, so that chimeric antibodies have side effects with respect to a potential anti-idiotype response. Humanized antibodies are developed to reduce such side effects. Humanized antibodies are produced by grafting complementarity determining regions (CDR) which serve an important role in antigen binding in variable regions of chimeric antibodies into a human antibody framework.

An important consideration in CDR grafting to produce humanized antibodies is choosing the optimized human antibodies for accepting CDR of animal-derived antibodies. Antibody database, analysis of a crystal structure, and technology for molecule modeling are used. However, even when the CDRs of animal-derived antibodies are grafted to the most optimized human antibody framework, amino acids positioned in a framework of the animal-derived CDRs affecting antigen binding are present. Therefore, in many cases, antigen binding affinity is not maintained, and thus application of additional antibody engineering technology for recovering the antigen binding affinity is necessary.

The anti-c-Met antibodies may be mouse-derived antibodies, mouse-human chimeric antibodies, humanized antibodies or human antibodies. The antibodies or antigen-binding fragments thereof may be isolated from a living body or non-naturally occurring. The antibodies or antigen-binding fragments thereof may be recombinant or synthetic.

An intact antibody includes two full-length light chains and two full-length heavy chains, in which each light chain is linked to a heavy chain by disulfide bonds. The antibody has a heavy chain constant region and a light chain constant region. The heavy chain constant region is of a gamma (γ), mu (μ), alpha (α), delta (δ), or epsilon (ε) type, which may be further categorized as gamma 1 (γ1), gamma 2(γ2), gamma 3(γ3), gamma 4(γ4), alpha 1(α1), or alpha 2(α2). The light chain constant region is of either a kappa (κ) or lambda (λ) type.

As used herein, the term "heavy chain" refers to full-length heavy chain, and fragments thereof, including a variable region $V_H$ that includes amino acid sequences sufficient to provide specificity to antigens, and three constant regions, $C_{H1}$, $C_{H2}$, and $C_{H3}$, and a hinge. The term "light chain" refers to a full-length light chain and fragments thereof, including a variable region $V_L$ that includes amino acid sequences sufficient to provide specificity to antigens, and a constant region $C_L$.

The term "complementarity determining region (CDR)" refers to an amino acid sequence found in a hyper variable region of a heavy chain or a light chain of immunoglobulin. The heavy and light chains may respectively include three CDRs (CDRH1, CDRH2, and CDRH3; and CDRL1, CDRL2, and CDRL3). The CDR may provide contact residues that play an important role in the binding of antibodies to antigens or epitopes. The terms "specifically binding" or "specifically recognized" is well known to one of ordinary skill in the art, and indicates that an antibody and an antigen specifically interact with each other to lead to an immunological activity.

The term "hinge region," as used herein, refers to a region between CH1 and CH2 domains within the heavy chain of an antibody which functions to provide flexibility for the antigen-binding site.

When an animal antibody undergoes a chimerization process, the IgG1 hinge of animal origin is replaced with a human IgG1 hinge while the disulfide bridges between two heavy chains are reduced from three to two in number. In addition, an animal-derived IgG1 hinge is shorter than a human IgG1 hinge. Accordingly, the rigidity of the hinge is changed. Thus, a modification of the hinge region may bring about an improvement in the antigen binding efficiency of the humanized antibody. The modification of the hinge region through amino acid deletion, addition, or substitution is well-known to those skilled in the art.

In one embodiment, the anti-c-Met antibody or an antigen-binding fragment thereof may be modified by the deletion, addition, or substitution of at least one amino acid residue on the amino acid sequence of the hinge region so that it exhibits enhanced antigen-binding efficiency. For example, the antibody may include a hinge region including the amino acid sequence of SEQ ID NO: 100, 101, 102, 103, 104, or 105. Preferably, the hinge region has the amino acid sequence of SEQ ID NO: 100 or 101.

The rest region other than the CDR region, the heavy chain variable region, and/or the light chain variable region, for example, a heavy chain constant region and a light chain constant region, may be from any subtype of immunoglobulin (e.g., IgA, IgD, IgE, IgG (IgG1, IgG2, IgG3, IgG4), IgM, etc.).

In one embodiment, the antibody may be an antigen-binding fragment selected from the group consisting of scFv, (scFv)$_2$, Fab, Fab', and F(ab')$_2$.

The term "antigen-binding fragment" used herein refers to fragments of an intact immunoglobulin including portions of a polypeptide including antigen-binding regions having the ability to specifically bind to the antigen. For example, the antigen-binding fragment may be scFv, (scFv)$_2$, Fab, Fab', or F(ab')$_2$, but is not limited thereto. Among the antigen-binding fragments, Fab that includes light chain and heavy chain variable regions, a light chain constant region, and a first heavy chain constant region $C_{H1}$, has one antigen-binding site.

The Fab' fragment is different from the Fab fragment, in that Fab' includes a hinge region with at least one cysteine residue at the C-terminal of $C_{H1}$.

The F(ab')$_2$ antibody is formed through disulfide bridging of the cysteine residues in the hinge region of the Fab' fragment.

Fv is the smallest antibody fragment with only a heavy chain variable region and a light chain variable region. Recombination techniques of generating the Fv fragment are widely known in the art.

Two-chain Fv includes a heavy chain variable region and a light chain region which are linked by a non-covalent bond. Single-chain Fv generally includes a heavy chain variable region and a light chain variable region which are linked by a covalent bond via a peptide linker or linked at the C-terminals to have a dimer structure like the two-chain Fv. The peptide linker may be the same as described in the above, for example, those having the amino acid length of 1 to 100, 2 to 50, particularly 5 to 25, and any kinds of amino acids may be included without any restrictions.

The antigen-binding fragments may be attainable using protease (for example, the Fab fragment may be obtained by restricted cleavage of a whole antibody with papain, and the F(ab')2 fragment may be obtained by cleavage with pepsin), or may be prepared by using a genetic recombination technique.

Figure 4:
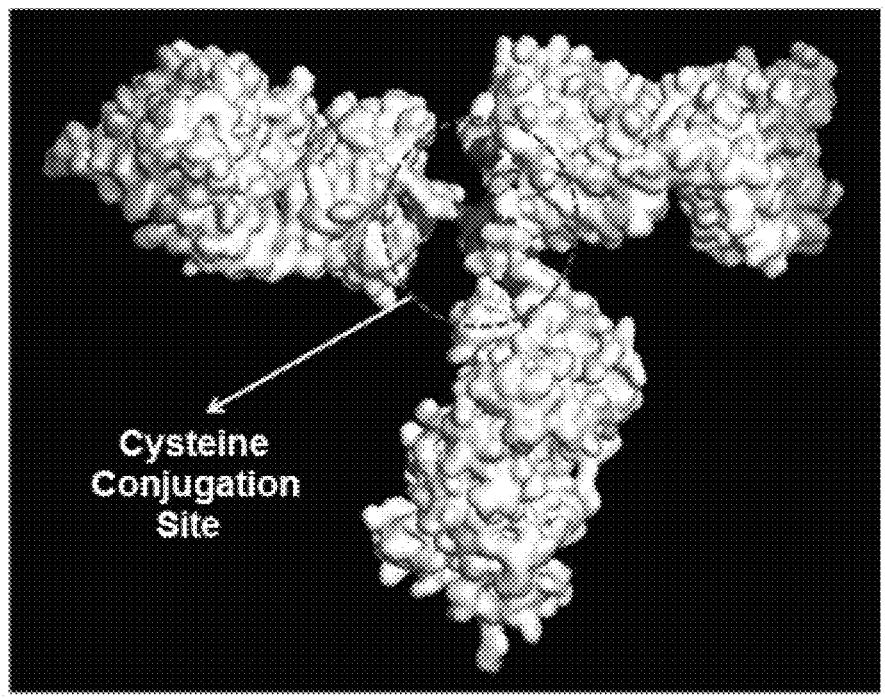
FIG. 4 is a set of images depicting stereostructures of antibody-drug conjugates, indicating an SH binding site and an $NH_2$ binding site within the respective conjugates.
Figure 4:
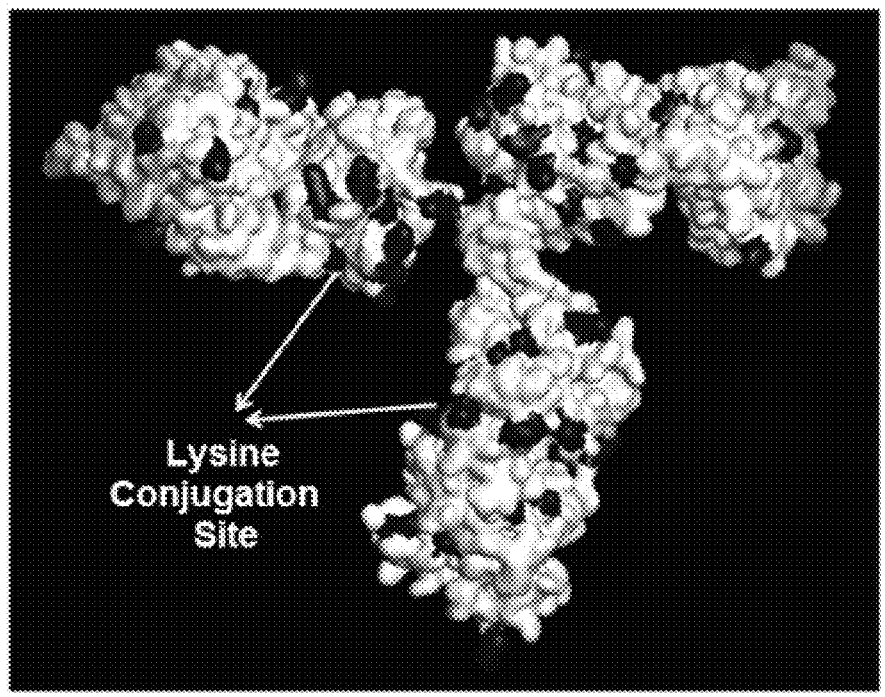
Figure 5:
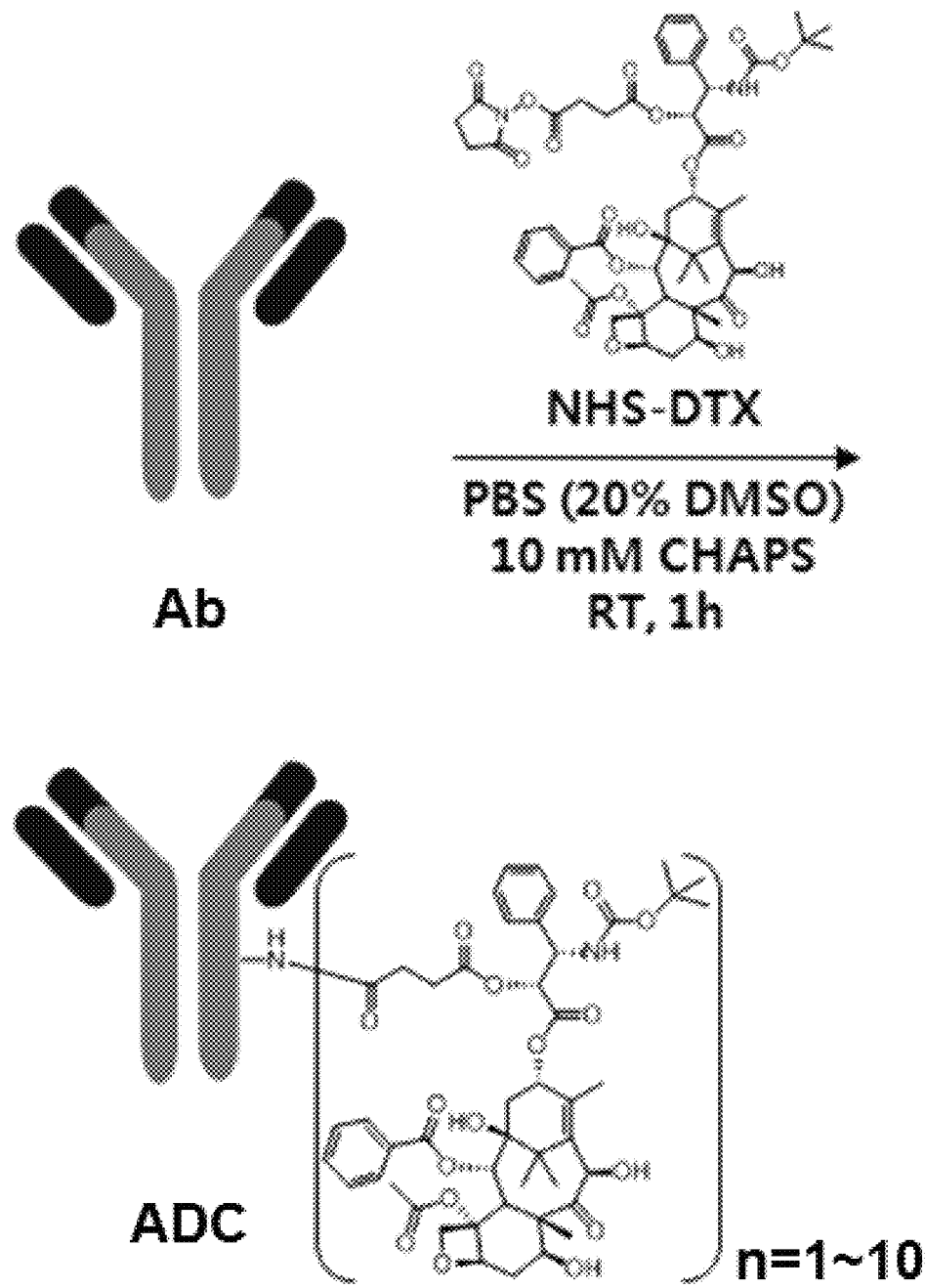
FIG. 5 is a schematic diagram depicting a reaction design for preparing an antibody-drug conjugate (ADC1) through an $NH_2$ coupling linkage.
Figure 7:
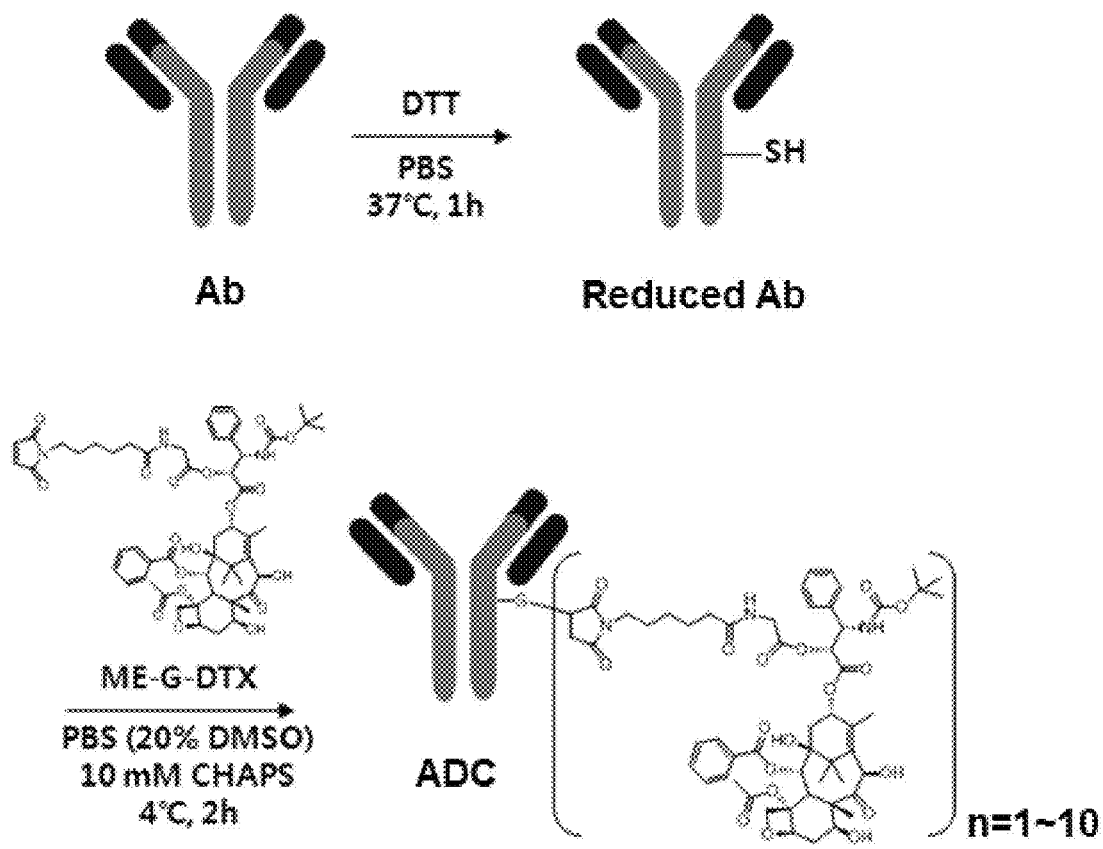
FIG. 7 is a schematic diagram depicting a reaction design for preparing an antibody-drug conjugate (ADC2) through an SH coupling linkage.

FIG. 4 shows stereostructures of antibody-drug conjugates, indicating a site at which the cytotoxic agent is conjugated to the anti-c-Met antibody while FIGS. 5 and 7 are schematic diagrams depicting processes of conjugating a drug to an antibody.

In the antibody-drug conjugate, one to ten cytotoxic agents (drug derivatives into which a functional group capable of linkage to the antibody is introduced either via a linker or directly) may be conjugated to one antibody (complete antibody or antigen-binding fragment) (see FIGS. 5 and 7). When two or more cytotoxic agents are conjugated to one antibody, they may be the same or different.

In order to increase the production yield of the conjugate with the minimalization of coagulation, oligomerization or dimerization therein, the molar ratio of antibody to drug (DAR; drug-to-antibody ratio; moles of drug/moles of antibody) in the antibody-drug conjugate may range from 1 to 10, from 1 to 8, from 1 to 5, from 3 to 8, from 3 to 5, or from 3.5 to 4.

The conjugate or the pharmaceutical composition may be provided, together with a pharmaceutical additive, such as a carrier, a diluent and/or an excipient.

A pharmaceutically acceptable carrier which is typically used for drug formulations may be available for the conjugate or the pharmaceutical composition. Examples of the carrier include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, and mineral oil, but are not limited thereto. In addition, the conjugate or the pharmaceutical composition may further include at least one selected from the group consisting of a diluent, an excipient, a lubricant, a humectant, a sweetener, a flavoring agent, an emulsifier, a suspending agent, and a preservative.

The conjugate or the pharmaceutical composition may be administered orally or parenterally. For parenteral administration, the administration may be carried out via intravenous, subcutaneous, intramuscular, intraperitoneal, intradermal, local, intranasal, intrapulmonary, and intrarectal routes, but is not limited thereto. For oral administration, however, the pharmaceutical composition is preferably coated or formulated to protect the active ingredient from being degraded in the stomach because proteins or peptides are digested by pepsin. In addition, the administration may be performed with the aid of an instrument adapted for delivering the pharmaceutical composition to target cells.

The term "pharmaceutically effective amount," as used herein, refers to an amount at which the active ingredient can exert a desired effect. A dose of the conjugate or the pharmaceutical composition may vary depending on various factors including the type of formulation, the patient's age, weight, and sex, the severity of the disorder being treated, diet, the time of administration, the route of administration, the rate of excretion, and sensitivity. For example, the pharmaceutically effective amount of the active ingredient in the conjugate or the pharmaceutical composition may range in single dose from 0.001 to 100 mg/kg, or from 0.02 to 50 mg/kg, but is not limited thereto.

The single dose may be formulated into a unit dose form or distributed into separate dose forms, or may be included within a multiple dose package.

The conjugate or the pharmaceutical composition may be formulated into solutions in oil or aqueous media, suspensions, syrup, emulsions, elixirs, powders, granules, tablets, or capsules, and in this context, a dispersant or a stabilizer may be further employed.

The cancer to the prevention and/or treatment of which the composition can be applied may be solid cancer or blood cancer. The cancer may be related to overexpression and/or abnormal activation of c-Met. Examples of the cancer may include squamous cell carcinoma, small-cell lung cancer, non-small-cell lung cancer, adrenocarcinoma of lung, squamous cell carcinoma of lung, peritoneal cancer, skin cancer, skin or intraocular melanoma, rectal cancer, perianal cancer, esophagus cancer, small intestine cancer, endocrine gland cancer, parathyroid cancer, adrenal cancer, soft-tissue sarcoma, urethral cancer, chronic or acute leukemia, lymphocytic lymphoma, hepatoma, gastric cancer, gastrointestinal cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, head or neck cancer, brain cancer, osteosarcoma, or a combination thereof. In addition, the scope of the cancer treatable with the conjugate or the composition may extend to a cancer where an anti-c-Met antibody exhibits agonism, and/or a cancer resistant to an anti-c-Met antibody, as well as c-Met expressing cancer (c-Met-positive cancer). The cancer may be a primary cancer or a metastatic cancer.

With regard to the prophylactic and/or therapeutic effect on cancer, the conjugate or the composition may have effects inhibiting migration, invasion, and/or metastasis of cancer, as well as inhibiting the growth of primary cancer cells.

Another embodiment provides an antibody-radioisotope conjugate including an anti-c-Met antibody and a radioisotope. Any radioisotope that is radioactive may be used. For example, it may be at least one selected from among the radioisotopes listed in Table 1, below. Functionally, it may be active as a cancer therapeutic or a tracer in cancer cells or tissues. The radioisotope is within the scope of a cytotoxic agent when used as a cancer therapeutic, and within the scope of a contrast agent when used as a tracer for imaging. Kinds and properties of radioisotopes available for therapy or imaging are well known in relevant arts. On the basis of the knowledge of the art, selection may be made of appropriate radioisotopes according to purposes. Representative radioisotopes are summarized, together with their properties, in Table 1, below:

TABLE 1

| Radioisotope | Representative | Description |
|---|---|---|
| Gallium | Gallium-67 | Produced in an accelerator. Used for medicinal diagnosis such as to image tumors and inflammation |
| | Gallium-68 | Produced in a generator (Ge-68). Positron emitting isotope for use in PET, and PET/CT |
| Copper | Copper-64 | Produced in an accelerator. Used in the imaging analysis of the effect of copper metabolism on genetic diseases, and the imaging analysis and treatment of Wilson and Menke diseases, and tumor. |
| | Copper-67 | Produced in an accelerator. Used in tumor treatment, injected together with monoclonal antibody into tumors so as to kill tumors and help the antibody act in tumors |
| Dysprosium | Dysprosium-165 | Produced in a nuclear reactor. Used to aggregate hydroxides for radiosynovectomy |
| Rhenium | Rhenium-186 | Produced in a nuclear reactor. Used to perform treatment and diagnosis simultaneously because of simultaneous emitting of beta and gamma radiation, relieving the pain of bone cancer. |
| | Rhenium-188 | Produced in a nuclear reactor. Used to irradiate beta radiation on the coronary artery upon vascular surgery |
| Rubidium | Rubidium-82 | Produced in a generator (Sr-82). Myocardial perfusion imaging, PET mechanism |
| Lutetium | Lutetium-177 | Produced in a nuclear reactor. Half life of 6.7. Emitting of beta/gamma radiation, prepared from Lu-176 Simultaneous diagnosis/treatment, intracranial treatment, relieving arthritis pain on synovial membrane extension |
| Fluorine | Florine-18 | Produced in an accelerator. Used as a tracer, a positron-emitting isotope for FLT, F-miso, and PET in the study of cerebral physiology and pathogenesis, such as in epilepsy, dementia, psychosis, etc. |
| Bismuth | Bismuth-213 | Produced in a nuclear reactor. Half life of 46 h. High energy (8.4 MeV) used to treat cancer by an alpha targeting method |
| Samarium | Samarium-153 | Produced in a nuclear reactor. Relieving pain of secondary cancer within bone, effective for treatment of prostate cancer and breast cancer |

TABLE 1-continued

| Radioisotope | Representative | Description |
|---|---|---|
| Oxygen | Oxygen-15 | Produced in an accelerator. a positron emitting isotope for PET, used in the study of cerebral physiology and pathology, such as in epilepsy, dementia, psychosis, etc. |
| Cesium | Cesium-137 | Produced in a nuclear reactor. Tumor treatment, measurement of accurate radiation doses to patients, intracranial treatment, relieving arthritis pain upon synovial membrane extension |
| Strontium | Strontium-85 | Used in the study of bone structure and metabolism |
| | Strontium-89 | Produced in a nuclear reactor. Beta radiation emitting radionuclide, effective for pain relief of prostate cancer and bone cancer. |
| Iodine | Erbium-169 | Produced in a nuclear reactor. Relieving arthritis pain at synovitis arthritis |
| Iodine | Iodine-123 | Produced in an accelerator. Used in the treatment of thyroid grand disease, brain disease, and other metabolic diseases |
| | Iodine-125 | Produced in a nuclear reactor. Used in the treatment of prostate cancer, intracranial treatment, the estimation and diagnosis of prostate cancer clearance, the diagnosis of leg thrombosis, and as radiation diagnosis reagent for clinical trial, and thyroid disease. Applied to biomedical study |
| | Iodine-131 | Produced in a nuclear reactor. Diagnosis and treatment of thyroid cancer, diagnosis of abnormal liver function, impaired bladder functions, and renal blood flow |
| Ytterbium | Ytterbium-169 | Produced in a nuclear reactor. Used in the study of cerebrospinal fluid, and to obtain gamma images in NDT |
| Yttrium | Yttrium-90 | Produced in a nuclear reactor. Intracranial treatment. Relieving pain of arthritis upon synovial membrane extension, Ce, Au, Ru also used |
| Gold | Au-198 | Applied to vessels or tissues to obtain images. Intracranial treatment, Relieving pain of arthritis upon synovial membrane extension |
| Phosphorus | Phosphorus-32 | Produced in a nuclear reactor. Used in the treatment of polycythemia, and the molecular biology and genetics study |
| Indium | Indium-111 | Produced in an accelerator. Used in the study of brain diseases, rectal diseases, infections, special diagnosis, etc. |
| Germanium | Germanium-68 | Produced in an accelerator. PET, Ga-68 generator |
| Nitrogen | Nitrogen-13 | Produced in an accelerator. Positron emitting isotope for PET. Used in the study of cerebral physiology and pathogenesis, such as in epilepsy, dementia, psychosis, etc. |
| Cobalt | Cobalt-57 | Produced in an accelerator. Used as a maker for inferring organ sizes, an intrapulmonary diagnostic reagent, and a tracer for diagnosis of pernicious anemia |
| | Cobalt-60 | Produced in a nuclear reactor. External radiation some, used to sterilize surgical instruments, improve the reliability and safety of industrial petroleum burners, and investigate foods, and in radiographic examination |
| Krypton | Krypton-81: | Produced in a generator (Rh-81). Images of the lung of asthma patients, diagnosis of lung function and diseases |
| Carbon | Carbon-11 | Produced in an accelerator. Positron emitting isotope for PET, used in the study of cerebral physiology and pathogenesis, such as in epilepsy, dementia, psychosis, etc. |
| Thallium | Thallium-201 | Produced in an accelerator. Used in nuclear medicine for heart diseases and tumors |
| Technetium | Technetium-99m | Produced in a generator (inclusive of Mo-99). Nuclear medicine diagnosis, radiopharmaceuticals. Used as different forms in the study of brain, bone, liver, kidney, and blood flow |
| Palladium | Palladium-103 | Produced in a nuclear reactor. Treatment of early prostate cancer. Radiation source for permanent skin graft |
| Potassium | Potassium-42 | Produced in a nuclear reactor. Used to determine potassium change in coronary flow |
| Holmium | Holmium-166 | Produced in a nuclear reactor. Diagnosis and treatment of liver cancer |

Another embodiment provides an antibody-contrast agent conjugate, including an anti-c-Met antibody, and a contrast agent. Another embodiment provides a composition for intracellular imaging, including the antibody-contrast agent. Another embodiment provides a method for intracellular imaging (visualizing), including administering the anti-c-Met antibody-contrast agent conjugate to a subject and visualizing the anti-c-Met antibody-contrast agent conjugate. In this regard, the subject may be selected from the group consisting of those needed to image the inside of their cells or themselves, e.g., cells expressing c-Met (c-Met positive cells). For example, all mammals including primates such as humans and monkeys, and rodents such as mice and rats, cells or tissues derived (isolated) therefrom, and cultures of the cells or tissues may fall into the scope of the subject. For example, a patient with cancer, or cancer cells or tissues derived (isolated) from the patients, or a culture thereof may be a subject.

The anti-c-Met antibody used in the anti-c-Met antibody-contrast agent is as described above. As long as it can be used to image the inside of cells, e.g., cells expressing c-Met (c-Met positive cells), any contrast agent is available. It may be selected from among those used for MRI (Magnetic Resonance Imaging) and PET (Positron Emission Tomography). For example, iron oxide, gadolinium, or a radioisotope may be used. The radioisotope is as described above.

Based on its internalization performance, the anti-c-Met antibody can be applied to the intracellular delivery of various bioactive materials.

Another embodiment provides a pharmaceutical composition for the intracellular delivery of a bioactive material, including an anti-c-Met antibody. Another embodiment provides a method for delivering a bioactive material into cells, using an anti-c-Met antibody. Another embodiment provides an anti-c-Met antibody for delivering a bioactive material into cells. Another embodiment provides a use of an antic-Met antibody in delivering a bioactive material into cells or in preparing a pharmaceutical composition for the intracellular delivery of a bioactive material.

Exhibiting not only a pharmaceutical effect of the anti-c-Met antibody in synergy with the bioactive material, but also taking advantage of the internalization performance of the anti-c-Met antibody in the intracellular delivery of the bioactive material, with the concomitant subjugation of problems with individual components, e.g., agonism of the anti-c-Met antibody and resistance to the bioactive material, the anti-c-Met antibody-bioactive material conjugate is effectively applicable to the treatment of various diseases or diseased cells and to the visualization of various cells.

Hereafter, the present disclosure will be described in detail by examples.

The following examples are intended merely to illustrate the invention and are not construed to restrict the invention.

EXAMPLES

Reference Example: Construction of Anti-C-Met Antibody 1.1. Production of "AbF46", a Mouse Antibody to c-Met
1.1.1. Immunization of Mouse To obtain immunized mice necessary for the development of a hybridoma cell line, each of five BALB/c mice (Japan SLC, Inc.), 4 to 6 weeks old, was intraperitoneally injected with a mixture of 100 µg of human c-Met/Fc fusion protein (R&D Systems) and one volume of complete Freund's adjuvant. Two weeks after the injection, second intraperitoneal injection was conducted on the same mice with a mixture of 50 µg of human c-Met/Fc protein and one volume of incomplete Freund's adjuvant. One week after the second immunization, the immune response was finally boosted. Three days later, blood was taken from the tail and the sera were 1/1000 diluted in PBS and used to examine a titer of antibody to c-Met by ELISA. Mice found to have a sufficient antibody titer were selected for use in the cell fusion process.

1.1.2. Cell Fusion and Production of Hybridoma

Three days before cell fusion, BALB/c mice (Japan SLC, Inc.) were immunized with an intraperitoneal injection of a mixture of 50 µg of human c-Met/Fc fusion protein and one volume of PBS. The immunized mice were anesthetized before excising the spleen from the left half of the body. The spleen was meshed to separate splenocytes which were then suspended in a culture medium (DMEM, GIBCO, Invitrogen). The cell suspension was centrifuged to recover the cell layer. The splenocytes thus obtained ($1\times10^8$ cells) were mixed with myeloma cells (Sp2/0) ($1\times10^8$ cells), followed by spinning to give a cell pellet. The cell pellet was slowly suspended, treated with 45% polyethylene glycol (PEG) (1 mL) in DMEM for 1 min at 37° C., and supplemented with 1 mL of DMEM. To the cells was added 10 mL of DMEM over 10 min, after which incubation was conducted in water at 37° C. for 5 min. Then the cell volume was adjusted to 50 mL before centrifugation. The cell pellet thus formed was resuspended at a density of $1-2\times10^5$ cells/mL in a selection medium (HAT medium) and 0.1 mL of the cell suspension was allocated to each well of 96-well plates which were then incubated at 37° C. in a $CO_2$ incubator to establish a hybridoma cell population.

1.1.3. Selection of Hybridoma Cells Producing Monoclonal Antibodies to c-Met Protein From the hybridoma cell population established in Reference Example 1.1.2, hybridoma cells which showed a specific response to c-Met protein were screened by ELISA using human c-Met/Fc fusion protein and human Fc protein as antigens.

Human c-Met/Fc fusion protein was seeded in an amount of 50 (2 µg/mL)/well to microtiter plates and allowed to adhere to the surface of each well. The antibody that remained unbound was removed by washing. For use in selecting the antibodies that do not bind c-Met but recognize Fc, human Fc protein was attached to the plate surface in the same manner.

The hybridoma cell culture obtained in Reference Example 1.1.2 was added in an amount of 50 µL, to each well of the plates and incubated for 1 hour. The cells remaining unreacted were washed out with a sufficient amount of Tris-buffered saline and Tween 20 (TBST). Goat anti-mouse IgG-horseradish peroxidase (HRP) was added to the plates and incubated for 1 hour at room temperature. The plates were washed with a sufficient amount of TBST, followed by reacting the peroxidase with a substrate (OPD). Absorbance at 450 nm was measured on an ELISA reader.

Like this, hybridoma cell lines which secrete antibodies that specifically and strongly bind to human c-Met but not human Fc were selected repeatedly. From the hybridoma cell lines obtained by repeated selection, a single clone producing a monoclonal antibody was finally separated by limiting dilution. The single clone of the hybridoma cell line producing the monoclonal antibody was deposited with the Korean Cell Line Research Foundation, an international depository authority located at Yungun-Dong, Jongno-Gu, Seoul, Korea, on Oct. 6, 2009, with accession No. KCLRF-BP-00220 according to the Budapest Treaty (refer to Korean Patent Laid-Open Publication No. 2011-0047698).

1.1.4. Production and Purification of Monoclonal Antibody

The hybridoma cell line obtained in Reference Example 1.1.3 was cultured in a serum-free medium, and the monoclonal antibody were produced and purified from the cell culture.

First, the hybridoma cells cultured in 50 mL of a medium (DMEM) supplemented with 10% (v/v) FBS were centrifuged and the cell pellet was washed twice or more with 20 mL of PBS to remove the FBS therefrom. Then, the cells were resuspended in 50 mL of DMEM and incubated for 3 days at 37° C. in a $CO_2$ incubator.

After the cells were removed by centrifugation, the supernatant was stored at 4° C. before use or immediately used for the separation and purification of the antibody. An AKTA system (GE Healthcare) equipped with an affinity column (Protein G agarose column; Pharmacia, USA) was used to purify the antibody from 50 to 300 mL of the supernatant, followed by concentration with an filter (Amicon). The antibody in PBS was stored before use in the following examples.

1.2. Construction of chAbF46, a Chimeric Antibody to c-Met

A mouse antibody is apt to elicit immunogenicity in humans. To solve this problem, chAbF46, a chimeric antibody, was constructed from the mice antibody AbF46 produced in Example 1 by replacing the constant region, but not the variable region responsible for antibody specificity, with an amino sequence of human IgG1 antibody.

In this regard, a gene was designed to include the nucleotide sequence of "EcoRI-signal sequence-VH-NheI-CH-TGA-XhoI" (SEQ ID NO: 38) for a heavy chain and the nucleotide sequence of "EcoRI-signal sequence-VL-BsiWI-CL-TGA-XhoI" (SEQ ID NO: 39) for a light chain and synthesized. Then, a DNA fragment having the heavy chain nucleotide sequence (SEQ ID NO: 38) and a DNA fragment having the light chain nucleotide sequence (SEQ ID NO: 39) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen), and a pcDNA™3.3-TOPO TA Cloning Kit (Cat no. 8300-01), respectively.

Each of the vectors thus constructed was amplified with the aid of a Qiagen Maxiprep kit (Cat no. 12662). The vectors which respectively carried the heavy chain and the light chain were co-transfected at a ratio of 4:1 (80 µg:20 µg) into 293T cells ($2.5 \times 10^7$). The transfection into 293T cells ($2.5 \times 10^7$) was performed in the presence of 360 µL of 2M $CaCl_2$.

Afterwards, the cells were incubated in DMEM supplemented with 10% (v/v) FBS for 5 hours at 37° C. under a 5% $CO_2$ condition and then in FBS-free DMEM for 48 hours at 37° C. under a 5% $CO_2$ condition.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a chimeric antibody AbF46 (hereinafter referred to as "chAbF46").

1.3. Construction of Humanized Antibody huAbF46 from Chimeric Antibody chAbF46

1.3.1. Heavy Chain Humanization

To design two domains H1-heavy and H3-heavy, human germline genes which share the highest homology with the VH gene of the mouse antibody AbF46 purified in Reference Example 1.2 were analyzed. An Ig BLAST (National Center for Biotechnology Information (NCBI) of Bethesda, Md.) result revealed that the VH3-71 has a homology of 83% at the amino acid level. CDR-H1, CDR-H2, and CDR-H3 of the mouse antibody AbF46 were defined according to Kabat numbering. A design was made to introduce the CDR of the mouse antibody AbF46 into the framework of VH3-71. Hereupon, back mutations to the amino acid sequence of the mouse AbF46 were conducted at positions 30 (S→T), 48 (V→L), 73 (D→N), and 78 (T→L). Then, H1 was further mutated at positions 83 (R→K) and 84 (A→T) to finally establish H1-heavy (SEQ ID NO: 40) and H3-heavy (SEQ ID NO: 41).

For use in designing H4-heavy, human antibody frameworks were analyzed by a search for BLAST. The result revealed that the VH3 subtype, known to be most stable, is very similar in framework and sequence to the mouse antibody AbF46. CDR-H1, CDR-H2, and CDR-H3 of the mouse antibody AbF46 were defined according to Kabat numbering and introduced into the VH3 subtype to construct H4-heavy (SEQ ID NO: 42).

1.3.2. Light Chain Humanization

To design two domains H1-light (SEQ ID NO: 43) and H2-light (SEQ ID NO: 44), human germline genes which share the highest homology with the VH gene of the mouse antibody AbF46 were analyzed. An Ig BLAST search result revealed that VK4-1 has a homology of 75% at the amino acid level. CDR-L1, CDR-L2, and CDR-L3 of the mouse antibody AbF46 were defined according to Kabat numbering. A design was made to introduce the CDR of the mouse antibody AbF46 into the framework of VK4-1. Hereupon, back mutations to the amino acid sequence of the mouse AbF46 were conducted at positions 36 (Y→H), 46 (L→M), and 49 (Y→I). Only one back mutation was conducted at position 49 (Y→I) on H2-light.

To design H3-light (SEQ ID NO: 45), human germline genes which share the highest homology with the VL gene of the mouse antibody AbF46 were analyzed by a search for BLAST. As a result, VK2-40 was selected as well. VL and VK2-40 of the mouse antibody AbF46 were found to have a homology of 61% at an amino acid level. CDR-L1, CDR-L2, and CDR-L3 of the mouse antibody were defined according to Kabat numbering and introduced into the framework of VK4-1. Back mutations were conducted at positions 36 (Y→H), 46 (L→M), and 49 (Y→I) on H3-light.

For use in designing H4-light (SEQ ID NO: 46), human antibody frameworks were analyzed. A BLAST search revealed that the Vk1 subtype, known to be the most stable, is very similar in framework and sequence to the mouse antibody AbF46. CDR-L1, CDR-L2, and CDR-L3 of the mouse antibody AbF46 were defined according to Kabat numbering and introduced into the Vk1 subtype. Hereupon, back mutations were conducted at positions 36 (Y→H), 46 (L→M), and 49 (Y→I) on H4-light.

Thereafter, DNA fragments having the heavy chain nucleotide sequences (H1-heavy; SEQ ID NO: 47, H3-heavy; SEQ ID NO: 48, H4-heavy; SEQ ID NO: 49) and DNA fragments having the light chain nucleotide sequences (H1-light; SEQ ID NO: 50, H2-light; SEQ ID NO: 51, H3-light; SEQ ID NO: 52, H4-light; SEQ ID NO: 53) were digested with EcoRI (NEB, R0101S) and XhoI (NEB, R0146S) before cloning into a pOptiVEC™-TOPO TA Cloning Kit enclosed in an OptiCHO' Antibody Express Kit (Cat no. 12762-019, Invitrogen) and a pcDNA™3.3-TOPO TA Cloning Kit (Cat no. 8300-01), respectively, so as to construct recombinant vectors for expressing a humanized antibody.

Each of the recombinant vectors was amplified using Qiagen Maxiprep kit (Cat no. 12662). The vectors which respectively carried the heavy chain and the light chain were co-transfected at a ratio of 4:1 (80 µg:20 µg) into 293T cells ($2.5 \times 10^7$). The transfection into 293T cells ($2.5 \times 10^7$) was performed in the presence of 360 µL of 2M $CaCl_2$. Afterwards, the cells were incubated in DMEM supplemented with 10% (v/v) FBS for 5 hours at 37° C. under a 5% $CO_2$ condition, and then in FBS-free DMEM for 48 hours at 37° C. under a 5% $CO_2$ condition.

After centrifugation, the supernatant were applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a humanized antibody AbF46 (hereinafter referred to as "huAbF46"). The humanized antibody huAbF46 used in the following examples comprised a combination of H4-heavy (SEQ ID NO: 42) and H4-light (SEQ ID NO: 46).

1.4. Construction of scFV Library of huAbF46 Antibody

For use in constructing an scFv of the huAbF46 antibody from the heavy and light chain variable regions of the huAbF46 antibody, a gene was designed to have the structure of "VH-linker-VL" for each of the heavy and the light chain variable region, with the linker including the amino acid sequence "GLGGLGGGGSGGGGSGGSSGVGS" (SEQ ID NO: 54). A polynucleotide sequence (SEQ ID NO: 55) coding for the designed scFv of huAbF46 was synthesized in Bioneer and an expression vector for the polynucleotide had the nucleotide sequence of SEQ ID NO: 56.

After expression, the product was found to exhibit specificity to c-Met.

1.5. Construction of Library Genes for Affinity Maturation

1.5.1. Selection of Target CDR and Synthesis of Primer

The affinity maturation of huAbF46 was achieved. First, six complementary determining regions (CDRs) were defined according to Kabat numbering. The CDRs are given in Table 2, below.

TABLE 2

| CDR | Amino Acid Sequence |
| --- | --- |
| CDR-H1 | DYYMS (SEQ ID NO: 1) |
| CDR-H2 | FIRNKANGYTTEYSASVKG (SEQ ID NO: 2) |
| CDR-H3 | DNWFAY (SEQ ID NO: 3) |
| CDR-L1 | KSSQSLLASGNQNNYLA (SEQ ID NO: 10) |
| CDR-L2 | WASTRVS (SEQ ID NO: 11) |
| CDR-L3 | QQSYSAPLT (SEQ ID NO: 12) |

For use in the introduction of random sequences into the CDRs of the antibody, primers were designed as follows. Conventionally, N codons were utilized to introduce bases at the same ratio (25% A, 25% G, 25% C, 25% T) into desired sites of mutation. In this experiment, the introduction of random bases into the CDRs of huAbF46 was conducted in such a manner that, of the three nucleotides per codon in the wild-type polynucleotide encoding each CDR, the first and second nucleotides conserved over 85% of the entire sequence while the other three nucleotides were introduced at the same percentage (each 5%) and that the same possibility was imparted to the third nucleotide (33% G, 33% C, 33% T).

Figure 2:
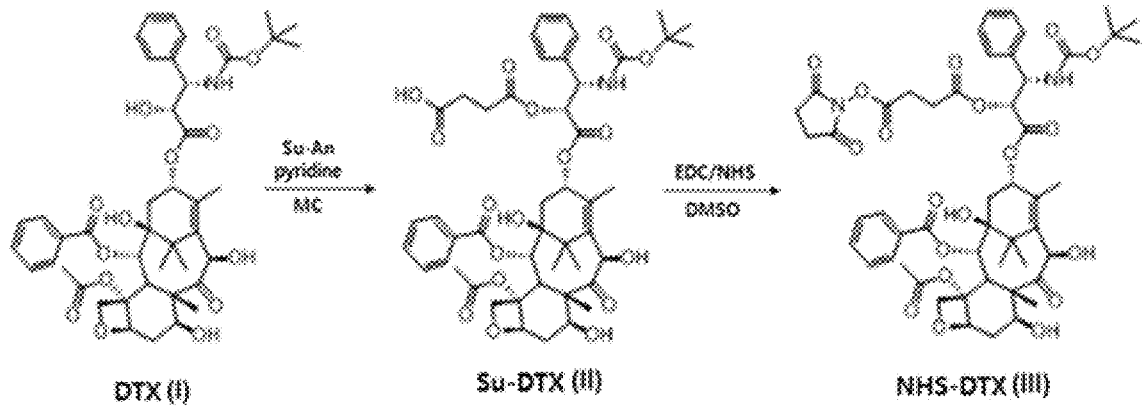
FIG. 2 is a schematic diagram showing reaction schemes designed to prepare a docetaxel (DTX) derivative for use in the preparation of an antibody-drug conjugate (ADC)
Figure 2:
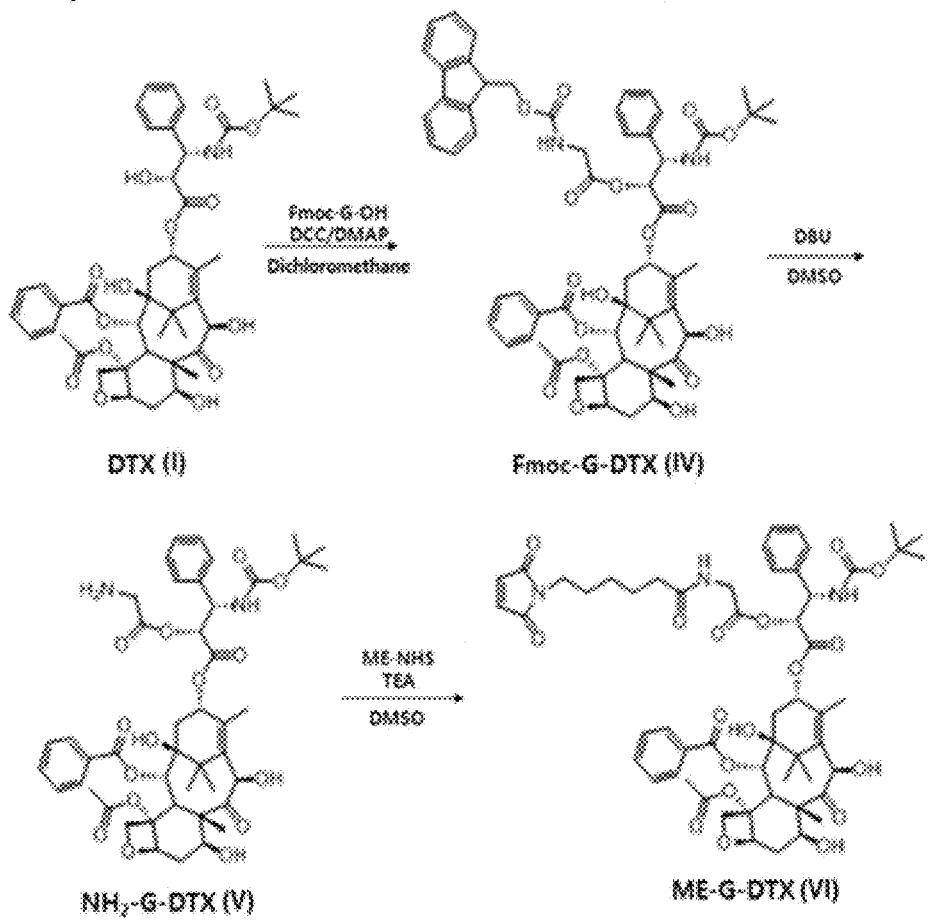

1.5.2. Construction of Library of huAbF46 Antibodies and Affinity for c-Met The construction of antibody gene libraries through the introduction of random sequences was carried out using the primers synthesized in the same manner as in Reference Example 1.5.1. Two PCR products were obtained, as shown in FIG. 2, using a polynucleotide covering the scFV of huAbF46 as a template, and were subjected to overlap extension PCR to give scFv library genes for huAbF46 antibodies in which only desired CDRs were mutated. Libraries targeting each of the six CDRs prepared from the scFV library genes were constructed.

The affinity for c-Met of each library was compared to that of the wildtype. Most libraries were lower in affinity for c-Met, compared to the wild-type. The affinity for c-Met was retained in some mutants.

1.6. Selection of Antibody with Improved Affinity from Libraries

After maturation of the affinity of the constructed libraries for c-Met, the nucleotide sequence of scFv from each clone was analyzed. The nucleotide sequences thus obtained are summarized in Table 3 and were converted into IgG forms. Four antibodies which were respectively produced from clones L3-1, L3-2, L3-3, and L3-5 were used in the subsequent experiments.

TABLE 3

| Clone | Library constructed | CDR Sequence |
| --- | --- | --- |
| H11-4 | CDR-H1 | PEYYMS (SEQ ID NO: 22) |
| YC151 | CDR-H1 | PDYYMS (SEQ ID NO: 23) |
| YC193 | CDR-H1 | SDYYMS (SEQ ID NO: 24) |
| YC244 | CDR-H2 | RNNANGNT (SEQ ID NO: 25) |
| YC321 | CDR-H2 | RNKVNGYT (SEQ ID NO: 26) |
| YC354 | CDR-H3 | DNWLSY (SEQ ID NO: 27) |
| YC374 | CDR-H3 | DNWLTY (SEQ ID NO: 28) |
| L1-1 | CDR-L1 | KSSHSLLASGNQNNYLA (SEQ ID NO: 29) |
| L1-3 | CDR-L1 | KSSRSLLSSGNHKNYLA (SEQ ID NO: 30) |
| L1-4 | CDR-L1 | KSSKSLLASGNQNNYLA (SEQ ID NO: 31) |
| L1-12 | CDR-L1 | KSSRSLLASGNQNNYLA (SEQ ID NO: 32) |
| L1-22 | CDR-L1 | KSSHSLLASGNQNNYLA (SEQ ID NO: 33) |
| L2-9 | CDR-L2 | WASKRVS (SEQ ID NO: 34) |
| L2-12 | CDR-L2 | WGSTRVS (SEQ ID NO: 35) |
| L2-16 | CDR-L2 | WGSTRVP (SEQ ID NO: 36) |
| L3-1 | CDR-L3 | QQSYSRPYT (SEQ ID NO: 13) |
| L3-2 | CDR-L3 | GQSYSRPLT (SEQ ID NO: 14) |
| L3-3 | CDR-L3 | AQSYSHPFS (SEQ ID NO: 15) |
| L3-5 | CDR-L3 | QQSYSRPFT (SEQ ID NO: 16) |
| L3-32 | CDR-L3 | QQSYSKPFT (SEQ ID NO: 37) |

1.7. Conversion of Selected Antibodies into IgG

Respective polynucleotides coding for heavy chains of the four selected antibodies were designed to have the structure of "EcoRI-signal sequence-VH-NheI-CH-XhoI" (SEQ ID NO: 38). The heavy chains of huAbF46 antibodies were used as they were because their amino acids were not changed during affinity maturation. In the case of the hinge region, however, the U6-HC7 hinge (SEQ ID NO: 57) was employed instead of the hinge of human IgG1. Genes were also designed to have the structure of "EcoRI-signal sequence-VL-BsiWI-CL-XhoI" for the light chain. Polypeptides encoding light chain variable regions of the four antibodies which were selected after the affinity maturation were synthesized in Bioneer. Then, a DNA fragment having the heavy chain nucleotide sequence (SEQ ID NO: 38) and DNA fragments having the light chain nucleotide sequences ((DNA fragment including L3-1-derived CDR-L3: SEQ ID NO: 58, DNA fragment including L3-2-derived CDR-L3: SEQ ID NO: 59, DNA fragment including L3-3-derived CDR-L3: SEQ ID NO: 60, and DNA fragment including L3-5-derived CDR-L3: SEQ ID NO: 61)) were digested with EcoRI (NEB, R0101S) and XhoI (NEB, R0146S) before cloning into a pOptiVEC™-TOPO TA Cloning Kit enclosed in an OptiCHO' Antibody Express Kit (Cat no. 12762-019, Invitrogen) and a pcDNA™3.3-TOPO TA Cloning Kit (Cat no. 8300-01), respectively, so as to construct recombinant vectors for expressing affinity-matured antibodies.

Each of the recombinant vectors was amplified using a Qiagen Maxiprep kit (Cat no. 12662). The vectors which respectively carried the heavy chain and the light chain were co-transfected at a ratio of 4:1 (80 µg:20 µg) into 293T cells (2.5×10⁷). The transfection into 293T cells (2.5×10⁷) was performed in the presence of 360 μL of 2M CaCl₂. Afterwards, the cells were incubated in DMEM supplemented with 10% (v/v) FBS for 5 hours at 37° C. under a 5% CO₂ condition and then in FBS-free DMEM for 48 hours at 37° C. under a 5% CO₂ condition.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify four affinity-matured antibodies (hereinafter referred to as "huAbF46-H4-A1 (L3-1 origin), huAbF46-H4-A2 (L3-2 origin), huAbF46-H4-A3 (L3-3 origin), and huAbF46-H4-A5 (L3-5 origin)," respectively).

1.8. Construction of Constant Region- and/or Hinge Region-Substituted huAbF46-H4-A1

Among the four antibodies selected in Reference Example 1.7, huAbF46-H4-A1 was found to be the highest in affinity for c-Met and the lowest in Akt phosphorylation and c-Met degradation degree. In the antibody, the hinge region, or the constant region and the hinge region, were substituted.

The antibody huAbF46-H4-A1 (U6-HC7) was composed of a heavy chain including the heavy chain variable region of huAbF46-H4-A1, U6-HC7 hinge and the constant region of human IgG1 constant region, and a light chain including the light chain variable region of huAbF46-H4-A1 and human kappa constant region. The antibody huAbF46-H4-A1 (IgG2 hinge) was composed of a heavy chain including a heavy chain variable region, a human IgG2 hinge region, and a human IgG1 constant region, and a light chain including the light chain variable region of huAbF46-H4-A1 and a human kappa constant region. The antibody huAbF46-H4-A1 (IgG2 Fc) was composed of the heavy chain variable region of huAbF46-H4-A1, a human IgG2 hinge region, and a human IgG2 constant region, and a light chain including the light variable region of huAbF46-H4-A1 and a human kappa constant region. Hereupon, the histidine residue at position 36 on the human kappa constant region of the light chain was changed into tyrosine in all of the three antibodies to increase antibody production.

For use in constructing the three antibodies, a polynucleotide (SEQ ID NO: 63) coding for a polypeptide (SEQ ID NO: 62) composed of the heavy chain variable region of huAbF46-H4-A1, a U6-HC7 hinge region, and a human IgG1 constant region, a polynucleotide (SEQ ID NO: 65) coding for a polypeptide (SEQ ID NO: 64) composed of the heavy chain variable region of huAbF46-H4-A1, a human IgG2 hinge region, and a human IgG1 region, a polynucleotide (SEQ ID NO: 67) coding for a polypeptide (SEQ ID NO: 66) composed of the heavy chain variable region of huAbF46-H4-A1, a human IgG2 region, and a human IgG2 constant region, and a polynucleotide (SEQ ID NO: 69) coding for a polypeptide (SEQ ID NO: 68) composed of the light chain variable region of huAbF46-H4-A1, with a tyrosine residue instead of histidine at position 36, and a human kappa constant region were synthesized in Bioneer. Then, the DNA fragments having heavy chain nucleotide sequences were inserted into a pOptiVEC®-TOPO TA Cloning Kit enclosed in an OptiCHO' Antibody Express Kit (Cat no. 12762-019, Invitrogen) while DNA fragments having light chain nucleotide sequences were inserted into a pcDNA™3.3-TOPO TA Cloning Kit (Cat no. 8300-01) so as to construct vectors for expressing the antibodies.

Each of the vectors thus constructed was amplified with the aid of a Qiagen Maxiprep kit (Cat no. 12662). The vectors which respectively carried the heavy chain and the light chain were co-transfected at a ratio of 4:1 (80 μg:20 μg) into 293T cells (2.5×10⁷). The transfection into 293T cells (2.5×10⁷) was performed in the presence of 360 of 2M CaCl₂. Afterwards, the cells were incubated in DMEM supplemented with 10% (v/v) FBS for 5 hours at 37° C. under a 5% CO₂ condition and then in FBS-free DMEM for 48 hours at 37° C. under a 5% CO₂ condition.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with IgG elution buffer (Thermo Scientific, 21004). The buffer was exchanged with PBS to finally purify three antibodies (huAbF46-H4-A1(U6-HC7), huAbF46-H4-A1 (IgG2 hinge), and huAbF46-H4-A1 (IgG2 Fc)). Among the 3 antibodies, huAbF46-H4-A1 (IgG2 Fc)) was exemplarily selected, named as L3-1Y/IgG2 antibody, and used in the following examples.

Example 1: Internalization of Anti-c-Met Antibody

The cell line OE33 (esophageal cancer cell line, ECACC (European Collection of Cell Cultures), #96070808), which overexpresses both c-Met and HER2, was incubated for 0, 10, 30 or 60 min with 1 ug/ml of the anti-c-Met antibody L3-1Y/IgG2, or Herceptin (Roche) to which an equal amount of the fluorescent FNR675 (BioActs, # PWS1515) was previously labeled, and then observed under a confocal microscope (FIG. 1A). Separately, OE33 cells were incubated in the presence of both FITC-labeled anti-c-Met antibody L3-1Y/IgG2 and FNR675-labeled Herceptin, each 1 ug/ml, followed by confocal microscopy to compare internalization into the same cells therebetween (FIG. 1B).

Results are shown in FIG. 1. As can be seen in the photographs of FIG. 1, the anti-HER2 antibody Herceptin was observed not to enter the cells, but to remain on cell surfaces whereas a significant number of the anti-c-Met antibody L3-1Y/IgG2 was detected inside the cells. These results indicate the excellent internalization performance of the anti-c-Met antibody L3-1Y/IgG2.

Example 2: Derivatization of Docetaxel

Docetaxel (Sigma-Aldrich) was derivatized with a functional group capable of linking to an antibody, as illustrated in the reaction schemes of FIG. 2.

2-1. Derivatization of Docetaxel for Amine Coupling (FIG. 2, Upper)

A docetaxel derivative capable of conjugating to the primary amine of a lysine residue from an antibody was prepared according to the following two-step reaction (FIG. 2).

First, docetaxel (Sigma, 200 mg) and succinic anhydride (Sigma, excess by 2 mole times) were dissolved in dichloromethane (Sigma, 10 mg DTX/mL), and added with pyridine (Sigma, excess by 2.5 mole times of docetaxcel) before reaction at room temperature for 24 hrs.

Thereafter, the solvent was removed using a rotary evaporator, and the residue was redissolved in DMSO (Sigma), followed by semi-prep HPLC to separate docetaxel-succinate (Su-DTX). A linear gradient of a dual solvent composed of water (+0.05% (v/v) trifluoroacetic acid (TFA, Sigma)) as solvent and 0.05% TFA in acetonitrile (JT Baker) as solvent B (4 mL/min, 30~90% B, 20 minutes) was loaded into a Capcell Pak column (C18, 120 A, 5 um, 10*250, Shiseido). From the HPLC fraction thus obtained, Su-DTX was recovered by lyophilization (yield >70%). In the next step for the activation of Su-DTX, Su-DTX was dissolved, together with EDC (Sigma) and NHS (Sigma), each 2 times mole of Su-DTX, in DMSO (20 mg Su-DTX/mL), and allowed to react with each other at room temperature for 2 hrs. HPLC was carried out in the same manner to separate NHS-DTX, and the final product was recovered through lyophilization (yield >70%).

Figure 3A:
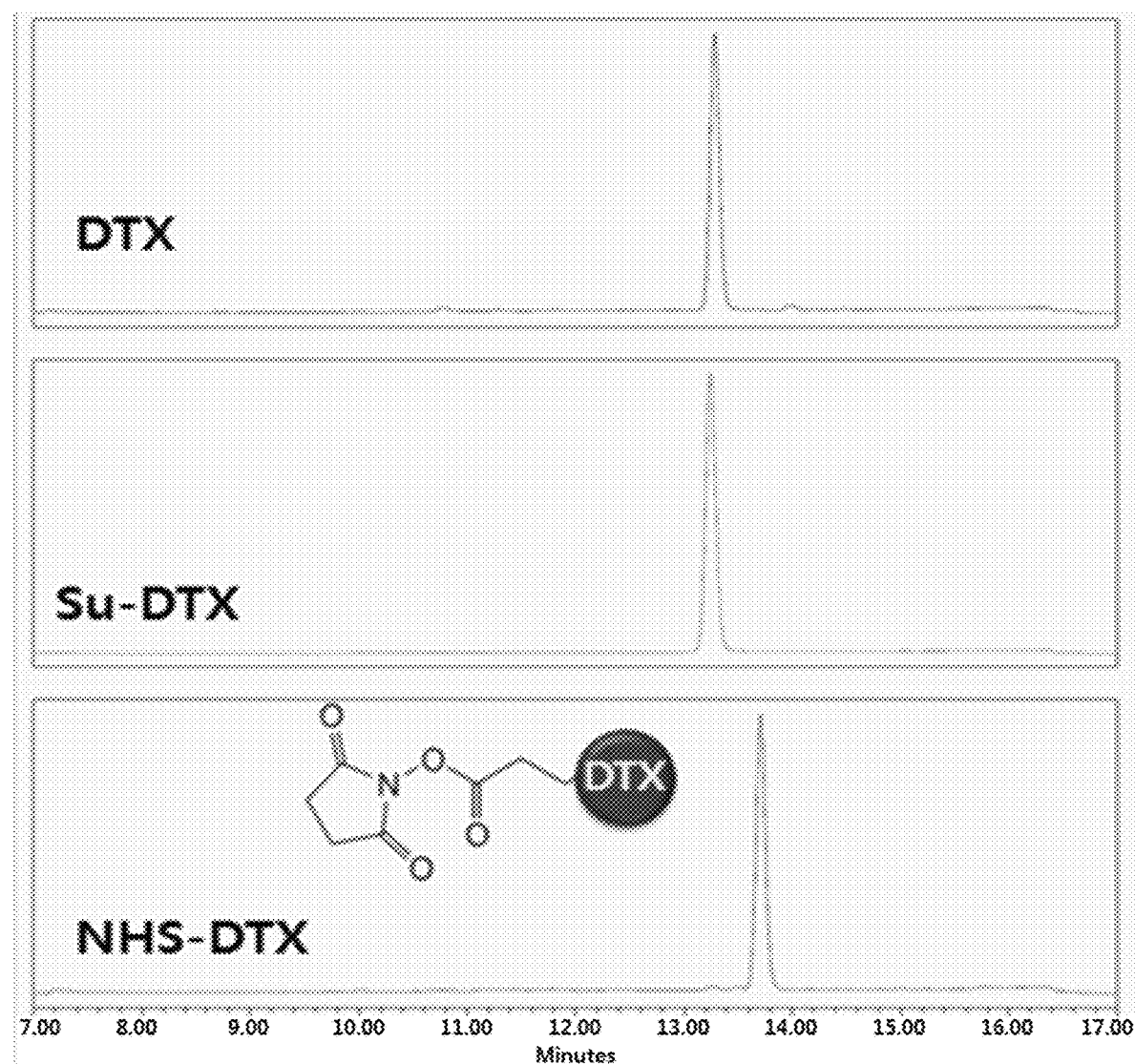
FIGS. 3A and 3B are HPLC chromatograms of docetaxel derivatives.

HPLC data of the docetaxel derivative for amine coupling is given in FIG. 3A. Both the intermediate and the product were found to have a purity of 90% or higher, as analyzed by analytical HPLC (Capcell Pak 4.6*250 column, the same eluent set, 10-90% B, 15 min gradient).

2-2. Derivatization of Docetaxel for Thiol Coupling (FIG. 2, Lower)

A docetaxel derivative for thiol coupling was prepared, in the following 3-step reaction process.

In a first step, docetaxel, Fmoc-Glycine (Sigma), DCC (Sigma) and DMAP (Sigma) were dissolved in equimolar amounts in dichloromethane, and reacted at 4° C. for 2 hrs while stirring, and then at room temperature for an additional 20 hrs. After completion of the reaction, the solvent was removed by vacuum evaporation, and the residue was redissolved in DMSO. By-products were removed from the solution by filtration, and Fmoc-G-DTX was separated in a manner similar to that of Example 2-1.

A second step was of Fmoc deprotection. Fmoc-G-DTX was dissolved to a concentration of 20 mg/mL in DMSO, followed by reaction with 1,8-diazabi-cyclo[5.4.0]undec-7-ene (DBU, Sigma, 1.5 times mole) at room temperature for 5 min. The reaction mixture was isolated and purified using the same HPLC as described above. Finally, NH$_2$-G-DTX and N-(e-maleimidocaproyloxy)succinimide ester (ME-NHS, Thermo), both obtained in the second step, were dissolved in DMSO (20 mg/mL for DTX) at room temperature for 2 hrs, and HPLC was performed in a manner similar to that of Example 2-1. Each reaction step was carried out at a production yield of approximately 70%.

Figure 3B:
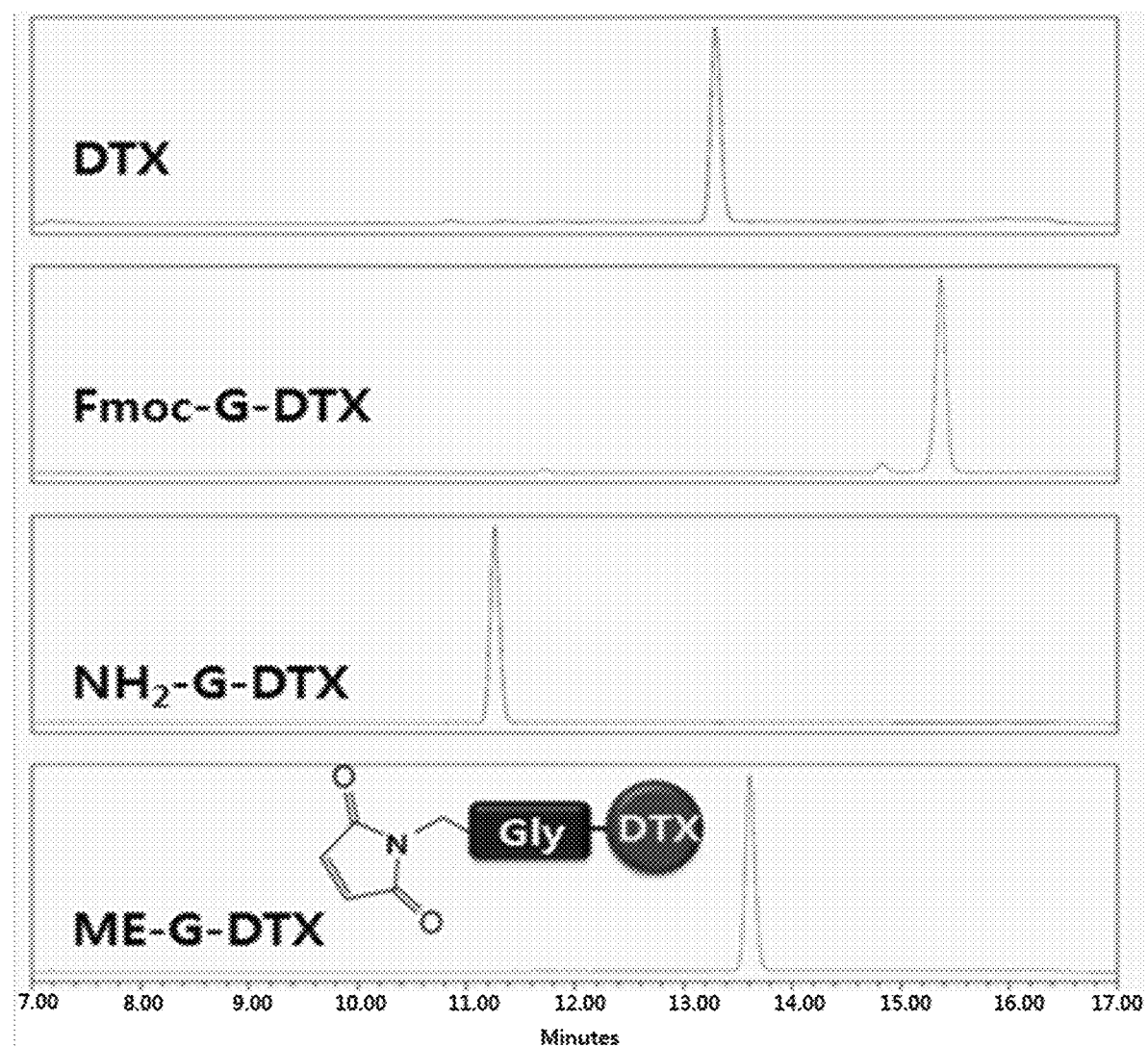

HPLC data of the docetaxel derivative for thiol coupling is given in FIG. 3B. Both the intermediates and the product were found to have a purity of 90% or higher, as analyzed by analytical HPLC (Capcell Pak 4.6*250 column, the same eluent set, 10-90% B, 15 min gradient).

Example 3: Preparation of Antibody-Docetaxel Conjugate 3-1. Preparation of Antibody-Drug Conjugate (ADC1) Through Amine Coupling Referring to the reaction scheme illustrated in FIG. 5, the anti-c-Met antibody L3-1Y/IgG2 prepared in Reference Example 1 was conjugated with a docetaxel derivative for amine coupling, prepared in Example 2-1, to give an antibody-drug conjugate. In this regard, the antibody was used in a fixed amount of 2 mg while the drug was fed at various ratios (feed ratio) of 5 mole times, 10 mole times, 15 mole times, or 20 mole times.

Briefly, NHS-Docetaxel, a docetaxel derivative prepared in Example 2-1, was dissolved at a concentration of 5 mg/ml in DMSO (sigma). The antibody L3-1Y/IgG2 was dissolved to a final concentration of 2 mg/ml in a solution containing 20% DMSO (Sigma), 10 mM CHAPS (Sigma), and 80% PBS (pH 7.4) (Gibco), and fed at a molar ratio of 5, 10, 15 or 20 to the mole of NHS-Docetaxel, followed by reaction at room temperature for 1 hr. Then, only an antibody-docetaxel conjugate was isolated using the Desalting column (GE healthcare) of the AKTA Prime (GE healthcare). To this end, PBS (pH 7.4) was flowed at a rate of 5 ml/min through a desalting column installed in AKTA prime, followed by loading the reaction mixture to the column. The antibody-docetaxel conjugate was separated from docetaxel by size difference.

Figure 6:
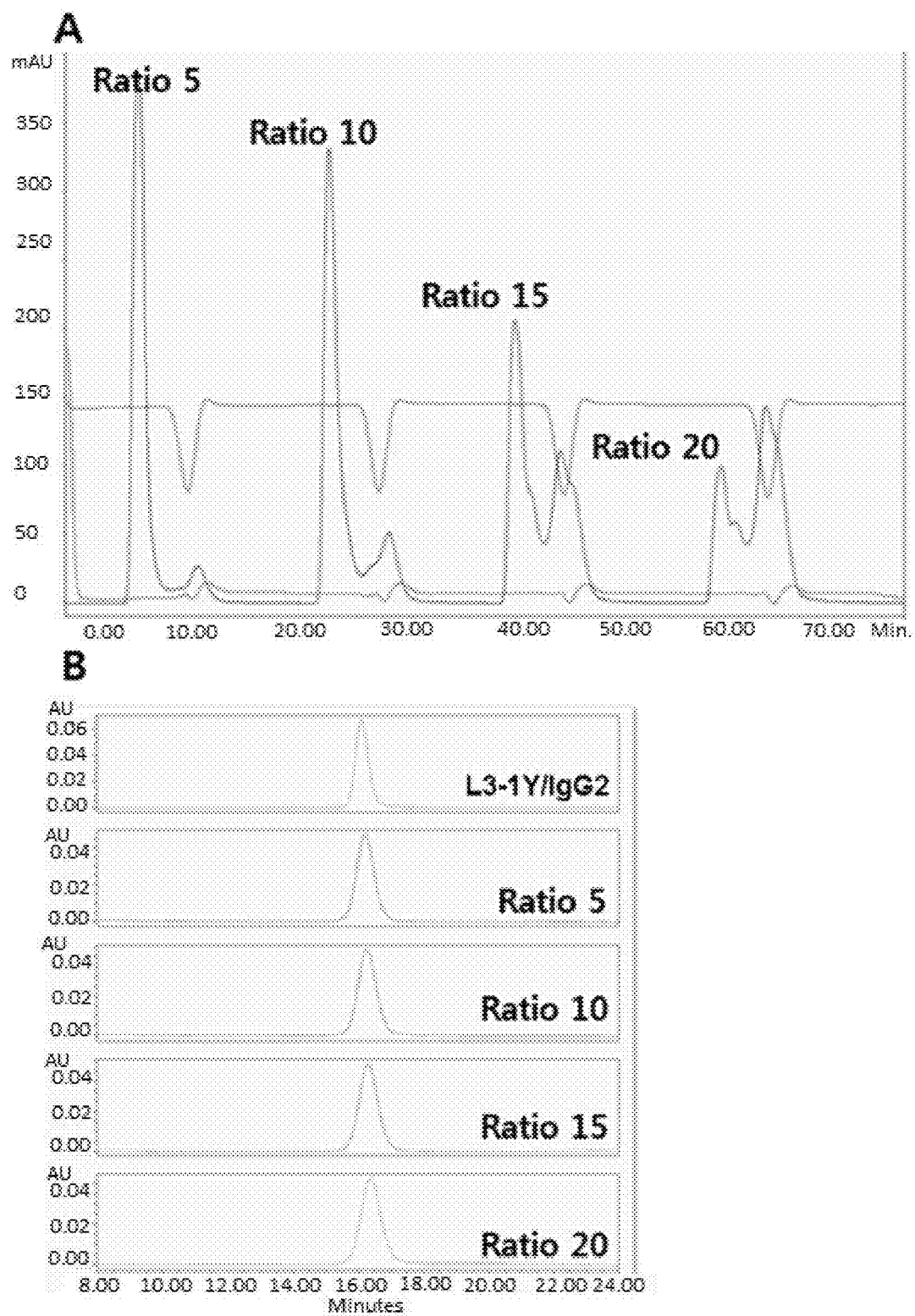
FIG. 6 is a series of HPLC chromatograms of the antibody-drug conjugate (ADC1) prepared through $NH_2$ coupling.

HPLC data of the antibody-drug conjugates prepared with various feed ratios are given in FIG. 6. Recovery rates of the antibody-drug conjugates are listed, together with their DAR (drug-to-antibody ratio), in Table 4, below.

TABLE 4

| Feed Ratio | Ab feed (mg) | Recovery (mg) | DAR | Note |
|---|---|---|---|---|
| 5 | 2 | 1.63 | 4.4 | |
| 10 | 2 | 1.58 | 7.6 | |
| 15 | 2 | 1.18 | — | loss during concentration |
| 20 | 2 | 0.66 | — | loss during concentration |

(DAR:drug-to-antibody ratio)

At a DAR of about 8 or less (corresponding to feed ratio of 10 or less), as can be seen in Table 3, the recovery rates were relatively high, without a loss during concentration.

3-2. Preparation of Antibody-Drug Conjugate (ADC2) Through Thiol Coupling

As illustrated in the reaction scheme of FIG. 7, the anti-c-Met antibody L3-1Y/IgG2 prepared in Reference Example 1 was conjugated with a docetaxel derivative for thiol coupling, prepared in Example 2-1, to give an antibody-drug conjugate. In this regard, the antibody was used in a fixed amount of 2 mg while the drug was fed at various ratios (feed ratio) 2.5, 5, 7.5 or 10 mole times of the antibody.

Briefly, ME-G-Docetaxel, a docetaxel derivative prepared in Example 2-2, was dissolved at a concentration of 5 mg/ml in DMSO (sigma). The antibody L3-1Y/IgG2 was dissolved in excess dithiothreitol (DTT, sigma, 20 times mole), and reacted at 37° C. for 1 hr to reduce the disulfide bond of the antibody. Then, the buffer was changed with PBS (pH 7.4, Gibco) using a desalting column, followed by quantifying the number of reduced thiol using the Ellman reagent 5,5'-dithiobis(2-nitrobenzoic acid)(DTNB, sigma). The reduction was controlled so as to finally obtain 8 thiols/mAb. The antibody was dissolved at a concentration of 2 mg/ml in a solvent mixture containing 20% DMSO (Sigma), 10 mM CHAPS (Sigma), and 80% PBS (pH 7.4) (Gibco) to which the ME-G-Docetaxel solution was then fed at a mole ratio of 2.5, 5, 7.5, 10 to the mole of the antibody, and reacted at 4° C. for 2 hrs. Only the antibody-docetaxel conjugate was purified through a desalting column installed in AKTA Prime.

Figure 8:
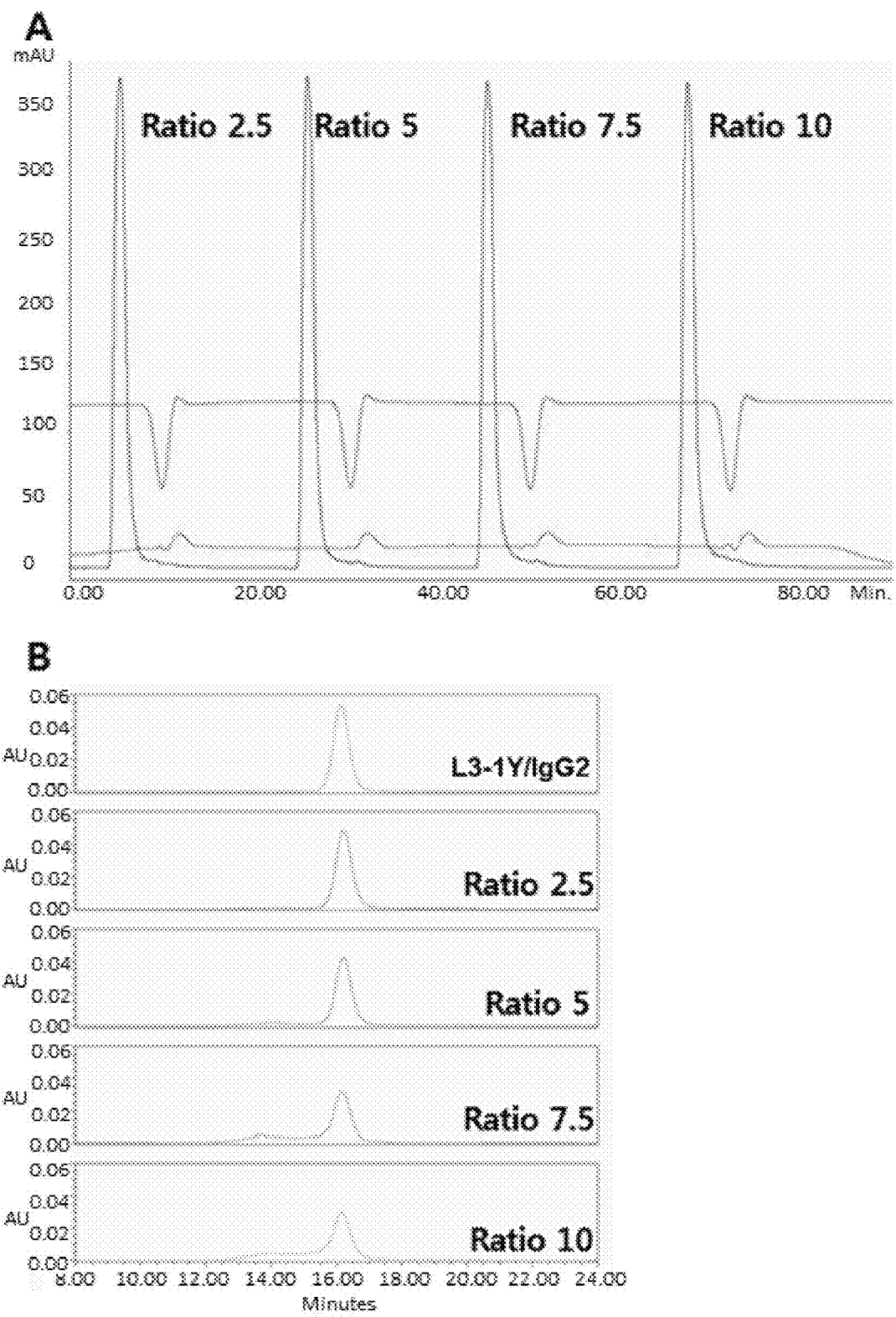
FIG. 8 is a series of HPLC chromatograms of the antibody-drug conjugate (ADC2) prepared through SH coupling.

HPLC data of the antibody-drug conjugates prepared with various feed ratios are given in FIG. 8. Recovery rates of the antibody-drug conjugates are listed, together with their DAR (drug-to-antibody ratio), in Table 5, below.

TABLE 5

| Feed ratio | Ab feed (mg) | Recovery (mg) | DAR | Oligomer (%) |
|---|---|---|---|---|
| 2.5 | 2 | 1.71 | 2.6 | 2.16 |
| 5 | 2 | 1.71 | 5.0 | 10.10 |
| 7.5 | 2 | 1.65 | 7.4 | 21.36 |
| 10 | 2 | 1.75 | 8.4 | 23.37 |

DAR:drug-to-Ab ratio

At a DAR of about 7 or less, e.g., 5, as can be seen in Table 4, purification was achieved at high efficiency because the recovery rates were relatively high with a low level of oligomer production.

3-3. Purification of Antibody-Drug Conjugate

Using the Desalting column (GE healthcare) of AKTA Prime (GE healthcare), only the antibody-docetaxel conjugates were purified. Two desalting columns were tandemly installed in AKTA prime, and then equilibrated with PBS (pH 7.4) which flowed at a rate of 5 ml/min. The reaction mixture was loaded to the columns and separated into antibody-docetaxel conjugates and docetaxel by size difference. Eluates were evaluated for purity HPLC (Waters) using a Sephdex 200 column (Tosoh) and a solvent (20 mM PB (pH 6), 500 mM NaCl, 20% isopropyl alcohol).

Figure 13:
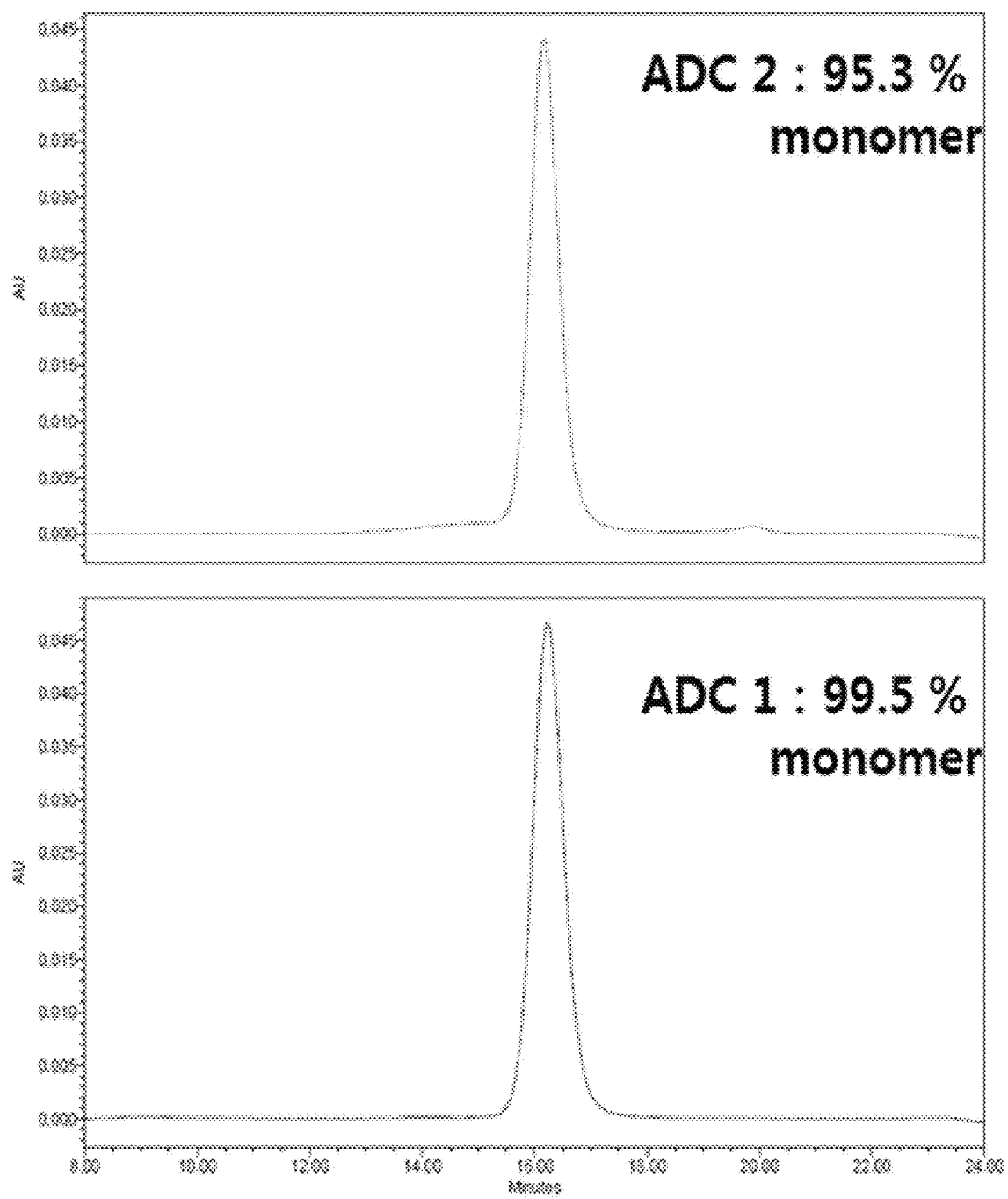
FIG. 13 is a series of SEC-HPLC chromatograms of ADC1 and ADC2.

Results are shown in FIG. 13. As can be seen in FIG. 13, ADC1 (DAR 7.0) and ADC2 (DAR 6.5), prepared in Examples 3-1 and 3-2, respectively, were obtained with a purity of 95% or higher.

Example 4: Affinity of Antibody-Drug Conjugate for Antigen

An examination was made to see whether the antibody-drug conjugates maintain affinity for the antigen. The antibody-drug conjugate (ADC1; amine coupling at a feed molar ratio of 5) was assayed for affinity for the antibody (c-Met) using Biacore T100 (GE), and compared to the antibody alone.

Briefly, a human Fab capture (GE Healthcare) was immobilized on CM5 chip (# BR-1005-30, GE) according to the manufacturer's instruction. Approximately 90~120 RU of ADC was captured, and treated with various concentrations of c-Met-Fc (#358-MT/CF, R&D Systems). The chip was regenerated with 10 mM Glycine-HCl (pH 1.5). To quantify the affinity, the data obtained above was fitted using BIAevaluation software (GE Healthcare, Biacore T100 evaluation software).

The results are shown in Table 6.

TABLE 6

| Sample | Ka * $10^5$ (1/MS) | Kd * $10^{-5}$ (1/s) | KD (pM) | $Chi^2$ |
|---|---|---|---|---|
| L3-1Y/IgG2 | 5.890 | 3.418 | 58.03 | 3.4 |
| ADC (DAR 3.7) | 3.636 | 3.629 | 99.78 | 0.728 |

As can be seen in Table 6, the affinity of ADC for c-Met was approximately 0.1 nM (i.e. 100 pM) (Kd), which is similar to that of the antibody alone. Like this, the antibody even in the form of ADC did not undergo a significant reduction in affinity for antigen, indicating that the conjugate maintains the antibody specificity.

Example 5: Cytotoxicity of Antibody-Drug Conjugate Against c-Met-Positive Cancer Cell ADC1 (DAR 7.0; large batch, feed ratio 10) and ADC2 (DAR 6.5; large batch, feed ratio 7.5) were assayed for cytotoxicity against MKN45 (JCRB0254, JCRB Cell Bank, Japan), a cancer cell line positive to c-Met.

Briefly, the stomach cancer cell line MKN45 was seeded at a density of $10 \times 10^3$ cells/well into 96-well plates (BD) and maintained for 24 hrs. Each ADC was mixed to a desired final antibody concentration (FIG. 9) in a medium, and added to each well. After 72 hrs of incubation, 10 uL of CCK-8 reagent (CK04, Dojindo) was added to each well, and placed at 37° C. for 2.5 hrs in an incubator. Thereafter, absorbance at dual wavelengths (450, 650 nm) was read on a micro-plate reader (Molecular Device).

Figure 9:
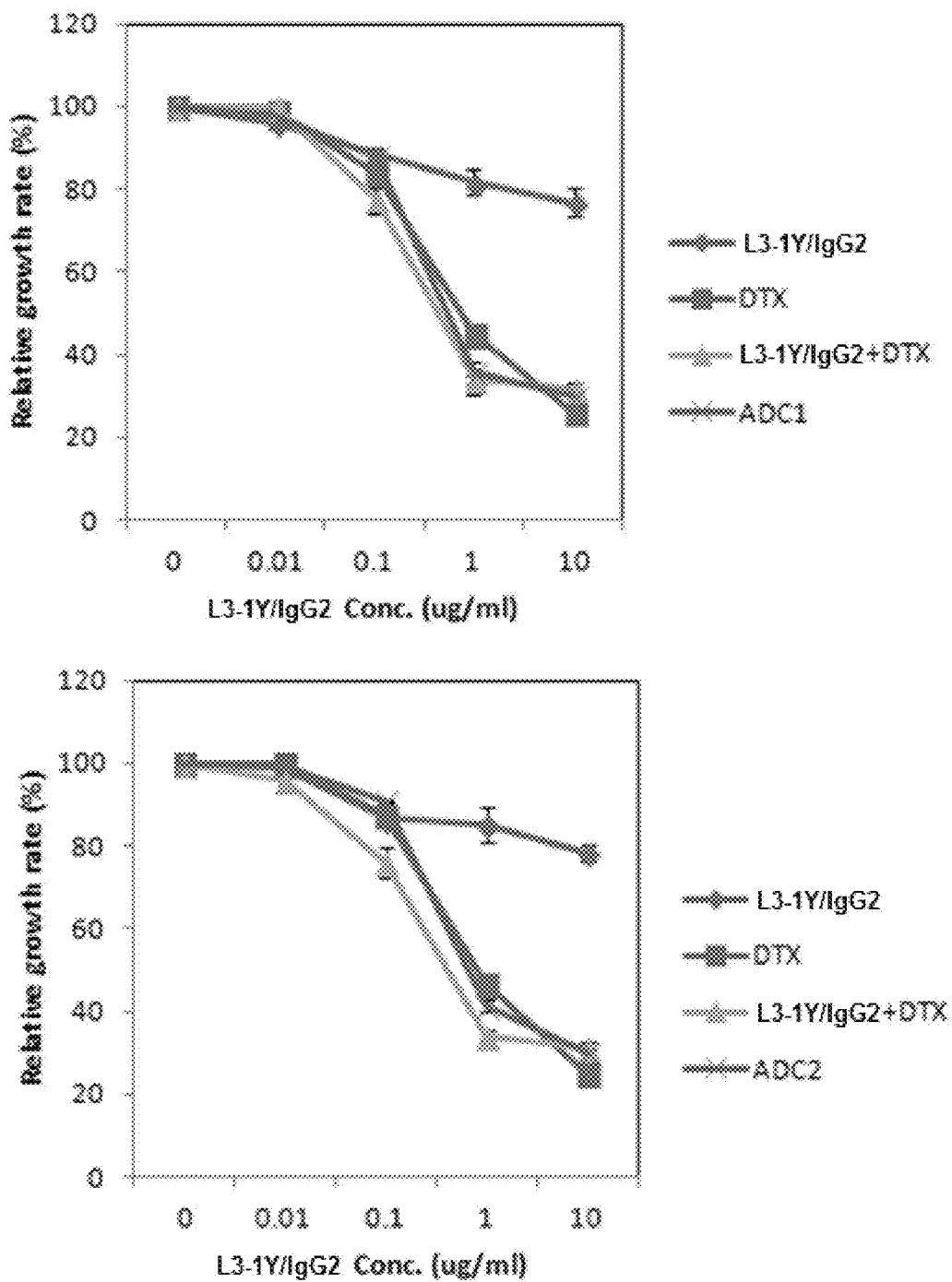
FIG. 9 is a set of graphs depicting relative cell growth rate of a c-Met-positive cancer cell (MKN45) treated with ADC1 or ADC2 indicating the cytotoxicity of ADC1 and ADC2 against the c-Met-positive cancer cell.

Results are shown in FIG. 9. As is apparent from the data of FIG. 9, the anti-c-Met antibody L3-1Y/IgG2 was remarkably increased in cytotoxicity by ADC against c-Met-positive cancer cells, compared to the antibody or the drug alone.

Example 6: Cytotoxicity of Antibody-Drug Conjugate Against Cancer Cell with Anti-c-Met Antibody Serving as Agonist ADC1 (DAR=7.0) and ADC2 (DAR=6.5) were assayed for cytotoxicity against LoVo (CCL-229, ATCC) and HCT116 (CCL-247, ATCC), both cancer cell lines for which the anti-c-Met antibody acts as an agonist.

Briefly, each of the large intestine cancer cell lines LoVo and HCT116 was seeded at a density of $5 \times 10^3$ cells/well into 96-well plates (#353072, BD), and maintained for 24 hrs. Each ADC was mixed to a desired final antibody concentration (FIGS. 11 and 12) in a medium, and added to each well. After 72 hrs of incubation, 10 uL of CCK-8 reagent (CK04, Dojindo) was added to each well, and placed at 37° C. for 2.5 hrs in an incubator. Thereafter, absorbance at dual wavelengths (450, 650 nm) was read on a micro-plate reader (Spectramax 340PC384, Molecular devices).

Figure 10:
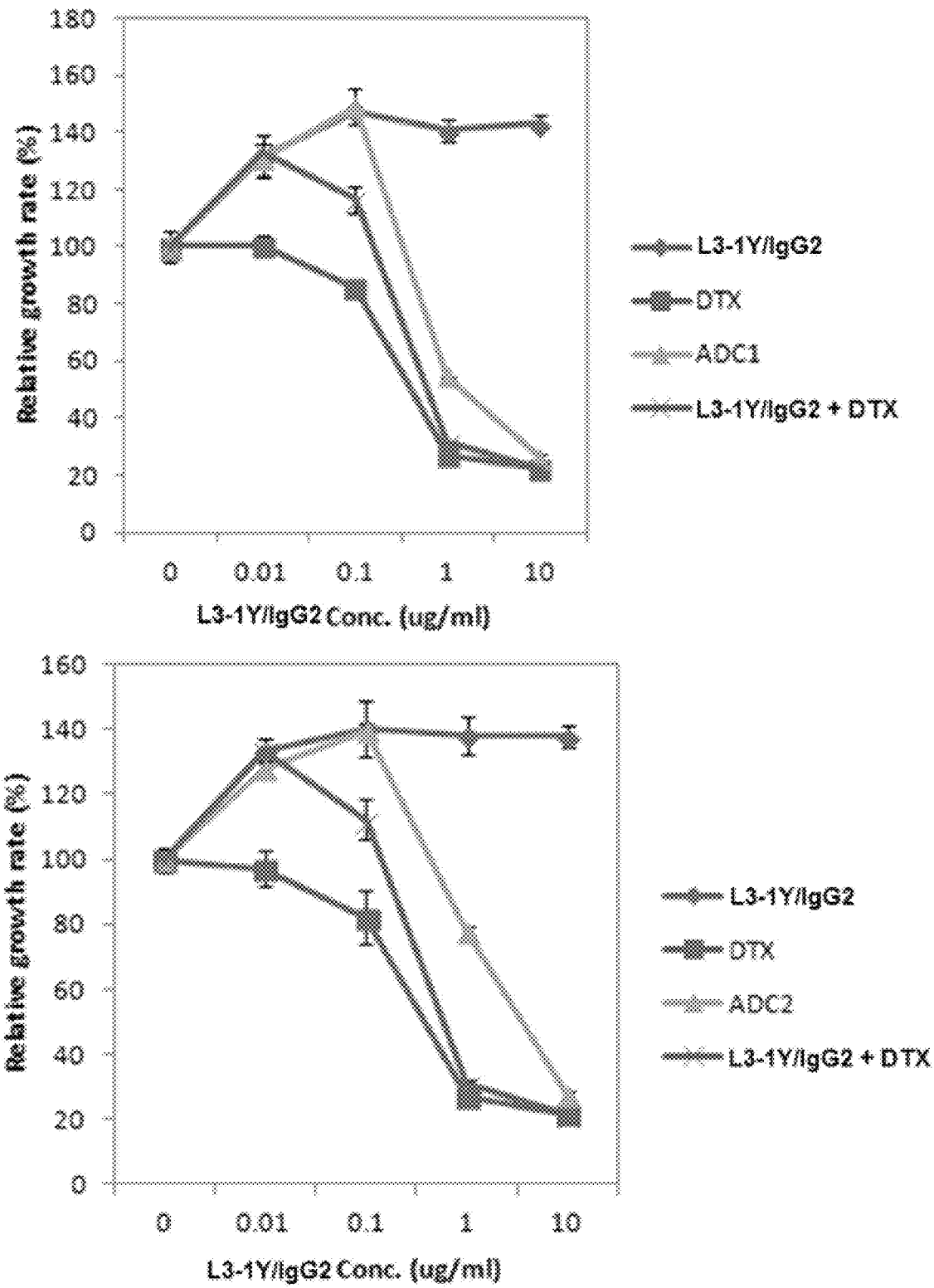
FIG. 10 is a set of graphs depicting relative cell growth rate of LoVo cells to which the anti-c-Met antibody exhibits agonism, when treated with ADC1 or ADC2, indicating the cytotoxicity of ADC1 and ADC2 against LoVo cells.
Figure 11:
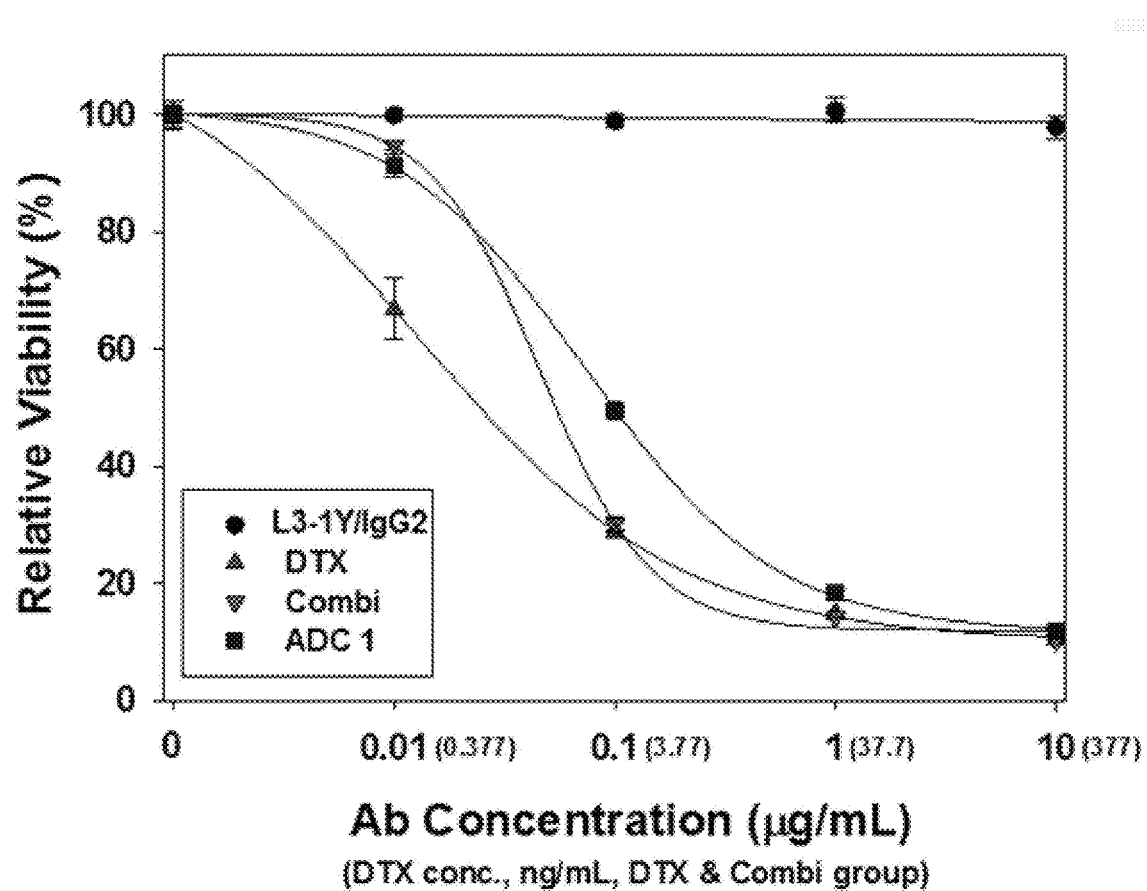
FIG. 11 is a graph showing relative cell viability of cells (HCT116) on which the anti-c-Met antibody alone does not inhibitory effects, but ADC1 does have an inhibitory effect, indicating the cytotoxicity of ADC1 against HCT116 cell.

Results are shown in FIG. 10 (LoVo) and FIG. 11 (HCT116). As is apparent from the data of FIGS. 10 and 11, the anti-c-Met antibody L3-1Y/IgG2 was remarkably increased in cytotoxicity against LoVo, which is resistant to the antibody alone. The data suggest that when conjugated with a drug, the anti-c-Met antibody can expand its inhibition range to the cells on which the anti-c-Met antibody alone has no inhibitory effects.

Example 7: Assay for Hepatotoxicity of Antibody-Drug Conjugate

ADC1 (DAR=7.0) and ADC2 (DAR=6.5) were assayed for hepatotoxicity in human primary hepatocytes (Celsis, F00995, Lot # YEM). For comparison, docetaxel alone or in combination with anti-c-Met antibody was used.

Briefly, human primary hepatocytes were seeded at a density of 30,000 cells/well into collagen I-coated 96-well plates (BD), and maintained for 24 hrs. Then, the cells were treated with L3-1Y/IgG2, docetaxel, ADC1 or ADC2 at a concentration given in FIG. 13 (antibody: 10 ug/ml; docetaxel: 377 ng/ml). For Combi, the cells were incubated in the presence of both 10 ug/ml L3-1Y/IgG2 and 377 ng/ml docetaxel. After 72 hrs of incubation, the cells were applied to Cell Titer Glo (Promega, G7573), and the human primary hepatocytes were counted in each well using the luminescent intensity, and compared to calculate cell viability.

Figure 12:
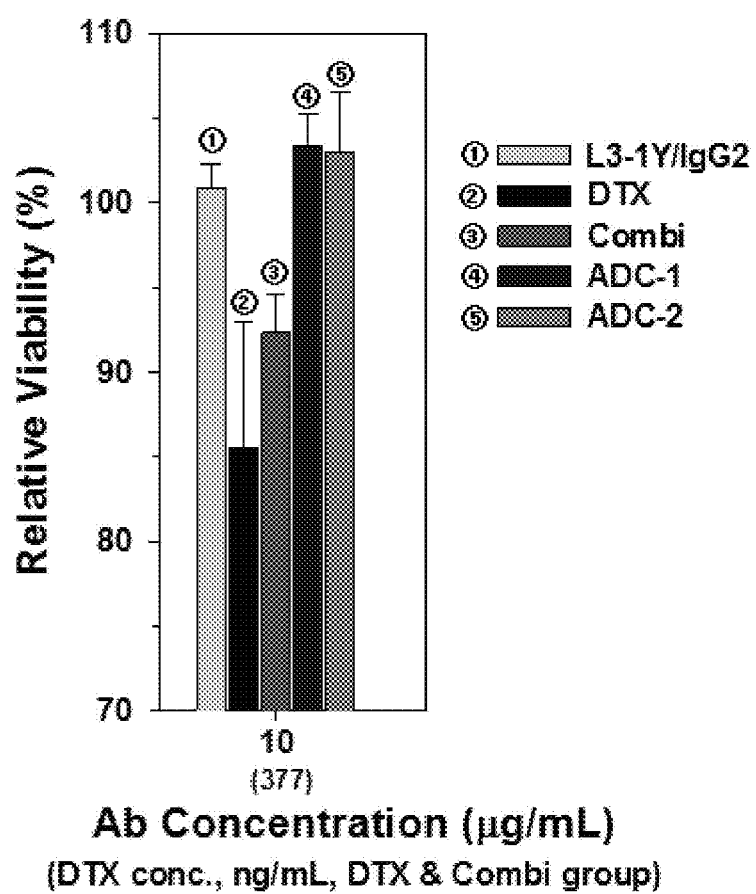
FIG. 12 is a graph showing relative cell viability of human hepatocytes treated with a c-Met antibody, docetaxel, and ADC-1 and ADC-2, indicating the cytotoxicity of the c-Met antibody, docetaxel, and ADC-1 and ADC-2 against human hepatocytes.

The results are given in FIG. 12. As can be seen in FIG. 12, both ADC1 and ADC2 were remarkably low in hepatotoxicity, compared to docetaxel alone or in combination with L3-1Y/IgG2. Considering the fact that the induction of hepatotoxicity is one of the greatest barriers to the use of chemical anticancer agents, such as docetaxel, the antibody-drug conjugate can be more effectively applied to the treatment of cancer not only because of its low hepatotoxicity, compared to a drug alone or in combination with an antibody, but also because of its excellent anticancer activity.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A antibody-drug conjugate comprising an anti-c-Met antibody and a cytotoxic agent, in which the anti-c-Met antibody and the cytotoxic agent are conjugated with each other,
   wherein the anti-c-Met antibody binds to an epitope comprising a sequence of 5 to 19 consecutive amino acids of SEQ ID NO: 71 including the amino acid sequence EEPSQ (SEQ ID NO: 73) and comprises:
   a CDR-H1 comprising the amino acid sequence of SEQ ID NO: 1, 22, 23, or 24;
   a CDR-H2 comprising the amino acid sequence of SEQ ID NO: 2, 25, or 26;
   a CDR-H3 comprising the amino acid sequence of SEQ ID NO: 3, 27, 28, or 85;
   a CDR-L1 comprising the amino acid sequence of SEQ ID NO: 10, 29, 30, 31, 32, 33, or 106;
   a CDR-L2 comprising the amino acid sequence of SEQ ID NO: 11, 34, 35, or 36; and
   a CDR-L3 comprising the amino acid sequence of SEQ ID NO: 13, 14, 15, 16, or 37.

2. The antibody-drug conjugate of claim 1, wherein the cytotoxic agent is at least one selected from the group consisting of maytansine, auristatin based drug, calicheamycin based drug, pyrrolobenzodiazepine based drug, duocarmycin, docetaxel, doxorubicin, carboplatin, cisplatin, cyclophosphamide, ifosfamide, nidran, nitrogen mustard, mechlorethamine HCl, bleomycin, mitomycin C, cytarabine, fluorouracil, gemcitabine, trimetrexate, methotrexate, etoposide, vinblastine, vinorelbine, alimta, altretamine, procarbazine, paclitaxel, taxotere, topotecan, irinotecan, and a radioisotope.

3. The antibody-drug conjugate of claim 1, wherein the cytotoxic agent comprises a functional group capable of forming a chemical bond with the anti-c-Met antibody.

4. The antibody-drug conjugate of claim 2, wherein the cytotoxic agent comprises a functional group capable of forming a chemical bond with the anti-c-Met antibody.

5. The antibody-drug conjugate of claim 4, wherein the functional group is capable of thiol coupling, amine coupling, or reductive amination, with the anti-c-Met antibody.

6. The antibody-drug conjugate of claim 5, wherein the functional group is linked to the cytotoxic agent via a linker, wherein the linker is an amino acid, an amino acid derivative, a peptide comprising 1 to 10 amino acids, a C1-C12 alkyl group, a hydrophilic spacer comprising 1 to 12 ethylene glycol units (—CH2CH2-O—), or a combination thereof.

7. The antibody-drug conjugate of claim 1, wherein the anti-c-Met antibody binds to an epitope of SEQ ID NO: 71, SEQ ID NO: 72, or SEQ ID NO: 73.

8. The antibody-drug conjugate of claim 1, wherein the anti-c-Met antibody comprises:
a CDR-H1 comprising the amino acid sequence of SEQ ID NO: 1; a CDR-H2 comprising the amino acid sequence of SEQ ID NO: 2; a CDR-H3 comprising the amino acid sequence of SEQ ID NO: 3;
a CDR-L1 comprising the amino acid sequence of SEQ ID NO: 10, a CDR-L2 comprising the amino acid sequence of SEQ ID NO: 11; and a CDR-L3 comprising the amino acid sequence of SEQ ID NO: 13, 14, 15, or 16.

9. A method of preparing the antibody-drug conjugate of claim 1, comprising conjugating an anti-c-Met antibody and a cytotoxic agent,
wherein the anti-c-Met antibody binds to an epitope comprising a sequence of 5 to 19 consecutive amino acids of SEQ ID NO: 71 including the amino acid sequence EEPSQ (SEQID NO: 73) and comprises:
a CDR-H1 comprising the amino acid sequence of SEQ ID NO: 1, 22, 23, or 24;
a CDR-H2 comprising the amino acid sequence of SEQ ID NO: 2, 25, or 26;
a CDR-H3 comprising the amino acid sequence of SEQ ID NO: 3, 27, 28, or 85;
a CDR-L1 comprising the amino acid sequence of SEQ ID NO: 10, 29, 30, 31, 32, 33, or 106;
a CDR-L2 comprising the amino acid sequence of SEQ ID NO: 11, 34, 35, or 36; and
a CDR-L3 comprising the amino acid sequence of SEQ ID NO: 13, 14, 15, 16, or 37.

10. The method of claim 9, wherein the anti-c-Met antibody binds to an epitope of SEQ ID NO: 71, SEQ ID NO: 72, or SEQ ID NO: 73.

11. The method of claim 9, wherein the anti-c-Met antibody comprises:
a CDR-H1 comprising the amino acid sequence of SEQ ID NO: 1; a CDR-H2 comprising the amino acid sequence of SEQ ID NO: 2; a CDR-H3 comprising the amino acid sequence of SEQ ID NO: 3;
a CDR-L1 comprising the amino acid sequence of SEQ ID NO: 10, a CDR-L2 comprising the amino acid sequence of SEQ ID NO: 11; and a CDR-L3 comprising the amino acid sequence of SEQ ID NO: 13, 14, 15, or 16.

12. The method of claim 9, wherein the cytotoxic agent is at least one selected from the group consisting of maytansine, auristatin based drug, calicheamycin based drug, pyrrolobenzodiazepine based drug, duocarmycin, docetaxel, doxorubicin, carboplatin, cisplatin, cyclophosphamide, ifosfamide, nidran, nitrogen mustard, mechlorethamine HCl, bleomycin, mitomycin C, cytarabine, fluorouracil, gemcitabine, trimetrexate, methotrexate, etoposide, vinblastine, vinorelbine, alimta, altretamine, procarbazine, paclitaxel, taxotere, topotecan, irinotecan, and a radio-isotope.

13. A method for improving the efficacy of an anti-c-Met antibody, comprising conjugating the anti-c-Met antibody with a cytotoxic agent,
wherein the anti-c-Met antibody binds to an epitope comprising a sequence of 5 to 19 consecutive amino acids of SEQ ID NO: 71 including the amino acid sequence EEPSQ (SEQID NO: 73) and comprises:
a CDR-H1 comprising the amino acid sequence of SEQ ID NO: 1, 22, 23, or 24;
a CDR-H2 comprising the amino acid sequence of SEQ ID NO: 2, 25, or 26;
a CDR-H3 comprising the amino acid sequence of SEQ ID NO: 3, 27, 28, or 85;
a CDR-L1 comprising the amino acid sequence of SEQ ID NO: 10, 29, 30, 31, 32, 33, or 106;
a CDR-L2 comprising the amino acid sequence of SEQ ID NO: 11, 34, 35, or 36; and
a CDR-L3 comprising the amino acid sequence of SEQ ID NO: 13, 14, 15, 16, or 37.

14. The method of claim 13, wherein the anti-c-Met antibody binds to an epitope of SEQ ID NO: 71, SEQ ID NO: 72, or SEQ ID NO: 73.

15. The method of claim 13, wherein the anti-c-Met antibody comprises:
a CDR-H1 comprising the amino acid sequence of SEQ ID NO: 1; a CDR-H2 comprising the amino acid sequence of SEQ ID NO: 2; a CDR-H3 comprising the amino acid sequence of SEQ ID NO: 3;
a CDR-L1 comprising the amino acid sequence of SEQ ID NO: 10, a CDR-L2 comprising the amino acid sequence of SEQ ID NO: 11; and a CDR-L3 comprising the amino acid sequence of SEQ ID NO: 13, 14, 15, or 16.

16. The method of claim 13, wherein the cytotoxic agent is at least one selected from the group consisting of maytansine, auristatin based drug, calicheamycin based drug, pyrrolobenzodiazepine based drug, duocarmycin, docetaxel, doxorubicin, carboplatin, cisplatin, cyclophosphamide, ifosfamide, nidran, nitrogen mustard, mechlorethamine HCl, bleomycin, mitomycin C, cytarabine, fluorouracil, gemcitabine, trimetrexate, methotrexate, etoposide, vinblastine, vinorelbine, alimta, altretamine, procarbazine, paclitaxel, taxotere, topotecan, irinotecan, and a radio-isotope.

* * * * *

SEQUENCE LISTING

<160> NUMBER OF SEQ ID NOS: 108

<210> SEQ ID NO 1
<211> LENGTH: 5
<212> TYPE: PRT
<213> ORGANISM: Artificial Sequence
<220> FEATURE:
<223> OTHER INFORMATION: Synthetic (heavy chain CDR1 of AbF46)

<400> SEQUENCE: 1

Asp Tyr Tyr Met Ser
1               5

<210> SEQ ID NO 2
<211> LENGTH: 19
<212> TYPE: PRT
<213> ORGANISM: Artificial Sequence
<220> FEATURE:
<223> OTHER INFORMATION: Synthetic (heavy chain CDR2 of AbF46)

<400> SEQUENCE: 2

Phe Ile Arg Asn Lys Ala Asn Gly Tyr Thr Thr Glu Tyr Ser Ala Ser
1               5                   10                  15

Val Lys Gly

<210> SEQ ID NO 3
<211> LENGTH: 6
<212> TYPE: PRT
<213> ORGANISM: Artificial Sequence
<220> FEATURE:
<223> OTHER INFORMATION: Synthetic (heavy chain CDR3 of AbF46)

<400> SEQUENCE: 3

Asp Asn Trp Phe Ala Tyr
1               5

<210> SEQ ID NO 4
<211> LENGTH: 6
<212> TYPE: PRT
<213> ORGANISM: Artificial Sequence

```
<220> FEATURE:
<223> OTHER INFORMATION: Synthetic (heavy chain CDR1 of c-Met antibody)
<220> FEATURE:
<221> NAME/KEY: MOD_RES
<222> LOCATION: (1)..(1)
<223> OTHER INFORMATION: Xaa is Pro or Ser or absent
<220> FEATURE:
<221> NAME/KEY: MOD_RES
<222> LOCATION: (2)..(2)
<223> OTHER INFORMATION: Xaa is Glu or Asp

<400> SEQUENCE: 4

Xaa Xaa Tyr Tyr Met Ser
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic (heavy chain CDR2 of c-Met antibody)
<220> FEATURE:
<221> NAME/KEY: MOD_RES
<222> LOCATION: (3)..(3)
<223> OTHER INFORMATION: Xaa is Asn or Lys
<220> FEATURE:
<221> NAME/KEY: MOD_RES
<222> LOCATION: (4)..(4)
<223> OTHER INFORMATION: Xaa is Ala or Val
<220> FEATURE:
<221> NAME/KEY: MOD_RES
<222> LOCATION: (7)..(7)
<223> OTHER INFORMATION: Xaa is Asn or Thr

<400> SEQUENCE: 5

Arg Asn Xaa Xaa Asn Gly Xaa Thr
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic (heavy chain CDR3 of c-Met antibody)
<220> FEATURE:
<221> NAME/KEY: MOD_RES
<222> LOCATION: (5)..(5)
<223> OTHER INFORMATION: Xaa is Ser or Thr

<400> SEQUENCE: 6

Asp Asn Trp Leu Xaa Tyr
1               5

<210> SEQ ID NO 7
<211> LENGTH: 17
<212> TYPE: PRT
<213> ORGANISM: Artificial Sequence
<220> FEATURE:
<223> OTHER INFORMATION: Synthetic (light chain CDR1 of c-Met antibody)
<220> FEATURE:
<221> NAME/KEY: MOD_RES
<222> LOCATION: (4)..(4)
<223> OTHER INFORMATION: Xaa is His, Arg, Gln or Lys
<220> FEATURE:
<221> NAME/KEY: MOD_RES
<222> LOCATION: (9)..(9)
<223> OTHER INFORMATION: Xaa is Ser or Trp
<220> FEATURE:
<221> NAME/KEY: MOD_RES
<222> LOCATION: (12)..(12)
<223> OTHER INFORMATION: Xaa is His or Gln
<220> FEATURE:
<221> NAME/KEY: MOD_RES
```

```
<222> LOCATION: (13)..(13)
<223> OTHER INFORMATION: Xaa is Lys or Asn

<400> SEQUENCE: 7

Lys Ser Ser Xaa Ser Leu Leu Ala Xaa Gly Asn Xaa Xaa Asn Tyr Leu
1               5                   10                  15
Ala

<210> SEQ ID NO 8
<211> LENGTH: 7
<212> TYPE: PRT
<213> ORGANISM: Artificial Sequence
<220> FEATURE:
<223> OTHER INFORMATION: Synthetic (light chain CDR2 of c-Met antibody)
<220> FEATURE:
<221> NAME/KEY: MOD_RES
<222> LOCATION: (2)..(2)
<223> OTHER INFORMATION: Xaa is Ala or Gly
<220> FEATURE:
<221> NAME/KEY: MOD_RES
<222> LOCATION: (4)..(4)
<223> OTHER INFORMATION: Xaa is Thr or Lys
<220> FEATURE:
<221> NAME/KEY: MOD_RES
<222> LOCATION: (7)..(7)
<223> OTHER INFORMATION: Xaa is Ser or Pro

<400> SEQUENCE: 8

Trp Xaa Ser Xaa Arg Val Xaa
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic (light chain CDR3 of c-Met antibody)
<220> FEATURE:
<221> NAME/KEY: MOD_RES
<222> LOCATION: (1)..(1)
<223> OTHER INFORMATION: Xaa is Gly, Ala or Gln
<220> FEATURE:
<221> NAME/KEY: MOD_RES
<222> LOCATION: (6)..(6)
<223> OTHER INFORMATION: Xaa is Arg, His, Ser, Ala, Gly or Lys
<220> FEATURE:
<221> NAME/KEY: MOD_RES
<222> LOCATION: (8)..(8)
<223> OTHER INFORMATION: Xaa is Leu, Tyr, Phe or Met

<400> SEQUENCE: 9

Xaa Gln Ser Tyr Ser Xaa Pro Xaa Thr
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic (light chain CDR1 of AbF46)

<400> SEQUENCE: 10

Lys Ser Ser Gln Ser Leu Leu Ala Ser Gly Asn Gln Asn Asn Tyr Leu
1               5                   10                  15
Ala

<210> SEQ ID NO 11
<211> LENGTH: 7
<212> TYPE: PRT
```

```
<213> ORGANISM: Artificial Sequence
<220> FEATURE:
<223> OTHER INFORMATION: Synthetic (light chain CDR2 of AbF46)

<400> SEQUENCE: 11

Trp Ala Ser Thr Arg Val Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic (light chain CDR3 of AbF46)

<400> SEQUENCE: 12

Gln Gln Ser Tyr Ser Ala Pro Leu Thr
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic (CDR-L3 derived from L3-1 clone)

<400> SEQUENCE: 13

Gln Gln Ser Tyr Ser Arg Pro Tyr Thr
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic (CDR-L3 derived from L3-2 clone)

<400> SEQUENCE: 14

Gly Gln Ser Tyr Ser Arg Pro Leu Thr
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic (CDR-L3 derived from L3-3 clone)

<400> SEQUENCE: 15

Ala Gln Ser Tyr Ser His Pro Phe Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic (CDR-L3 derived from L3-5 clone)

<400> SEQUENCE: 16

Gln Gln Ser Tyr Ser Arg Pro Phe Thr
1               5

<210> SEQ ID NO 17
<211> LENGTH: 117
<212> TYPE: PRT
<213> ORGANISM: Artificial Sequence
```

```
<220> FEATURE:
<223> OTHER INFORMATION: Synthetic (heavy chain variable region of anti
      c-Met humanized antibody(huAbF46-H4))

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gly Thr Leu
            100                 105                 110

Val Thr Val Ser Ser
        115

<210> SEQ ID NO 18
<211> LENGTH: 114
<212> TYPE: PRT
<213> ORGANISM: Artificial Sequence
<220> FEATURE:
<223> OTHER INFORMATION: Synthetic (light chain variable region of anti
      c-Met humanized antibody(huAbF46-H4))

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg

<210> SEQ ID NO 19
<211> LENGTH: 114
<212> TYPE: PRT
<213> ORGANISM: Artificial Sequence
<220> FEATURE:
<223> OTHER INFORMATION: Synthetic (light chain variable region of anti
      c-Met humanized antibody(huAbF46-H4))

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
```

```
                      20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gly Gln
                85                  90                  95

Ser Tyr Ser Arg Pro Leu Thr Phe Gly Gln Gly Thr Lys Val Glu Ile
            100                 105                 110

Lys Arg

<210> SEQ ID NO 20
<211> LENGTH: 114
<212> TYPE: PRT
<213> ORGANISM: Artificial Sequence
<220> FEATURE:
<223> OTHER INFORMATION: Synthetic (light chain variable region of anti
      c-Met humanized antibody(huAbF46-H4))

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Ala Gln
                85                  90                  95

Ser Tyr Ser His Pro Phe Ser Phe Gly Gln Gly Thr Lys Val Glu Ile
            100                 105                 110

Lys Arg

<210> SEQ ID NO 21
<211> LENGTH: 114
<212> TYPE: PRT
<213> ORGANISM: Artificial Sequence
<220> FEATURE:
<223> OTHER INFORMATION: Synthetic (light chain variable region of anti
      c-Met humanized antibody(huAbF46-H4))

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80
```

Ile Ser Ser Leu Gln Pro Glu Asp Phe Ala Thr Tyr Tyr Cys Gln Gln
            85                  90                  95

Ser Tyr Ser Arg Pro Phe Thr Phe Gly Gln Gly Thr Lys Val Glu Ile
        100                 105                 110

Lys Arg

<210> SEQ ID NO 22
<211> LENGTH: 6
<212> TYPE: PRT
<213> ORGANISM: Artificial Sequence
<220> FEATURE:
<223> OTHER INFORMATION: Synthetic (CDR-H1 derived from H11-4 clone)

<400> SEQUENCE: 22

Pro Glu Tyr Tyr Met Ser
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic (CDR-H1 derived from YC151 clone)

<400> SEQUENCE: 23

Pro Asp Tyr Tyr Met Ser
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic (CDR-H1 derived from YC193 clone)

<400> SEQUENCE: 24

Ser Asp Tyr Tyr Met Ser
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic (CDR-H2 derived from YC244 clone)

<400> SEQUENCE: 25

Arg Asn Asn Ala Asn Gly Asn Thr
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic (CDR-H2 derived from YC321 clone)

<400> SEQUENCE: 26

Arg Asn Lys Val Asn Gly Tyr Thr
1               5

<210> SEQ ID NO 27
<211> LENGTH: 6
<212> TYPE: PRT
<213> ORGANISM: Artificial Sequence
<220> FEATURE:

-continued

<223> OTHER INFORMATION: Synthetic (CDR-H3 derived from YC354 clone)

<400> SEQUENCE: 27

Asp Asn Trp Leu Ser Tyr
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic (CDR-H3 derived from YC374 clone)

<400> SEQUENCE: 28

Asp Asn Trp Leu Thr Tyr
1               5

<210> SEQ ID NO 29
<211> LENGTH: 17
<212> TYPE: PRT
<213> ORGANISM: Artificial Sequence
<220> FEATURE:
<223> OTHER INFORMATION: Synthetic (CDR-L1 derived from L1-1 clone)

<400> SEQUENCE: 29

Lys Ser Ser His Ser Leu Leu Ala Ser Gly Asn Gln Asn Asn Tyr Leu
1               5                   10                  15

Ala

<210> SEQ ID NO 30
<211> LENGTH: 17
<212> TYPE: PRT
<213> ORGANISM: Artificial Sequence
<220> FEATURE:
<223> OTHER INFORMATION: Synthetic (CDR-L1 derived from L1-3 clone)

<400> SEQUENCE: 30

Lys Ser Ser Arg Ser Leu Leu Ser Ser Gly Asn His Lys Asn Tyr Leu
1               5                   10                  15

Ala

<210> SEQ ID NO 31
<211> LENGTH: 17
<212> TYPE: PRT
<213> ORGANISM: Artificial Sequence
<220> FEATURE:
<223> OTHER INFORMATION: Synthetic (CDR-L1 derived from L1-4 clone)

<400> SEQUENCE: 31

Lys Ser Ser Lys Ser Leu Leu Ala Ser Gly Asn Gln Asn Asn Tyr Leu
1               5                   10                  15

Ala

<210> SEQ ID NO 32
<211> LENGTH: 17
<212> TYPE: PRT
<213> ORGANISM: Artificial Sequence
<220> FEATURE:
<223> OTHER INFORMATION: Synthetic (CDR-L1 derived from L1-12 clone)

<400> SEQUENCE: 32

Lys Ser Ser Arg Ser Leu Leu Ala Ser Gly Asn Gln Asn Asn Tyr Leu
1               5                   10                  15

Ala

<210> SEQ ID NO 33
<211> LENGTH: 17
<212> TYPE: PRT
<213> ORGANISM: Artificial Sequence
<220> FEATURE:
<223> OTHER INFORMATION: Synthetic (CDR-L1 derived from L1-22 clone)

<400> SEQUENCE: 33

Lys Ser Ser His Ser Leu Leu Ala Ser Gly Asn Gln Asn Asn Tyr Leu
1               5                   10                  15

Ala

<210> SEQ ID NO 34
<211> LENGTH: 7
<212> TYPE: PRT
<213> ORGANISM: Artificial Sequence
<220> FEATURE:
<223> OTHER INFORMATION: Synthetic (CDR-L2 derived from L2-9 clone)

<400> SEQUENCE: 34

Trp Ala Ser Lys Arg Val Ser
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic (CDR-L2 derived from L2-12 clone)

<400> SEQUENCE: 35

Trp Gly Ser Thr Arg Val Ser
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic (CDR-L2 derived from L2-16 clone)

<400> SEQUENCE: 36

Trp Gly Ser Thr Arg Val Pro
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic (CDR-L3 derived from L3-32 clone)

<400> SEQUENCE: 37

Gln Gln Ser Tyr Ser Lys Pro Phe Thr
1               5

<210> SEQ ID NO 38
<211> LENGTH: 1416
<212> TYPE: DNA
<213> ORGANISM: Artificial Sequence
<220> FEATURE:
<223> OTHER INFORMATION: Synthetic (nucleotide sequence of heavy chain
      of chAbF46)
<220> FEATURE:
<221> NAME/KEY: misc_feature
<222> LOCATION: (1)..(6)

<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop codon
<220> FEATURE:
<221> NAME/KEY: misc_feature
<222> LOCATION: (1411)..(1416)
<223> OTHER INFORMATION: XhoI restriction site

<400> SEQUENCE: 38

```
gaattcgccg ccaccatgga atggagctgg gttttctcg taacactttt aaatggtatc      60
cagtgtgagg tgaagctggt ggagtctgga ggaggcttgg tacagcctgg gggttctctg     120
agactctcct gtgcaacttc tgggttcacc ttcactgatt actacatgag ctgggtccgc     180
cagcctccag gaaaggcact tgagtggttg ggttttatta gaaacaaagc taatggttac     240
acaacagagt acagtgcatc tgtgaagggt cggttcacca tctccagaga taattcccaa     300
agcatcctct atcttcaaat ggacaccctg agagctgagg acagtgccac ttattactgt     360
gcaagagata actggtttgc ttactggggc caagggactc tggtcactgt ctctgcagct     420
agcaccaagg gcccatcggt cttccccctg gcaccctcct ccaagagcac ctctggggggc    480
acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagcccaaa     720
tcttgtgaca aaactcacac atgcccaccg tgcccagcac ctgaactcct ggggggaccg     780
tcagtcttcc tcttcccccc aaaacccaag gacaccctca tgatctcccg gaccctgag    840
gtcacatgcg tggtggtgga cgtgagccac gaagaccctg aggtcaagtt caactggtac     900
gtggacggcg tggaggtgca taatgccaag acaaagccgc gggaggagca gtacaacagc     960
acgtaccgtg tggtcagcgt cctcaccgtc ctgcaccagg actggctgaa tggcaaggag    1020
tacaagtgca aggtctccaa caaagccctc ccagccccca tcgagaaaac catctccaaa    1080
gccaaagggc agccccgaga accacaggtg tacaccctgc ccccatcccg ggaggagatg    1140
accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
aagagcctct ccctgtctcc gggtaaatga ctcgag                              1416
```

<210> SEQ ID NO 39
<211> LENGTH: 759

```
<212> TYPE: DNA
<213> ORGANISM: Artificial Sequence
<220> FEATURE:
<223> OTHER INFORMATION: Synthetic (nucleotide sequence of light chain
      of chAbF46)
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 39
gaattcacta gtgattaatt cgccgccacc atggattcac aggcccaggt cctcatgttg      60
ctgctgctat cggtatctgg tacctgtgga gacattttga tgacccagtc tccatcctcc     120
ctgactgtgt cagcaggaga aaggtcact atgagctgca agtccagtca gagtcttta      180 gctagtggca accaaaataa ctacttggcc tggcaccagc agaaaccagg acgatctcct     240
aaaatgctga taatttgggc atccactagg gtatctggag tccctgatcg cttcataggc     300
agtggatctg ggacggattt cactctgacc atcaacagtg tgcaggctga agatctggct     360
gtttattact gtcagcagtc ctacagcgct ccgctcacgt tcggtgctgg gaccaagctg     420
gagctgaaac gtacggtggc tgcaccatct gtcttcatct tcccgccatc tgatgagcag     480
ttgaaatctg gaactgcctc tgttgtgtgc ctgctgaata acttctatcc cagagaggcc     540
aaagtacagt ggaaggtgga taacgccctc caatcgggta actcccagga gagtgtcaca     600
gagcaggaca gcaaggacag cacctacagc ctcagcagca ccctgacgct gagcaaagca     660
gactacgaga aacacaaagt ctacgcctgc gaagtcaccc atcagggcct gagctcgccc     720
gtcacaaaga gcttcaacag gggagagtgt tgactcgag                            759

<210> SEQ ID NO 40
<211> LENGTH: 447
<212> TYPE: PRT
<213> ORGANISM: Artificial Sequence
<220> FEATURE:
<223> OTHER INFORMATION: Synthetic (amino acid sequence of H1-heavy)

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
```

```
                35                  40                  45
Gly Phe Ile Arg Asn Lys Ala Asn Gly Tyr Thr Thr Glu Tyr Ser Ala
 50                  55                  60

Ser Val Lys Gly Arg Phe Thr Ile Ser Arg Asp Asn Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Ala Arg Asp Asn Trp Phe Ala Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 41
```

<211> LENGTH: 447
<212> TYPE: PRT
<213> ORGANISM: Artificial Sequence
<220> FEATURE:
<223> OTHER INFORMATION: Synthetic (amino acid sequence of H3-heavy)

<400> SEQUENCE: 41

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380
```

```
Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Lys
        435                 440                 445

<210> SEQ ID NO 42
<211> LENGTH: 447
<212> TYPE: PRT
<213> ORGANISM: Artificial Sequence
<220> FEATURE:
<223> OTHER INFORMATION: Synthetic (amino acid sequence of H4-heavy)

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300
```

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Arg Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Lys
    435                 440                 445

<210> SEQ ID NO 43
<211> LENGTH: 220
<212> TYPE: PRT
<213> ORGANISM: Artificial Sequence
<220> FEATURE:
<223> OTHER INFORMATION: Synthetic (amino acid sequence of H1-light)

<400> SEQUENCE: 43

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
            85                  90                  95

Ser Tyr Ser Ala Pro Leu Thr Phe Gly Gly Gly Thr Lys Val Glu Ile
        100                 105                 110

Lys Arg Thr Val Ala Ala Pro Ser Val Phe Ile Phe Pro Pro Ser Asp
    115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
        180                 185                 190

Glu Lys His Lys Val Tyr Ala Cys Glu Val Thr His Gln Gly Leu Ser
    195                 200                 205

Ser Pro Val Thr Lys Ser Phe Asn Arg Gly Glu Cys
210                 215                 220

```
<210> SEQ ID NO 44
<211> LENGTH: 220
<212> TYPE: PRT
<213> ORGANISM: Artificial Sequence
<220> FEATURE:
<223> OTHER INFORMATION: Synthetic (amino acid sequence of H2-light)

<400> SEQUENCE: 44
```

Asp Ile Val Met Thr Gln Thr Pro Leu Ser Leu Pro Val Thr Pro Gly
1               5                   10                  15

Glu Pro Ala Ser Ile Ser Cys Lys Ser Ser Gln Ser Leu Leu Ala Ser
            20                  25                  30

Gly Asn Gln Asn Asn Tyr Leu Ala Trp His Leu Gln Lys Pro Gly Gln
        35                  40                  45

Ser Pro Gln Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

Ser Tyr Ser Ala Pro Leu Thr Phe Gly Gln Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

```
<210> SEQ ID NO 45
<211> LENGTH: 220
<212> TYPE: PRT
<213> ORGANISM: Artificial Sequence
<220> FEATURE:
<223> OTHER INFORMATION: Synthetic (amino acid sequence of H3-light)

<400> SEQUENCE: 45
```

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp Tyr Gln Gln Lys Pro Gly Gln
        35                  40                  45

Pro Pro Lys Leu Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln

```
              85                  90                  95
Ser Tyr Ser Ala Pro Leu Thr Phe Gly Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
                210                 215                 220

<210> SEQ ID NO 46
<211> LENGTH: 219
<212> TYPE: PRT
<213> ORGANISM: Artificial Sequence
<220> FEATURE:
<223> OTHER INFORMATION: Synthetic (amino acid sequence of H4-light)

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu
                210                 215
```

```
<210> SEQ ID NO 47
<211> LENGTH: 1350
<212> TYPE: DNA
<213> ORGANISM: Artificial Sequence
<220> FEATURE:
<223> OTHER INFORMATION: Synthetic (nucleotide sequence of H1-heavy)

<400> SEQUENCE: 47
gaggtgcagc tggtggagtc tgggggaggc ttggtccagc ctggagggtc cctgagactc      60
tcctgtgcag cctctggatt caccttcact gactactaca tgagctgggt ccgccaggct     120
ccagggaagg ggctggagtg gttgggcttt attagaaaca agctaacgg ttacaccaca      180 gaatacagtg cgtctgtgaa aggcagattc accatctcaa gagataattc aaagaactca     240
ctgtatctgc aaatgaacag cctgaaaacc gaggacacgg ccgtgtatta ctgtgctaga     300
gataactggt ttgcttactg gggtcaagga accctggtca ccgtctcctc ggctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt      660 gacaaaactc acacatgccc accgtgccca gcacctgaac tcctgggggg accgtcagtc     720
ttcctcttcc ccccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccagcc cccatcgaga aaaccatctc caaagccaaa    1020
gggcagcccc gagaaccaca ggtgtacacc ctgcccccat cccgggagga tgaccaag     1080 aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca agagcaggtg gcagcagggg    1260
aacgtcttct catgctccgt gatgcatgag gctctgcaca accactacac gcagaagagc    1320
ctctccctgt ctccgggtaa atgactcgag                                    1350

<210> SEQ ID NO 48
<211> LENGTH: 1350
<212> TYPE: DNA
<213> ORGANISM: Artificial Sequence
<220> FEATURE:
<223> OTHER INFORMATION: Synthetic (nucleotide sequence of H3-heavy)

<400> SEQUENCE: 48
gaggtgcagc tggtggagtc tgggggaggc ttggtccagc ctggagggtc cctgagactc      60
tcctgtgcag cctctggatt caccttcact gactactaca tgagctgggt ccgccaggct     120
ccagggaagg ggctggagtg gttgggcttt attagaaaca agctaacgg ttacaccaca      180 gaatacagtg cgtctgtgaa aggcagattc accatctcaa gagataattc aaagaactca     240
ctgtatctgc aaatgaacag cctgcgtgct gaggacacgg ccgtgtatta ctgtgctaga     300
gataactggt ttgcttactg gggtcaagga accctggtca ccgtctcctc ggctagcacc     360
aagggcccat cggtcttccc cctggcaccc tcctccaaga gcacctctgg gggcacagcg     420
```

```
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga agttgagcc caaatcttgt     660 gacaaaactc acacatgccc accgtgccca gcacctgaac tcctgggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc cccatcgaga aaaccatctc caaagccaaa   1020
gggcagcccc gagaaccaca ggtgtacacc ctgcccccat cccgggagga gatgaccaag   1080
aaccaggtca gcctgacctg cctggtcaaa ggcttctatc ccagcgacat cgccgtggag   1140
tgggagagca atgggcagcc ggagaacaac tacaagacca cgcctcccgt gctggactcc   1200
gacggctcct tcttcctcta cagcaagctc accgtggaca gagcaggtg gcagcagggg    1260 aacgtcttct catgctccgt gatgcatgag gctctgcaca accactacac gcagaagagc   1320
ctctccctgt ctccgggtaa atgactcgag                                    1350
```

<210> SEQ ID NO 49
<211> LENGTH: 1350
<212> TYPE: DNA
<213> ORGANISM: Artificial Sequence
<220> FEATURE:
<223> OTHER INFORMATION: Synthetic (nucleotide sequence of H4-heavy)

<400> SEQUENCE: 49

```
gaggttcagc tggtggagtc tggcggtggc ctggtgcagc caggggggctc actccgtttg     60 tcctgtgcag cttctggctt caccttcact gattactaca tgagctgggt gcgtcaggcc    120
ccgggtaagg gcctggaatg gttgggtttt attagaaaca agctaatgg ttacacaaca     180 gagtacagtg catctgtgaa gggtcgtttc actataagca gagataattc caaaaacaca    240
ctgtacctgc agatgaacag cctgcgtgct gaggacactg ccgtctatta ttgtgctaga    300
gataactggt ttgcttactg gggccaaggg actctggtca ccgtctcctc ggctagcacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga agttgagcc caaatcttgt     660 gacaaaactc acacatgccc accgtgccca gcacctgaac tcctgggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc cccatcgaga aaaccatctc caaagccaaa   1020
gggcagcccc gagaaccaca ggtgtacacc ctgcccccat cccgggagga gatgaccaag   1080
aaccaggtca gcctgacctg cctggtcaaa ggcttctatc ccagcgacat cgccgtggag   1140
```
tgggagagca atgggcagcc ggagaacaac tacaagacca cgcctcccgt gctggactcc     1200
gacggctcct tcttcctcta cagcaagctc accgtggaca gagcaggtg gcagcagggg     1260 aacgtcttct catgctccgt gatgcatgag gctctgcaca accactacac gcagaagagc     1320 ctctcccctgt ctccgggtaa atgactcgag                                      1350

<210> SEQ ID NO 50
<211> LENGTH: 669
<212> TYPE: DNA
<213> ORGANISM: Artificial Sequence
<220> FEATURE:
<223> OTHER INFORMATION: Synthetic (nucleotide sequence of H1-light)

<400> SEQUENCE: 50
gacatcgtga tgacccagtc tccagactcc ctggctgtgt ctctgggcga gagggccacc       60
atcaactgca gtccagcca gagtcttta gctagcggca ccaaaataa ctacttagct        120 tggcaccagc agaaaccagg acagcctcct aagatgctca tatttgggc atctacccgg       180 gtatccgggg tccctgaccg attcagtggc agcgggtctg ggacagattt cactctcacc       240
atcagcagcc tgcaggctga agatgtggca gtttattact gtcagcaatc ctatagtgct       300
cctctcacgt tcggaggcgg taccaaggtg gagatcaaac gtacggtggc tgcaccatct       360
gtcttcatct tcccgccatc tgatgagcag ttgaaatctg gaactgcctc tgttgtgtgc       420
ctgctgaata acttctatcc cagagaggcc aaagtacagt ggaaggtgga taacgccctc       480
caatcgggta actcccagga gagtgtcaca gagcaggaca gcaaggacag cacctacagc       540
ctcagcagca ccctgacgct gagcaaagca gactacgaga aacacaaagt ctacgcctgc       600
gaagtcaccc atcagggcct gagctcgccc gtcacaaaga gcttcaacag gggagagtgt       660
tgactcgag                                                              669

<210> SEQ ID NO 51
<211> LENGTH: 669
<212> TYPE: DNA
<213> ORGANISM: Artificial Sequence
<220> FEATURE:
<223> OTHER INFORMATION: Synthetic (nucleotide sequence of H2-light)

<400> SEQUENCE: 51
gatattgtga tgacccagac tccactctcc ctgcccgtca cccctggaga gccggcctcc       60
atctcctgca gtccagtca gagtcttta gctagtggca accaaaataa ctacttggcc       120
tggcacctgc agaagccagg gcagtctcca cagatgctga tcatttgggc atccactagg       180
gtatctggag tcccagacag gttcagtggc agtgggtcag gcactgattt cacactgaaa       240
atcagcaggg tggaggctga ggatgttgga gtttattact gccagcagtc ctacagcgct       300
ccgctcacgt tcggacaggg taccaagctg gagctcaaac gtacggtggc tgcaccatct       360
gtcttcatct tcccgccatc tgatgagcag ttgaaatctg gaactgcctc tgttgtgtgc       420
ctgctgaata acttctatcc cagagaggcc aaagtacagt ggaaggtgga taacgccctc       480
caatcgggta actcccagga gagtgtcaca gagcaggaca gcaaggacag cacctacagc       540
ctcagcagca ccctgacgct gagcaaagca gactacgaga aacacaaagt ctacgcctgc       600
gaagtcaccc atcagggcct gagctcgccc gtcacaaaga gcttcaacag gggagagtgt       660
tgactcgag                                                              669

<210> SEQ ID NO 52

<211> LENGTH: 669
<212> TYPE: DNA
<213> ORGANISM: Artificial Sequence
<220> FEATURE:
<223> OTHER INFORMATION: Synthetic (nucleotide sequence of H3-light)

<400> SEQUENCE: 52

| | | | | | |
|---|---|---|---|---|---|
| gacatcgtga | tgacccagtc | tccagactcc | ctggctgtgt | ctctgggcga | gagggccacc | 60 |
| atcaactgca | agtccagcca | gagtcttttta | gctagcggca | accaaaataa | ctacttagct | 120 |
| tggtaccagc | agaaaccagg | acagcctcct | aagctgctca | ttatttgggc | atctacccgg | 180 |
| gtatccgggg | tccctgaccg | attcagtggc | agcgggtctg | ggacagattt | cactctcacc | 240 |
| atcagcagcc | tgcaggctga | agatgtggca | gtttattact | gtcagcaatc | ctatagtgct | 300 |
| cctctcacgt | tcggaggcgg | taccaaggtg | gagatcaaac | gtacggtggc | tgcaccatct | 360 |
| gtcttcatct | tcccgccatc | tgatgagcag | ttgaaatctg | gaactgcctc | tgttgtgtgc | 420 |
| ctgctgaata | acttctatcc | cagagaggcc | aaagtacagt | ggaaggtgga | taacgccctc | 480 |
| caatcgggta | actcccagga | gagtgtcaca | gagcaggaca | gcaaggacag | cacctacagc | 540 |
| ctcagcagca | ccctgacgct | gagcaaagca | gactacgaga | aacacaaagt | ctacgcctgc | 600 |
| gaagtcaccc | atcagggcct | gagctcgccc | gtcacaaaga | gcttcaacag | gggagagtgt | 660 |
| tgactcgag | | | | | | 669 |

<210> SEQ ID NO 53
<211> LENGTH: 669
<212> TYPE: DNA
<213> ORGANISM: Artificial Sequence
<220> FEATURE:
<223> OTHER INFORMATION: Synthetic (nucleotide sequence of H4-light)

<400> SEQUENCE: 53

| | | | | | |
|---|---|---|---|---|---|
| gatatccaga | tgacccagtc | cccgagctcc | ctgtccgcct | ctgtgggcga | tagggtcacc | 60 |
| atcacctgca | agtccagtca | gagtcttttta | gctagtggca | accaaaataa | ctacttggcc | 120 |
| tggcaccaac | agaaaccagg | aaaagctccg | aaaatgctga | ttatttgggc | atccactagg | 180 |
| gtatctggag | tccctctctcg | cttctctgga | tccgggtctg | ggacggattt | cactctgacc | 240 |
| atcagcagtc | tgcagccgga | agacttcgca | acttattact | gtcagcagtc | ctacagcgct | 300 |
| ccgctcacgt | tcggacaggg | taccaaggtg | gagatcaaac | gtacggtggc | tgcaccatct | 360 |
| gtcttcatct | tcccgccatc | tgatgagcag | ttgaaatctg | gaactgcctc | tgttgtgtgc | 420 |
| ctgctgaata | acttctatcc | cagagaggcc | aaagtacagt | ggaaggtgga | taacgccctc | 480 |
| caatcgggta | actcccagga | gagtgtcaca | gagcaggaca | gcaaggacag | cacctacagc | 540 |
| ctcagcagca | ccctgacgct | gagcaaagca | gactacgaga | aacacaaagt | ctacgcctgc | 600 |
| gaagtcaccc | atcagggcct | gagctcgccc | gtcacaaaga | gcttcaacag | gggagagtgt | 660 |
| tgactcgag | | | | | | 669 |

<210> SEQ ID NO 54
<211> LENGTH: 23
<212> TYPE: PRT
<213> ORGANISM: Artificial Sequence
<220> FEATURE:
<223> OTHER INFORMATION: Synthetic (linker between VH and VL)

<400> SEQUENCE: 54

Gly Leu Gly Gly Leu Gly Gly Gly Ser Gly Gly Gly Gly Ser Gly
1               5                   10                  15

Gly Ser Ser Gly Val Gly Ser
           20

<210> SEQ ID NO 55
<211> LENGTH: 1088
<212> TYPE: DNA
<213> ORGANISM: Artificial Sequence
<220> FEATURE:
<223> OTHER INFORMATION: Synthetic (polynucleotide encoding scFv of
      huAbF46 antibody)

<400> SEQUENCE: 55

```
gctagcgttt tagcagaagt tcaattggtt gaatctggtg gtggtttggt tcaaccaggt      60
ggttctttga gattgtcttg tgctgcttct ggttttactt tcaccgatta ttacatgtcc     120
tgggttagac aagctccagg taaaggtttg gaatggttgg gtttcattag aaacaaggct     180
aacggttaca ctaccgaata ttctgcttct gttaagggta gattcaccat ttctagagac     240
aactctaaga caccttgta cttgcaaatg aactccttga gagctgaaga tactgctgtt     300
tattactgcg ctagagataa ttggtttgct tattggggtc aaggtacttt ggttactgtt     360
tcttctggcc tcgggggcct cggaggagga ggtagtggcg gaggaggctc cggtggatcc     420
agcggtgtgg gttccgatat tcaaatgacc caatctccat cttctttgtc tgcttcagtt     480
ggtgatagag ttaccattac ttgtaagtcc tcccaatctt tgttggcttc tggtaatcag     540
aacaattact ggcttggca tcaacaaaaa ccaggtaaag ctccaaagat gttgattatt     600
tgggcttcta ccagagtttc tggtgttcca tctagatttt ctggttctgg ttccggtact     660
gattttactt tgaccatttc atccttgcaa ccagaagatt tcgctactta ctactgtcaa     720
caatcttact ctgctccatt gacttttggt caaggtacaa aggtcgaaat caagagagaa     780
ttcggtaagc ctatccctaa ccctctcctc ggtctcgatt ctacgggtgg tggtggatct     840
ggtggtggtg ttctggtgg tggtggttct caggaactga caactatatg cgagcaaatc     900
ccctcaccaa ctttagaatc gacgccgtac tctttgtcaa cgactactat tttggccaac     960
gggaaggcaa tgcaaggagt ttttgaatat tacaaatcag taacgtttgt cagtaattgc    1020
ggttctcacc cctcaacaac tagcaaaggc agccccataa acacacagta tgttttttga    1080
gtttaaac                                                             1088
```

<210> SEQ ID NO 56
<211> LENGTH: 5597
<212> TYPE: DNA
<213> ORGANISM: Artificial Sequence
<220> FEATURE:
<223> OTHER INFORMATION: Synthetic (expression vector including
      polynucleotide encoding scFv of huAbF46 antibody)
<220> FEATURE:
<221> NAME/KEY: misc_difference
<222> LOCATION: (573)..(578)
<223> OTHER INFORMATION: NheI restriction site
<220> FEATURE:
<221> NAME/KEY: misc_difference
<222> LOCATION: (588)..(938)
<223> OTHER INFORMATION: huAbF46 VH
<220> FEATURE:
<221> NAME/KEY: misc_difference
<222> LOCATION: (939)..(1007)
<223> OTHER INFORMATION: linker
<220> FEATURE:
<221> NAME/KEY: misc_difference
<222> LOCATION: (1008)..(1349)
<223> OTHER INFORMATION: huAbF46 VL
<220> FEATURE:
<221> NAME/KEY: misc_difference
<222> LOCATION: (1350)..(1355)

<223> OTHER INFORMATION: EcoRI restriction site
<220> FEATURE:
<221> NAME/KEY: misc_difference
<222> LOCATION: (1356)..(1397)
<223> OTHER INFORMATION: V5 epitope
<220> FEATURE:
<221> NAME/KEY: misc_difference
<222> LOCATION: (1398)..(1442)
<223> OTHER INFORMATION: (G4S)3 linker
<220> FEATURE:
<221> NAME/KEY: misc_difference
<222> LOCATION: (1443)..(1649)
<223> OTHER INFORMATION: Aga2
<220> FEATURE:
<221> NAME/KEY: misc_difference
<222> LOCATION: (1650)..(1652)
<223> OTHER INFORMATION: TGA(stop codon)
<220> FEATURE:
<221> NAME/KEY: misc_difference
<222> LOCATION: (1653)..(1660)
<223> OTHER INFORMATION: PmeI restriction site

<400> SEQUENCE: 56

```
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agccttattt ctggggtaat taatcagcga agcgatgatt tttgatctat     300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaatac     480
gactcactat agggaatatt aagctaattc tacttcatac attttcaatt aagatgcagt     540
tacttcgctg tttttcaata ttttctgtta ttgctagcgt tttagcagaa gttcaattgg     600
ttgaatctgg tggtggtttg gttcaaccag gtggttcttt gagattgtct tgtgctgctt     660
ctggttttac tttcaccgat tattacatgt cctgggttag acaagctcca ggtaaaggtt     720
tggaatggtt gggtttcatt agaaacaagg ctaacggtta cactaccgaa tattctgctt     780
ctgttaaggg tagattcacc atttctagag acaactctaa gaacaccttg tacttgcaaa     840
tgaactcctt gagagctgaa gatactgctg tttattactg cgctagagat aattggtttg     900
cttattgggg tcaaggtact ttggttactg tttcttctgg cctcggggc tcggaggag       960
gaggtagtgg cggaggaggc tccggtggat ccagcggtgt gggttccgat attcaaatga    1020
cccaatctcc atcttctttg tctgcttcag ttggtgatag agttaccatt acttgtaagt    1080
cctcccaatc tttgttggct tctggtaatc agaacaatta cttggcttgg catcaacaaa    1140
aaccaggtaa agctccaaag atgttgatta tttgggcttc taccagagtt tctggtgttc    1200
catctagatt ttctggttct ggttccggta ctgatttta cttgaccatt tcatccttgc     1260
aaccagaaga tttcgctact tactactgtc aacaatctta ctctgctcca ttgacttttg    1320
gtcaaggtac aaaggtcgaa atcaagagag aattcggtaa gcctatccct aaccctctcc    1380
tcggtctcga ttctacgggt ggtggtggat ctggtggtgg tggttctggt ggtggtggtt    1440
ctcaggaact gacaactata tgcgagcaaa tcccctcacc aactttagaa tcgacgccgt    1500
actctttgtc aacgactact attttggcca acgggaaggc aatgcaagga ttttttgaat    1560
attacaaatc agtaacgttt gtcagtaatt gcggttctca cccctcaaca actagcaaag    1620
gcagccccat aaacacacag tatgtttttt gagtttaaac ccgctgatct gataacaaca    1680
```

```
gtgtagatgt aacaaaatcg actttgttcc cactgtactt ttagctcgta caaaatacaa    1740
tatacttttc atttctccgt aaacaacatg ttttcccatg taatatcctt ttctattttt    1800
cgttccgtta ccaactttac acatacttta tatagctatt cacttctata cactaaaaaa    1860
ctaagacaat tttaattttg ctgcctgcca tatttcaatt tgttataaat tcctataatt    1920
tatcctatta gtagctaaaa aaagatgaat gtgaatcgaa tcctaagaga attgggcaag    1980
tgcacaaaca atacttaaat aaatactact cagtaataac ctatttctta gcattttga     2040 cgaaatttgc tattttgtta gagtctttta caccatttgt ctccacacct ccgcttacat    2100
caacaccaat aacgccattt aatctaagcg catcaccaac attttctggc gtcagtccac    2160
cagctaacat aaaatgtaag ctctcggggc tctcttgcct tccaacccag tcagaaatcg    2220
agttccaatc caaagttca cctgtcccac ctgcttctga atcaaacaag ggaataaacg     2280
aatgaggttt ctgtgaagct gcactgagta gtatgttgca gtcttttgga aatacgagtc    2340
ttttaataac tggcaaaccg aggaactctt ggtattcttg ccacgactca tctccgtgca    2400
gttggacgat atcaatgccg taatcattga ccagagccaa acatcctcc ttaggttgat     2460 tacgaaacac gccaaccaag tatttcggag tgcctgaact atttttatat gcttttacaa    2520
gacttgaaat tttccttgca ataaccgggt caattgttct ctttctattg ggcacacata    2580
taatacccag caagtcagca tcggaatcta gagcacattc tgcggcctct gtgctctgca    2640
agccgcaaac tttcaccaat ggaccagaac tacctgtgaa attaataaca gacatactcc    2700
aagctgcctt tgtgtgctta atcacgtata ctcacgtgct caatagtcac caatgccctc    2760
cctcttggcc ctctcctttt ctttttcga ccgaatttct tgaagacgaa agggcctcgt     2820
gatacgccta ttttatagg ttaatgtcat gataataatg gtttcttagg acggatcgct     2880
tgcctgtaac ttacacgcgc ctcgtatctt ttaatgatgg aataatttgg gaatttactc    2940
tgtgtttatt tattttatg ttttgtattt ggattttaga aagtaaataa agaaggtaga     3000
agagttacgg aatgaagaaa aaaaaataaa caaaggttta aaaaatttca acaaaaagcg    3060
tactttacat atatatttat tagacaagaa aagcagatta aatagatata cattcgatta    3120
acgataagta aaatgtaaaa tcacaggatt ttcgtgtgtg gtcttctaca cagacaagat    3180
gaaacaattc ggcattaata cctgagagca ggaagagcaa gataaaaggt agtatttgtt    3240
ggcgatcccc ctagagtctt ttacatcttc ggaaaacaaa aactattttt tctttaattt    3300 cttttttttac tttctatttt taatttatat atttatatta aaaatttaa attataatta    3360 ttttatagc acgtgatgaa aaggaccag gtggcacttt tcggggaaat gtgcgcggaa      3420
cccctatttg tttatttttc taaatacatt caaatatgta tccgctcatg agacaataac    3480
cctgataaat gcttcaataa tattgaaaaa ggaagagtat gagtattcaa catttccgtg    3540
tcgcccttat tccctttttt gcggcatttt gccttcctgt ttttgctcac ccagaaacgc    3600
tggtgaaagt aaaagatgct gaagatcagt tgggtgcacg agtgggttac atcgaactgg    3660
atctcaacag cggtaagatc cttgagagtt ttcgccccga gaacgttttt ccaatgatga    3720
gcacttttaa agttctgcta tgtggcgcgg tattatcccg tgttgacgcc gggcaagagc    3780
aactcggtcg ccgcatacac tattctcaga atgacttggt tgagtactca ccagtcacag    3840
aaaagcatct tacgatggc atgacagtaa gagaattatg cagtgctgcc ataaccatga    3900
gtgataacac tgcggccaac ttacttctga caacgatcgg aggaccgaag gagctaaccg    3960
cttttttgca acaacatgggg gatcatgtaa ctcgccttga tcgttgggaa ccggagctga    4020
```

| | |
|---|---|
| atgaagccat accaaacgac gagcgtgaca ccacgatgcc tgtagcaatg caacaacgt | 4080 |
| tgcgcaaact attaactggc gaactactta ctctagcttc ccggcaacaa ttaatagact | 4140 |
| ggatggaggc ggataaagtt gcaggaccac ttctgcgctc ggcccttccg gctggctggt | 4200 |
| ttattgctga taaatctgga gccggtgagc gtgggtctcg cggtatcatt gcagcactgg | 4260 |
| ggccagatgg taagccctcc cgtatcgtag ttatctacac gacgggcagt caggcaacta | 4320 |
| tggatgaacg aaatagacag atcgctgaga taggtgcctc actgattaag cattggtaac | 4380 |
| tgtcagacca agtttactca tatatacttt agattgattt aaaacttcat ttttaattta | 4440 |
| aaaggatcta ggtgaagatc cttttttgata atctcatgac caaaatccct taacgtgagt | 4500 |
| tttcgttcca ctgagcgtca gaccccgtag aaaagatcaa aggatcttct tgagatcctt | 4560 |
| tttttctgcg cgtaatctgc tgcttgcaaa caaaaaaacc accgctacca gcggtggttt | 4620 |
| gtttgccgga tcaagagcta ccaactcttt ttccgaaggt aactggcttc agcagagcgc | 4680 |
| agataccaaa tactgtcctt ctagtgtagc cgtagttagg ccaccacttc aagaactctg | 4740 |
| tagcaccgcc tacatacctc gctctgctaa tcctgttacc agtggctgct gccagtggcg | 4800 |
| ataagtcgtg tcttaccggg ttggactcaa gacgatagtt accggataag gcgcagcggt | 4860 |
| cgggctgaac ggggggttcg tgcacacagc ccagcttgga gcgaacgacc tacaccgaac | 4920 |
| tgagatacct acagcgtgag cattgagaaa gcgccacgct tcccgaaggg agaaaggcgg | 4980 |
| acaggtatcc ggtaagcggc agggtcggaa caggagagcg cacgagggag cttccagggg | 5040 |
| ggaacgcctg gtatctttat agtcctgtcg ggtttcgcca cctctgactt gagcgtcgat | 5100 |
| ttttgtgatg ctcgtcaggg gggccgagcc tatggaaaaa cgccagcaac gcggcctttt | 5160 |
| tacggttcct ggccttttgc tggccttttg ctcacatgtt ctttcctgcg ttatcccctg | 5220 |
| attctgtgga taaccgtatt accgcctttg agtgagctga taccgctcgc cgcagccgaa | 5280 |
| cgaccgagcg cagcgagtca gtgagcgagg aagcggaaga gcgcccaata cgcaaaccgc | 5340 |
| ctctccccgc gcgttggccg attcattaat gcagctggca cgacaggttt cccgactgga | 5400 |
| aagcgggcag tgagcgcaac gcaattaatg tgagttacct cactcattag gcaccccagg | 5460 |
| ctttacactt tatgcttccg gctcctatgt tgtgtggaat tgtgagcgga taacaatttc | 5520 |
| acacaggaaa cagctatgac catgattacg ccaagctcgg aattaaccct cactaaaggg | 5580 |
| aacaaaagct ggctagt | 5597 |

```
<210> SEQ ID NO 57
<211> LENGTH: 13
<212> TYPE: PRT
<213> ORGANISM: Artificial Sequence
<220> FEATURE:
<223> OTHER INFORMATION: Synthetic (U6-HC7 hinge)

<400> SEQUENCE: 57

Glu Pro Lys Ser Cys Asp Cys His Cys Pro Pro Cys Pro
1               5                   10

<210> SEQ ID NO 58
<211> LENGTH: 435
<212> TYPE: DNA
<213> ORGANISM: Artificial Sequence
<220> FEATURE:
<223> OTHER INFORMATION: Synthetic (polynucleotide encoding CDR-L3
      derived from L3-1 clone)

<400> SEQUENCE: 58
```

| | |
|---|---|
| gaattcacta gtgattaatt cgccgccacc atggattcac aggcccaggt cctcatgttg | 60 |

```
ctgctgctat cggtatctgg tacctgtgga gatatccaga tgacccagtc cccgagctcc    120
ctgtccgcct ctgtgggcga tagggtcacc atcacctgca agtccagtca gagtctttta    180
gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg ggacggattt cactctgacc atcagcagtc tgcagccgga agacttcgca    360
acttattact gtcagcagtc ctacagccgc cgtacacgt tcggacaggg taccaaggtg    420
gagatcaaac gtacg                                                      435

<210> SEQ ID NO 59
<211> LENGTH: 435
<212> TYPE: DNA
<213> ORGANISM: Artificial Sequence
<220> FEATURE:
<223> OTHER INFORMATION: Synthetic (polynucleotide encoding CDR-L3
      derived from L3-2 clone)

<400> SEQUENCE: 59
gaattcacta gtgattaatt cgccgccacc atggattcac aggcccaggt cctcatgttg     60
ctgctgctat cggtatctgg tacctgtgga gatatccaga tgacccagtc cccgagctcc    120
ctgtccgcct ctgtgggcga tagggtcacc atcacctgca agtccagtca gagtctttta    180
gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg ggacggattt cactctgacc atcagcagtc tgcagccgga agacttcgca    360
acttattact gtgggcagtc ctacagccgt ccgctcacgt tcggacaggg taccaaggtg    420
gagatcaaac gtacg                                                      435

<210> SEQ ID NO 60
<211> LENGTH: 435
<212> TYPE: DNA
<213> ORGANISM: Artificial Sequence
<220> FEATURE:
<223> OTHER INFORMATION: Synthetic (polynucleotide encoding CDR-L3
      derived from L3-3 clone)

<400> SEQUENCE: 60
gaattcacta gtgattaatt cgccgccacc atggattcac aggcccaggt cctcatgttg     60
ctgctgctat cggtatctgg tacctgtgga gatatccaga tgacccagtc cccgagctcc    120
ctgtccgcct ctgtgggcga tagggtcacc atcacctgca agtccagtca gagtctttta    180
gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg ggacggattt cactctgacc atcagcagtc tgcagccgga agacttcgca    360
acttattact gtgcacagtc ctacagccat ccgttctctt tcggacaggg taccaaggtg    420
gagatcaaac gtacg                                                      435

<210> SEQ ID NO 61
<211> LENGTH: 435
<212> TYPE: DNA
<213> ORGANISM: Artificial Sequence
<220> FEATURE:
<223> OTHER INFORMATION: Synthetic (polynucleotide encoding CDR-L3
      derived from L3-5 clone)

<400> SEQUENCE: 61
```

-continued

```
gaattcacta gtgattaatt cgccgccacc atggattcac aggcccaggt cctcatgttg      60
ctgctgctat cggtatctgg tacctgtgga gatatccaga tgacccagtc cccgagctcc     120
ctgtccgcct ctgtgggcga tagggtcacc atcacctgca agtccagtca gagtctttta    180
gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg ggacggattt cactctgacc atcagcagtc tgcagccgga agacttcgca    360
acttattact gtcagcagtc ctacagccgc ccgtttacgt tcggacaggg taccaaggtg    420
gagatcaaac gtacg                                                     435
```

<210> SEQ ID NO 62
<211> LENGTH: 462
<212> TYPE: PRT
<213> ORGANISM: Artificial Sequence
<220> FEATURE:
<223> OTHER INFORMATION: Synthetic (polypeptide consisting of heavy
      chain of huAbF46-H4-A1, U6-HC7 hinge and constant region of
      human IgG1)

<400> SEQUENCE: 62

```
Met Glu Trp Ser Trp Val Phe Leu Val Thr Leu Leu Asn Gly Ile Gln
1               5                   10                  15

Cys Glu Val Gln Leu Val Glu Ser Gly Gly Gly Leu Val Gln Pro Gly
            20                  25                  30

Gly Ser Leu Arg Leu Ser Cys Ala Ala Ser Gly Phe Thr Phe Thr Asp
        35                  40                  45

Tyr Tyr Met Ser Trp Val Arg Gln Ala Pro Gly Lys Gly Leu Glu Trp
    50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Cys His
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270
```

```
Glu Val Thr Cys Val Val Val Asp Val Ser His Glu Asp Pro Glu Val
            275                 280                 285
Lys Phe Asn Trp Tyr Val Asp Gly Val Glu Val His Asn Ala Lys Thr
        290                 295                 300
Lys Pro Arg Glu Glu Gln Tyr Asn Ser Thr Tyr Arg Val Val Ser Val
305                 310                 315                 320
Leu Thr Val Leu His Gln Asp Trp Leu Asn Gly Lys Glu Tyr Lys Cys
                325                 330                 335
Lys Val Ser Asn Lys Ala Leu Pro Ala Pro Ile Glu Lys Thr Ile Ser
            340                 345                 350
Lys Ala Lys Gly Gln Pro Arg Glu Pro Gln Val Tyr Thr Leu Pro Pro
        355                 360                 365
Ser Arg Glu Glu Met Thr Lys Asn Gln Val Ser Leu Thr Cys Leu Val
370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Pro Val Leu Asp Ser Asp
                405                 410                 415
Gly Ser Phe Phe Leu Tyr Ser Lys Leu Thr Val Asp Lys Ser Arg Trp
            420                 425                 430
Gln Gln Gly Asn Val Phe Ser Cys Ser Val Met His Glu Ala Leu His
        435                 440                 445
Asn His Tyr Thr Gln Lys Ser Leu Ser Leu Ser Pro Gly Lys
450                 455                 460

<210> SEQ ID NO 63
<211> LENGTH: 1410
<212> TYPE: DNA
<213> ORGANISM: Artificial Sequence
<220> FEATURE:
<223> OTHER INFORMATION: Synthetic (polynucleotide encoding polypeptide
      consisting of heavy chain of huAbF46-H4-A1, U6-HC7 hinge
      and constant region of human IgG1)

<400> SEQUENCE: 63
gaattcgccg ccaccatgga atggagctgg gttttttctcg taacactttt aaatggtatc    60
cagtgtgagg ttcagctggt ggagtctggc ggtggcctgg tgcagccagg gggctcactc   120
cgtttgtcct gtgcagcttc tggcttcacc ttcactgatt actacatgag ctgggtgcgt   180
caggccccgg gtaagggcct ggaatggttg ggttttatta gaaacaaagc taatggttac   240
acaacagagt acagtgcatc tgtgaagggt cgtttcacta taagcagaga taattccaaa   300
aacacactgt acctgcagat gaacagcctg cgtgctgagg acactgccgt ctattattgt   360
gctagagata actggtttgc ttactgggcc aagggactct ggtcaccgtc tcctcggct    420 agcaccaagg gcccatcggt cttccccctg gcaccctcct ccaagagcac ctctggggc    480 acagcggccc tgggctgcct ggtcaaggac tacttccccg aaccggtgac ggtgtcgtgg   540
aactcaggcg ccctgaccag cggcgtgcac accttcccgg ctgtcctaca gtcctcagga   600
ctctactccc tcagcagcgt ggtgaccgtg ccctccagca gcttgggcac ccagacctac   660
atctgcaacg tgaatcacaa gcccagcaac accaaggtgg acaagaaagt tgagcccaaa   720
agctgcgatt gccactgtcc tccatgtcca gcacctgaac tcctgggggg accgtcagtc   780
ttcctcttcc cccaaaaacc caaggacacc ctcatgatct cccggacccc tgaggtcaca   840
tgcgtggtgg tggacgtgag ccacgaagac cctgaggtca agttcaactg gtacgtggac   900
```

```
ggcgtggagg tgcataatgc aagacaaag ccgcggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgcccccat cccgggagga gatgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta cagcaagctc accgtggaca agagcaggtg gcagcagggg   1320
aacgtcttct catgctccgt gatgcatgag gctctgcaca accactacac gcagaagagc   1380
ctctccctgt ctccgggtaa atgactcgag                                   1410
```

<210> SEQ ID NO 64
<211> LENGTH: 461
<212> TYPE: PRT
<213> ORGANISM: Artificial Sequence
<220> FEATURE:
<223> OTHER INFORMATION: Synthetic (polypeptide consisting of heavy
      chain of huAbF46-H4-A1, human IgG2 hinge and constant region of
      human IgG1)

<400> SEQUENCE: 64

```
Met Glu Trp Ser Trp Val Phe Leu Val Thr Leu Leu Asn Gly Ile Gln
1               5                   10                  15

Cys Glu Val Gln Leu Val Glu Ser Gly Gly Leu Val Gln Pro Gly
            20                  25                  30

Gly Ser Leu Arg Leu Ser Cys Ala Ala Ser Gly Phe Thr Phe Thr Asp
        35                  40                  45

Tyr Tyr Met Ser Trp Val Arg Gln Ala Pro Gly Lys Gly Leu Glu Trp
    50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Arg Lys Cys Cys Val Glu Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
```

```
                260             265             270
Val Thr Cys Val Val Asp Val Ser His Glu Asp Pro Glu Val Lys
        275             280             285

Phe Asn Trp Tyr Val Asp Gly Val Glu Val His Asn Ala Lys Thr Lys
        290             295             300

Pro Arg Glu Glu Gln Tyr Asn Ser Thr Tyr Arg Val Val Ser Val Leu
305             310             315             320

Thr Val Leu His Gln Asp Trp Leu Asn Gly Lys Glu Tyr Lys Cys Lys
                325             330             335

Val Ser Asn Lys Ala Leu Pro Ala Pro Ile Glu Lys Thr Ile Ser Lys
        340             345             350

Ala Lys Gly Gln Pro Arg Glu Pro Gln Val Tyr Thr Leu Pro Pro Ser
        355             360             365

Arg Glu Glu Met Thr Lys Asn Gln Val Ser Leu Thr Cys Leu Val Lys
        370             375             380

Gly Phe Tyr Pro Ser Asp Ile Ala Val Glu Trp Glu Ser Asn Gly Gln
385             390             395             400

Pro Glu Asn Asn Tyr Lys Thr Thr Pro Pro Val Leu Asp Ser Asp Gly
                405             410             415

Ser Phe Phe Leu Tyr Ser Lys Leu Thr Val Asp Lys Ser Arg Trp Gln
                420             425             430

Gln Gly Asn Val Phe Ser Cys Ser Val Met His Glu Ala Leu His Asn
        435             440             445

His Tyr Thr Gln Lys Ser Leu Ser Leu Ser Pro Gly Lys
        450             455             460

<210> SEQ ID NO 65
<211> LENGTH: 1407
<212> TYPE: DNA
<213> ORGANISM: Artificial Sequence
<220> FEATURE:
<223> OTHER INFORMATION: Synthetic (polynucleotide encoding polypeptide
      consisting of heavy chain of huAbF46-H4-A1, human IgG2
      hinge and constant region of human IgG1

<400> SEQUENCE: 65
gaattcgccg ccaccatgga atggagctgg gttttttctcg taacactttt aaatggtatc      60
cagtgtgagg ttcagctggt ggagtctggc ggtggcctgg tgcagccagg ggctcactc     120 cgtttgtcct gtgcagcttc tggcttcacc ttcactgatt actacatgag ctgggtgcgt     180
caggccccgg gtaagggcct ggaatggttg ggttttatta gaaacaaagc taatggttac     240
acaacagagt acagtgcatc tgtgaagggt cgtttcacta agcagaga taattccaaa     300 aacacactgt acctgcagat gaacagcctg cgtgctgagg acactgccgt ctattattgt     360
gctagagata actggtttgc ttactggggc caagggactc tggtcaccgt ctcctcggct     420
agcaccaagg gcccatcggt cttccccctg gcaccctcct ccaagagcac ctctgggggc     480
acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagaggaag     720
tgctgtgtgg agtgcccccc ctgcccagca cctgaactcc tggggggacc gtcagtcttc     780
ctcttccccc caaaacccaa ggacaccctc atgatctccc ggaccccct ga ggtcacatgc     840 gtggtggtgg acgtgagcca cgaagaccct gaggtcaagt tcaactggta cgtggacggc     900
```

```
gtggaggtgc ataatgccaa gacaaagccg cgggaggagc agtacaacag cacgtaccgt    960
gtggtcagcg tcctcaccgt cctgcaccag gactggctga atggcaagga gtacaagtgc   1020
aaggtctcca acaaagccct cccagccccc atcgagaaaa ccatctccaa agccaaggg    1080 cagccccgag aaccacaggt gtacaccctg cccccatccc gggaggagat gaccaagaac   1140
caggtcagcc tgacctgcct ggtcaaaggc ttctatccca gcgacatcgc cgtggagtgg   1200
gagagcaatg ggcagccgga gaacaactac aagaccacgc ctcccgtgct ggactccgac   1260
ggctccttct tcctctacag caagctcacc gtggacaaga gcaggtggca gcaggggaac   1320
gtcttctcat gctccgtgat gcatgaggct ctgcacaacc actacacgca gaagagcctc   1380
tccctgtctc cgggtaaatg actcgag                                       1407
```

<210> SEQ ID NO 66
<211> LENGTH: 460
<212> TYPE: PRT
<213> ORGANISM: Artificial Sequence
<220> FEATURE:
<223> OTHER INFORMATION: Synthetic (polypeptide consisting of heavy
      chain of huAbF46-H4-A1, human IgG2 hinge and constant region
      of human IgG2)

<400> SEQUENCE: 66

```
Met Glu Trp Ser Trp Val Phe Leu Val Thr Leu Leu Asn Gly Ile Gln
1               5                   10                  15

Cys Glu Val Gln Leu Val Glu Ser Gly Gly Gly Leu Val Gln Pro Gly
            20                  25                  30

Gly Ser Leu Arg Leu Ser Cys Ala Ala Ser Gly Phe Thr Phe Thr Asp
        35                  40                  45

Tyr Tyr Met Ser Trp Val Arg Gln Ala Pro Gly Lys Gly Leu Glu Trp
    50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Asn Phe Gly Thr Gln Thr Tyr Thr Cys Asn Val Asp His Lys Pro Ser
    210                 215                 220

Asn Thr Lys Val Asp Lys Thr Val Glu Arg Lys Cys Cys Val Glu Cys
225                 230                 235                 240

Pro Pro Cys Pro Ala Pro Pro Val Ala Gly Pro Ser Val Phe Leu Phe
                245                 250                 255
```

```
Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Gln Phe
        275                 280                 285

Asn Trp Tyr Val Asp Gly Val Glu Val His Asn Ala Lys Thr Lys Pro
        290                 295                 300

Arg Glu Glu Gln Phe Asn Ser Thr Phe Arg Val Val Ser Val Leu Thr
305                 310                 315                 320

Val Val His Gln Asp Trp Leu Asn Gly Lys Glu Tyr Lys Cys Lys Val
                325                 330                 335

Ser Asn Lys Gly Leu Pro Ala Pro Ile Glu Lys Thr Ile Ser Lys Thr
            340                 345                 350

Lys Gly Gln Pro Arg Glu Pro Gln Val Tyr Thr Leu Pro Pro Ser Arg
        355                 360                 365

Glu Glu Met Thr Lys Asn Gln Val Ser Leu Thr Cys Leu Val Lys Gly
        370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Met Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
        450                 455                 460
```

<210> SEQ ID NO 67
<211> LENGTH: 1404
<212> TYPE: DNA
<213> ORGANISM: Artificial Sequence
<220> FEATURE:
<223> OTHER INFORMATION: Synthetic (polynucleotide encoding polypeptide
      consisting of heavy chain of huAbF46-H4-A1, human
      IgG2 hinge and constant region of human IgG2)

<400> SEQUENCE: 67

```
gaattcgccg ccaccatgga atggagctgg gttttctcg taacactttt aaatggtatc    60
cagtgtgagg ttcagctggt ggagtctggc ggtggcctgg tgcagccagg gggctcactc   120
cgtttgtcct gtgcagcttc tggcttcacc ttcactgatt actacatgag ctgggtgcgt   180
caggccccgg gtaagggcct ggaatggttg ggttttatta gaaacaaagc taatggttac   240
acaacagagt acagtgcatc tgtgaagggt cgtttcacta taagcagaga taattccaaa   300
aacacactgt acctgcagat gaacagcctg cgtgctgagg acactgccgt ctattattgt   360
gctagagata actggtttgc ttactggggc caagggactc tggtcaccgt ctcctcggct   420
agcaccaagg gcccatcggt cttccccctg gcgccctgct ccaggagcac ctccgagagc   480
acagcggccc tgggctgcct ggtcaaggac tacttccccg aaccggtgac ggtgtcgtgg   540
aactcaggcg ctctgaccag cggcgtgcac accttcccag ctgtcctaca gtcctcagga   600
ctctactccc tcagcagcgt ggtgaccgtg ccctccagca acttcggcac ccagacctac   660
acctgcaacg tagatcacaa gcccagcaac accaaggtgg acaagacagt tgagcgcaaa   720
tgttgtgtcg agtgcccacc gtgcccagca ccacctgtgg caggaccgtc agtcttcctc   780
ttccccccaa aacccaagga caccctcatg atctcccgga cccctgaggt cacgtgcgtg   840
```

```
gtggtggacg tgagccacga agaccccgag gtccagttca actggtacgt ggacggcgtg    900
gaggtgcata tgccaagac aaagccacgg gaggagcagt tcaacagcac gttccgtgtg     960
gtcagcgtcc tcaccgttgt gcaccaggac tggctgaacg gcaaggagta caagtgcaag   1020
gtctccaaca aaggcctccc agcccccatc gagaaaacca tctccaaaac caaagggcag   1080
ccccgagaac acaggtgta caccctgccc ccatcccggg aggagatgac caagaaccag    1140
gtcagcctga cctgcctggt caaaggcttc taccccagcg acatcgccgt ggagtgggag   1200
agcaatgggc agccggagaa caactacaag accacgcctc ccatgctgga ctccgacggc   1260
tccttcttcc tctacagcaa gctcaccgtg gacaagagca ggtggcagca ggggaacgtc   1320
ttctcatgct ccgtgatgca tgaggctctg cacaaccact acacgcagaa gagcctctcc   1380
ctgtctccgg gtaaatgact cgag                                          1404
```

<210> SEQ ID NO 68
<211> LENGTH: 240
<212> TYPE: PRT
<213> ORGANISM: Artificial Sequence
<220> FEATURE:
<223> OTHER INFORMATION: Synthetic (polypeptide consisting of light
      chain of huAbF46-H4-A1(H36Y) and human kappa constant region)

<400> SEQUENCE: 68

```
Met Asp Ser Gln Ala Gln Val Leu Met Leu Leu Leu Leu Ser Val Ser
1               5                   10                  15

Gly Thr Cys Gly Asp Ile Gln Met Thr Gln Ser Pro Ser Ser Leu Ser
            20                  25                  30

Ala Ser Val Gly Asp Arg Val Thr Ile Thr Cys Lys Ser Ser Gln Ser
        35                  40                  45

Leu Leu Ala Ser Gly Asn Gln Asn Asn Tyr Leu Ala Trp Tyr Gln Gln
    50                  55                  60

Lys Pro Gly Lys Ala Pro Lys Met Leu Ile Ile Trp Ala Ser Thr Arg
65                  70                  75                  80

Val Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 69
<211> LENGTH: 758

<212> TYPE: DNA
<213> ORGANISM: Artificial Sequence
<220> FEATURE:
<223> OTHER INFORMATION: Synthetic (polynucleotide encoding polypeptide
consisting of light chain of huAbF46-H4-A1(H36Y) and
human kappa constant region)

<400> SEQUENCE: 69

```
aattcactag tgattaattc gccgccacca tggattcaca ggcccaggtc ctcatgttgc    60
tgctgctatc ggtatctggt acctgtggag atatccagat gacccagtcc ccgagctccc   120
tgtccgcctc tgtgggcgat agggtcacca tcacctgcaa gtccagtcag agtcttttag   180
ctagtggcaa ccaaaataac tacttggcct ggtaccaaca gaaaccagga aaagctccga   240
aaatgctgat tatttgggca tccactaggg tatctggagt cccttctcgc ttctctggat   300
ccgggtctgg gacggatttc actctgacca tcagcagtct gcagccggaa gacttcgcaa   360
cttattactg tcagcagtcc tacagccgcc cgtacacgtt cggacagggt accaaggtgg   420
agatcaaacg tacggtggct gcaccatctg tcttcatctt cccgccatct gatgagcagt   480
tgaaatctgg aactgcctct gttgtgtgcc tgctgaataa cttctatccc agagaggcca   540
aagtacagtg gaaggtggat aacgccctcc aatcgggtaa ctcccaggag agtgtcacag   600
agcaggacag caaggacagc acctacagcc tcagcagcac cctgacgctg agcaaagcag   660
actacgagaa acacaaagtc tacgcctgcg aagtcaccca tcagggcctg agctcgcccg   720
tcacaaagag cttcaacagg ggagagtgtt gactcgag                            758
```

<210> SEQ ID NO 70
<211> LENGTH: 240
<212> TYPE: PRT
<213> ORGANISM: Artificial Sequence
<220> FEATURE:
<223> OTHER INFORMATION: Synthetic (polypeptide consisting of light
chain of huAbF46-H4-A1 and human kappa constant region)

<400> SEQUENCE: 70

```
Met Asp Ser Gln Ala Gln Val Leu Met Leu Leu Leu Leu Ser Val Ser
1               5                   10                  15

Gly Thr Cys Gly Asp Ile Gln Met Thr Gln Ser Pro Ser Ser Leu Ser
            20                  25                  30

Ala Ser Val Gly Asp Arg Val Thr Ile Thr Cys Lys Ser Ser Gln Ser
        35                  40                  45

Leu Leu Ala Ser Gly Asn Gln Asn Asn Tyr Leu Ala Trp His Gln Gln
    50                  55                  60

Lys Pro Gly Lys Ala Pro Lys Met Leu Ile Ile Trp Ala Ser Thr Arg
65                  70                  75                  80

Val Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175
```

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 71
<211> LENGTH: 19
<212> TYPE: PRT
<213> ORGANISM: Artificial Sequence
<220> FEATURE:
<223> OTHER INFORMATION: Synthetic (epitope in SEMA domain of c-Met)

<400> SEQUENCE: 71

Phe Ser Pro Gln Ile Glu Glu Pro Ser Gln Cys Pro Asp Cys Val Val
1               5                   10                  15

Ser Ala Leu

<210> SEQ ID NO 72
<211> LENGTH: 10
<212> TYPE: PRT
<213> ORGANISM: Artificial Sequence
<220> FEATURE:
<223> OTHER INFORMATION: Synthetic (epitope in SEMA domain of c-Met)

<400> SEQUENCE: 72

Pro Gln Ile Glu Glu Pro Ser Gln Cys Pro
1               5                   10

<210> SEQ ID NO 73
<211> LENGTH: 5
<212> TYPE: PRT
<213> ORGANISM: Artificial Sequence
<220> FEATURE:
<223> OTHER INFORMATION: Synthetic (epitope in SEMA domain of c-Met)

<400> SEQUENCE: 73

Glu Glu Pro Ser Gln
1               5

<210> SEQ ID NO 74
<211> LENGTH: 117
<212> TYPE: PRT
<213> ORGANISM: Artificial Sequence
<220> FEATURE:
<223> OTHER INFORMATION: Synthetic (heavy chain variable region of
      anti-c-Met antibody (AbF46 or huAbF46-H1))

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 75
<211> LENGTH: 114
<212> TYPE: PRT
<213> ORGANISM: Artificial Sequence
<220> FEATURE:
<223> OTHER INFORMATION: Synthetic (light chain variable region of
      anti-c-Met antibody (AbF46 or huAbF46-H1))

<400> SEQUENCE: 75

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg

<210> SEQ ID NO 76
<211> LENGTH: 1416
<212> TYPE: DNA
<213> ORGANISM: Artificial Sequence
<220> FEATURE:
<223> OTHER INFORMATION: Synthetic (nucleotide sequence of heavy chain
      of anti-c-Met antibody (AbF46 or huAbF46-H1))
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop codon
<220> FEATURE:
<221> NAME/KEY: misc_feature
<222> LOCATION: (1411)..(1416)
<223> OTHER INFORMATION: XhoI restriction site

<400> SEQUENCE: 76

```
gaattcgccg ccaccatgga atggagctgg gttttctctg taacactttt aaatggtatc      60
cagtgtgagg tgaagctggt ggagtctgga ggaggcttgg tacagcctgg gggttctctg     120
agactctcct gtgcaacttc tgggttcacc ttcactgatt actacatgag ctgggtccgc     180
cagcctccag gaaaggcact gagtggttg gtttttatta gaaacaaagc taatggttac     240
acaacagagt acagtgcatc tgtgaagggt cggttcacca tctccagaga taattcccaa     300
agcatcctct atcttcaaat ggacaccctg agagctgagg acagtgccac ttattactgt     360
gcaagagata actggtttgc ttactggggc caagggactc tggtcactgt ctctgcagct     420
agcaccaagg gcccatcggt cttccccctg gcaccctcct ccaagagcac ctctggggc     480
acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagcccaaa     720
tcttgtgaca aaactcacac atgcccaccg tgcccagcac ctgaactcct ggggggaccg     780
tcagtcttcc tcttcccccc aaaacccaag gacaccctca tgatctcccg gacccctgag     840
gtcacatgcg tggtggtgga cgtgagccac gaagaccctg aggtcaagtt caactggtac     900
gtggacggcg tggaggtgca taatgccaag acaaagccgc gggaggagca gtacaacagc     960
acgtaccgtg tggtcagcgt cctcaccgtc ctgcaccagg actggctgaa tggcaaggag    1020
tacaagtgca aggtctccaa caaagccctc ccagccccca tcgagaaaac catctccaaa    1080
gccaaagggc agccccgaga accacaggtg tacaccctgc ccccatcccg ggaggagatg    1140
accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
aagagcctct ccctgtctcc gggtaaatga ctcgag                              1416
```

<210> SEQ ID NO 77
<211> LENGTH: 759
<212> TYPE: DNA
<213> ORGANISM: Artificial Sequence
<220> FEATURE:
<223> OTHER INFORMATION: Synthetic (nucleotide sequence of light chain
      of anti-c-Met antibody (AbF46 or huAbF46-H1))
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region

```
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)

<400> SEQUENCE: 77
gaattcacta gtgattaatt cgccgccacc atggattcac aggcccaggt cctcatgttg     60
ctgctgctat cggtatctgg tacctgtgga gacattttga tgacccagtc tccatcctcc    120
ctgactgtgt cagcaggaga aaggtcact atgagctgca agtccagtca gagtctttta    180
gctagtggca accaaaataa ctacttggcc tggcaccagc agaaaccagg acgatctcct    240
aaaatgctga taatttgggc atccactagg gtatctggag tccctgatcg cttcataggc    300
agtggatctg gacggattt cactctgacc atcaacagtg tgcaggctga agatctggct    360
gtttattact gtcagcagtc ctacagcgct ccgctcacgt tcggtgctgg gaccaagctg    420
gagctgaaac gtacggtggc tgcaccatct gtcttcatct tcccgccatc tgatgagcag    480
ttgaaatctg gaactgcctc tgttgtgtgc ctgctgaata acttctatcc cagagaggcc    540
aaagtacagt ggaaggtgga taacgccctc caatcgggta actcccagga gagtgtcaca    600
gagcaggaca gcaaggacag cacctacagc ctcagcagca ccctgacgct gagcaaagca    660
gactacgaga aacacaaagt ctacgcctgc gaagtcaccc atcagggcct gagctcgccc    720
gtcacaaaga gcttcaacag gggagagtgt tgactcgag                          759

<210> SEQ ID NO 78
<211> LENGTH: 4170
<212> TYPE: DNA
<213> ORGANISM: Artificial Sequence
<220> FEATURE:
<223> OTHER INFORMATION: Synthetic (polynucleotide encoding c-Met
      protein)

<400> SEQUENCE: 78
atgaaggccc ccgctgtgct tgcacctggc atcctcgtgc tcctgtttac cttggtgcag     60
aggagcaatg gggagtgtaa agaggcacta gcaaagtccg agatgaatgt gaatatgaag    120
tatcagcttc ccaacttcac cgcggaaaca cccatccaga atgtcattct acatgagcat    180
cacatttttcc ttggtgccac taactacatt tatgttttaa atgaggaaga ccttcagaag    240
gttgctgagt acaagactgg gcctgtgctg gaacacccag attgtttccc atgtcaggac    300
tgcagcagca aagccaattt atcaggaggt gtttggaaag ataacatcaa catggctcta    360
gttgtcgaca cctactatga tgatcaactc attagctgtg gcagcgtcaa cagagggacc    420
tgccagcgac atgtctttcc ccacaatcat actgctgaca tacagtcgga ggttcactgc    480
atattctccc cacagataga agagcccagc cagtgtcctg actgtgtggt gagcgccctg    540
ggagccaaag tcctttcatc tgtaaaggac cggttcatca acttctttgt aggcaatacc    600
ataaattctt cttatttccc agatcatcca ttgcattcga tatcagtgag aaggctaaag    660
gaaacgaaag atggttttat gttttttgacg gaccagtcct acattgatgt tttacctgag    720
ttcagagatt cttaccccat taagtatgtc catgcctttg aaagcaacaa ttttatttac    780
ttcttgacgg tccaaaggga aactctagat gctcagactt tcacacaag aataatcagg    840
ttctgttcca taaactctgg attgcattcc tacatggaaa tgcctctgga gtgtattctc    900
acagaaaaga gaaaaaagag atccacaaag aaggaagtgt ttaatatact tcaggctgcg    960
```

```
tatgtcagca agcctggggc ccagcttgct agacaaatag gagccagcct gaatgatgac    1020
attcttttcg gggtgttcgc acaaagcaag ccagattctg ccgaaccaat ggatcgatct    1080
gccatgtgtg cattccctat caaatatgtc aacgacttct tcaacaagat cgtcaacaaa    1140
aacaatgtga gatgtctcca gcattttac  ggacccaatc atgagcactg ctttaatagg    1200
acacttctga gaaattcatc aggctgtgaa gcgcgccgtg atgaatatcg aacagagttt    1260
accacagctt tgcagcgcgt tgacttattc atgggtcaat tcagcgaagt cctcttaaca    1320
tctatatcca ccttcattaa aggagacctc accatagcta atcttgggac atcagagggt    1380
cgcttcatgc aggttgtggt ttctcgatca ggaccatcaa cccctcatgt gaattttctc    1440
ctggactccc atccagtgtc tccagaagtg attgtggagc atacattaaa ccaaaatggc    1500
tacacactgg ttatcactgg gaagaagatc acgaagatcc cattgaatgg cttgggctgc    1560
agacatttcc agtcctgcag tcaatgcctc tctgccccac cctttgttca gtgtggctgg    1620
tgccacgaca aatgtgtgcg atcggaggaa tgcctgagcg ggacatggac tcaacagatc    1680
tgtctgcctg caatctacaa ggttttccca aatagtgcac cccttgaagg agggacaagg    1740
ctgaccatat gtggctggga ctttggattt cggaggaata taaatttga  tttaaagaaa    1800 actagagttc tccttggaaa tgagagctgc accttgactt taagtgagag cacgatgaat    1860
acattgaaat gcacagttgg tcctgccatg aataagcatt tcaatatgtc cataattatt    1920
tcaaatggcc acgggacaac acaatacagt acattctcct atgtggatcc tgtaataaca    1980
agtatttcgc cgaaatacgg tcctatggct ggtggcactt tacttacttt  aactggaaat    2040
tacctaaaca gtgggaattc tagacacatt tcaattggtg aaaaacatg  tacttttaaaa   2100 agtgtgtcaa acagtattct tgaatgttat accccagccc aaaccatttc aactgagttt    2160
gctgttaaat tgaaaattga cttagccaac cgagagacaa gcatcttcag ttaccgtgaa    2220
gatcccattg tctatgaaat tcatccaacc aaatctttta ttagtggtgg gagcacaata    2280
acaggtgttg ggaaaaacct gaattcagtt agtgtcccga gaatggtcat aaatgtgcat    2340
gaagcaggaa ggaactttac agtggcatgt caacatcgct ctaattcaga gataatctgt    2400
tgtaccactc cttccctgca acagctgaat ctgcaactcc ccctgaaaac caaagccttt    2460
ttcatgttag atgggatcct ttccaaatac tttgatctca tttatgtaca taatcctgtg    2520
tttaagcctt ttgaaaagcc agtgatgatc tcaatgggca atgaaaatgt actgaaaatt    2580
aagggaaatg atattgaccc tgaagcagtt aaaggtgaag tgttaaaagt tggaaataag    2640
agctgtgaga atatacactt acattctgaa gccgttttat gcacggtccc caatgacctg    2700
ctgaaattga acagcgagct aaatatagag tggaagcaag caatttcttc aaccgtcctt    2760
ggaaaagtaa tagttcaacc agatcagaat ttcacaggat tgattgctgg tgttgtctca    2820
atatcaacag cactgttatt actacttggg ttttcctgt  ggctgaaaaa gagaaagcaa    2880
attaaagatc tgggcagtga attagttcgc tacgatgcaa gagtacacac tcctcatttg    2940
gataggcttg taagtgcccg aagtgtaagc ccaactacag aaatggtttc aaatgaatct    3000
gtagactacc gagctacttt tccagaagat cagtttccta attcatctca gaacggttca    3060
tgccgacaag tgcagtatcc tctgacagac atgtcccca  tcctaactag tggggactct    3120
gatatatcca gtccattact gcaaaatact gtccacattg acctcagtgc tctaaatcca    3180
gagctggtcc aggcagtgca gcatgtagtg attgggccca gtagcctgat tgtgcatttc    3240
aatgaagtca taggaagagg gcatttggt  tgtgtatatc atgggacttt gttgacaat    3300 gatggcaaga aaattcactg tgctgtgaaa tccttgaaca gaatcactga cataggagaa    3360
```

```
gtttcccaat ttctgaccga gggaatcatc atgaaagatt ttagtcatcc caatgtcctc   3420
tcgctcctgg gaatctgcct gcgaagtgaa gggtctccgc tggtggtcct accatacatg   3480
aaacatggag atcttcgaaa tttcattcga aatgagactc ataatccaac tgtaaaagat   3540
cttattggct ttggtcttca agtagccaaa ggcatgaaat atcttgcaag caaaaagttt   3600
gtccacagag acttggctgc aagaaactgt atgctggatg aaaaattcac agtcaaggtt   3660
gctgattttg gtcttgccag agacatgtat gataaagaat actatagtgt acacaacaaa   3720
acaggtgcaa agctgccagt gaagtggatg gctttggaaa gtctgcaaac tcaaaagttt   3780
accaccaagt cagatgtgtg gtcctttggc gtgctcctct gggagctgat gacaagagga   3840
gccccacctt atcctgacgt aaacaccttt gatataactg tttacttgtt gcaagggaga   3900
agactcctac aacccgaata ctgcccagac cccttatatg aagtaatgct aaaatgctgg   3960 cacccctaaag ccgaaatgcg cccatccttt tctgaactgg tgtcccggat atcagcgatc   4020
ttctctactt tcattgggga gcactatgtc catgtgaacg ctacttatgt gaacgtaaaa   4080
tgtgtcgctc cgtatccttc tctgttgtca tcagaagata cgctgatga tgaggtggac   4140 acacgaccag cctccttctg ggagacatca                                    4170

<210> SEQ ID NO 79
<211> LENGTH: 444
<212> TYPE: PRT
<213> ORGANISM: Artificial Sequence
<220> FEATURE:
<223> OTHER INFORMATION: Synthetic (SEMA domain of c-Met)

<400> SEQUENCE: 79

Leu His Glu His His Ile Phe Leu Gly Ala Thr Asn Tyr Ile Tyr Val
1               5                   10                  15

Leu Asn Glu Glu Asp Leu Gln Lys Val Ala Glu Tyr Lys Thr Gly Pro
                20                  25                  30

Val Leu Glu His Pro Asp Cys Phe Pro Cys Gln Asp Cys Ser Ser Lys
            35                  40                  45

Ala Asn Leu Ser Gly Gly Val Trp Lys Asp Asn Ile Asn Met Ala Leu
        50                  55                  60

Val Val Asp Thr Tyr Tyr Asp Asp Gln Leu Ile Ser Cys Gly Ser Val
65                  70                  75                  80

Asn Arg Gly Thr Cys Gln Arg His Val Phe Pro His Asn His Thr Ala
                85                  90                  95

Asp Ile Gln Ser Glu Val His Cys Ile Phe Ser Pro Gln Ile Glu Glu
            100                 105                 110

Pro Ser Gln Cys Pro Asp Cys Val Val Ser Ala Leu Gly Ala Lys Val
        115                 120                 125

Leu Ser Ser Val Lys Asp Arg Phe Ile Asn Phe Phe Val Gly Asn Thr
    130                 135                 140

Ile Asn Ser Ser Tyr Phe Pro Asp His Pro Leu His Ser Ile Ser Val
145                 150                 155                 160

Arg Arg Leu Lys Glu Thr Lys Asp Gly Phe Met Phe Leu Thr Asp Gln
                165                 170                 175

Ser Tyr Ile Asp Val Leu Pro Glu Phe Arg Asp Ser Tyr Pro Ile Lys
            180                 185                 190

Tyr Val His Ala Phe Glu Ser Asn Asn Phe Ile Tyr Phe Leu Thr Val
        195                 200                 205

Gln Arg Glu Thr Leu Asp Ala Gln Thr Phe His Thr Arg Ile Ile Arg
```

```
                210                 215                 220
Phe Cys Ser Ile Asn Ser Gly Leu His Ser Tyr Met Glu Met Pro Leu
225                 230                 235                 240

Glu Cys Ile Leu Thr Glu Lys Arg Lys Lys Arg Ser Thr Lys Lys Glu
                245                 250                 255

Val Phe Asn Ile Leu Gln Ala Ala Tyr Val Ser Lys Pro Gly Ala Gln
                260                 265                 270

Leu Ala Arg Gln Ile Gly Ala Ser Leu Asn Asp Asp Ile Leu Phe Gly
            275                 280                 285

Val Phe Ala Gln Ser Lys Pro Asp Ser Ala Glu Pro Met Asp Arg Ser
290                 295                 300

Ala Met Cys Ala Phe Pro Ile Lys Tyr Val Asn Asp Phe Phe Asn Lys
305                 310                 315                 320

Ile Val Asn Lys Asn Asn Val Arg Cys Leu Gln His Phe Tyr Gly Pro
                325                 330                 335

Asn His Glu His Cys Phe Asn Arg Thr Leu Leu Arg Asn Ser Ser Gly
            340                 345                 350

Cys Glu Ala Arg Arg Asp Glu Tyr Arg Thr Glu Phe Thr Thr Ala Leu
            355                 360                 365

Gln Arg Val Asp Leu Phe Met Gly Gln Phe Ser Glu Val Leu Leu Thr
            370                 375                 380

Ser Ile Ser Thr Phe Ile Lys Gly Asp Leu Thr Ile Ala Asn Leu Gly
385                 390                 395                 400

Thr Ser Glu Gly Arg Phe Met Gln Val Val Ser Arg Ser Gly Pro
                405                 410                 415

Ser Thr Pro His Val Asn Phe Leu Leu Asp Ser His Pro Val Ser Pro
                420                 425                 430

Glu Val Ile Val Glu His Thr Leu Asn Gln Asn Gly
            435                 440

<210> SEQ ID NO 80
<211> LENGTH: 451
<212> TYPE: PRT
<213> ORGANISM: Artificial Sequence
<220> FEATURE:
<223> OTHER INFORMATION: Synthetic (PSI-IPT domain of c-Met)

<400> SEQUENCE: 80

Tyr Thr Leu Val Ile Thr Gly Lys Lys Ile Thr Lys Ile Pro Leu Asn
1               5                   10                  15

Gly Leu Gly Cys Arg His Phe Gln Ser Cys Ser Gln Cys Leu Ser Ala
            20                  25                  30

Pro Pro Phe Val Gln Cys Gly Trp Cys His Asp Lys Cys Val Arg Ser
        35                  40                  45

Glu Glu Cys Leu Ser Gly Thr Trp Thr Gln Gln Ile Cys Leu Pro Ala
50                  55                  60

Ile Tyr Lys Val Phe Pro Asn Ser Ala Pro Leu Glu Gly Gly Thr Arg
65                  70                  75                  80

Leu Thr Ile Cys Gly Trp Asp Phe Gly Phe Arg Arg Asn Asn Lys Phe
                85                  90                  95

Asp Leu Lys Lys Thr Arg Val Leu Leu Gly Asn Glu Ser Cys Thr Leu
            100                 105                 110

Thr Leu Ser Glu Ser Thr Met Asn Thr Leu Lys Cys Thr Val Gly Pro
        115                 120                 125

Ala Met Asn Lys His Phe Asn Met Ser Ile Ile Ile Ser Asn Gly His
```

```
                    130                 135                 140
Gly Thr Thr Gln Tyr Ser Thr Phe Ser Tyr Val Asp Pro Val Ile Thr
145                 150                 155                 160

Ser Ile Ser Pro Lys Tyr Gly Pro Met Ala Gly Thr Leu Leu Thr
                165                 170                 175

Leu Thr Gly Asn Tyr Leu Asn Ser Gly Asn Ser Arg His Ile Ser Ile
                180                 185                 190

Gly Gly Lys Thr Cys Thr Leu Lys Ser Val Ser Asn Ser Ile Leu Glu
            195                 200                 205

Cys Tyr Thr Pro Ala Gln Thr Ile Ser Thr Glu Phe Ala Val Lys Leu
            210                 215                 220

Lys Ile Asp Leu Ala Asn Arg Glu Thr Ser Ile Phe Ser Tyr Arg Glu
225                 230                 235                 240

Asp Pro Ile Val Tyr Glu Ile His Pro Thr Lys Ser Phe Ile Ser Thr
                245                 250                 255

Trp Trp Lys Glu Pro Leu Asn Ile Val Ser Phe Leu Phe Cys Phe Ala
                260                 265                 270

Ser Gly Gly Ser Thr Ile Thr Gly Val Gly Lys Asn Leu Asn Ser Val
            275                 280                 285

Ser Val Pro Arg Met Val Ile Asn Val His Glu Ala Gly Arg Asn Phe
            290                 295                 300

Thr Val Ala Cys Gln His Arg Ser Asn Ser Glu Ile Ile Cys Cys Thr
305                 310                 315                 320

Thr Pro Ser Leu Gln Gln Leu Asn Leu Gln Leu Pro Leu Lys Thr Lys
                325                 330                 335

Ala Phe Phe Met Leu Asp Gly Ile Leu Ser Lys Tyr Phe Asp Leu Ile
                340                 345                 350

Tyr Val His Asn Pro Val Phe Lys Pro Phe Glu Lys Pro Val Met Ile
            355                 360                 365

Ser Met Gly Asn Glu Asn Val Leu Glu Ile Lys Gly Asn Asp Ile Asp
370                 375                 380

Pro Glu Ala Val Lys Gly Glu Val Leu Lys Val Gly Asn Lys Ser Cys
385                 390                 395                 400

Glu Asn Ile His Leu His Ser Glu Ala Val Leu Cys Thr Val Pro Asn
                405                 410                 415

Asp Leu Leu Lys Leu Asn Ser Glu Leu Asn Ile Glu Trp Lys Gln Ala
                420                 425                 430

Ile Ser Ser Thr Val Leu Gly Lys Val Ile Val Gln Pro Asp Gln Asn
            435                 440                 445

Phe Thr Gly
    450

<210> SEQ ID NO 81
<211> LENGTH: 313
<212> TYPE: PRT
<213> ORGANISM: Artificial Sequence
<220> FEATURE:
<223> OTHER INFORMATION: Synthetic (TyrKc domain of c-Met)

<400> SEQUENCE: 81

Val His Phe Asn Glu Val Ile Gly Arg Gly His Phe Gly Cys Val Tyr
1               5                   10                  15

His Gly Thr Leu Leu Asp Asn Asp Gly Lys Lys Ile His Cys Ala Val
            20                  25                  30

Lys Ser Leu Asn Arg Ile Thr Asp Ile Gly Glu Val Ser Gln Phe Leu
```

```
                 35                  40                  45
Thr Glu Gly Ile Ile Met Lys Asp Phe Ser His Pro Asn Val Leu Ser
 50                  55                  60

Leu Leu Gly Ile Cys Leu Arg Ser Glu Gly Ser Pro Leu Val Val Leu
 65                  70                  75                  80

Pro Tyr Met Lys His Gly Asp Leu Arg Asn Phe Ile Arg Asn Glu Thr
                 85                  90                  95

His Asn Pro Thr Val Lys Asp Leu Ile Gly Phe Gly Leu Gln Val Ala
            100                 105                 110

Lys Gly Met Lys Tyr Leu Ala Ser Lys Lys Phe Val His Arg Asp Leu
        115                 120                 125

Ala Ala Arg Asn Cys Met Leu Asp Glu Lys Phe Thr Val Lys Val Ala
130                 135                 140

Asp Phe Gly Leu Ala Arg Asp Met Tyr Asp Lys Glu Tyr Tyr Ser Val
145                 150                 155                 160

His Asn Lys Thr Gly Ala Lys Leu Pro Val Lys Trp Met Ala Leu Glu
                165                 170                 175

Ser Leu Gln Thr Gln Lys Phe Thr Thr Lys Ser Asp Val Trp Ser Phe
            180                 185                 190

Gly Val Leu Leu Trp Glu Leu Met Thr Arg Gly Ala Pro Pro Tyr Pro
        195                 200                 205

Asp Val Asn Thr Phe Asp Ile Thr Val Tyr Leu Leu Gln Gly Arg Arg
210                 215                 220

Leu Leu Gln Pro Glu Tyr Cys Pro Asp Pro Leu Tyr Glu Val Met Leu
225                 230                 235                 240

Lys Cys Trp His Pro Lys Ala Glu Met Arg Pro Ser Phe Ser Glu Leu
                245                 250                 255

Val Ser Arg Ile Ser Ala Ile Phe Ser Thr Phe Ile Gly Glu His Tyr
            260                 265                 270

Val His Val Asn Ala Thr Tyr Val Asn Val Lys Cys Val Ala Pro Tyr
        275                 280                 285

Pro Ser Leu Leu Ser Ser Glu Asp Asn Ala Asp Asp Glu Val Asp Thr
290                 295                 300

Arg Pro Ala Ser Phe Trp Glu Thr Ser
305                 310

<210> SEQ ID NO 82
<211> LENGTH: 1332
<212> TYPE: DNA
<213> ORGANISM: Artificial Sequence
<220> FEATURE:
<223> OTHER INFORMATION: Synthetic (polynucleotide encoding SEMA domain
      of c-Met)

<400> SEQUENCE: 82
ctacatgagc atcacatttt ccttggtgcc actaactaca tttatgtttt aaatgaggaa      60
gaccttcaga aggttgctga gtacaagact gggcctgtgc tggaacaccc agattgtttc     120
ccatgtcagg actgcagcag caaagccaat ttatcaggag gtgtttggaa agataacatc     180
aacatggctc tagttgtcga cacctactat gatgatcaac tcattagctg tggcagcgtc     240
aacagaggga cctgccagcg acatgtcttt ccccacaatc atactgctga catacagtcg     300
gaggttcact gcatattctc cccacagata gaagagccca gccagtgtcc tgactgtgtg     360
gtgagcgccc tggagccaag tcctttca tctgtaaagg accggttcat caacttcttt     420
gtaggcaata ccataaaatc ttcttatttc ccagatcatc cattgcattc gatatcagtg     480
```

```
agaaggctaa aggaaacgaa agatggtttt atgtttttga cggaccagtc ctacattgat      540
gttttacctg agttcagaga ttcttacccc attaagtatg tccatgcctt tgaaagcaac      600
aattttattt acttcttgac ggtccaaagg gaaactctag atgctcagac ttttcacaca      660
agaataatca ggttctgttc cataaactct ggattgcatt cctacatgga aatgcctctg      720
gagtgtattc tcacagaaaa gagaaaaaag agatccacaa agaaggaagt gtttaatata      780
cttcaggctg cgtatgtcag caagcctggg gcccagcttg ctagacaaat aggagccagc      840
ctgaatgatg acattctttt cggggtgttc gcacaaagca agccagattc tgccgaacca      900
atggatcgat ctgccatgtg tgcattccct atcaaatatg tcaacgactt cttcaacaag      960
atcgtcaaca aaaacaatgt gagatgtctc cagcattttt acggacccaa tcatgagcac     1020
tgctttaata ggacacttct gagaaattca tcaggctgtg aagcgcgccg tgatgaatat     1080
cgaacagagt ttaccacagc tttgcagcgc gttgactt at tcatgggtca attcagcgaa     1140
gtcctcttaa catctatatc caccttcatt aaaggagacc tcaccatagc taatcttggg     1200
acatcagagg gtcgcttcat gcaggttgtg gtttctcgat caggaccatc aacccctcat     1260
gtgaattttc tcctggactc ccatccagtg tctccagaag tgattgtgga gcatacatta     1320
aaccaaaatg gc                                                         1332

<210> SEQ ID NO 83
<211> LENGTH: 1299
<212> TYPE: DNA
<213> ORGANISM: Artificial Sequence
<220> FEATURE:
<223> OTHER INFORMATION: Synthetic (polynucleotide encoding PSI-IPT
      domain of c-Met)

<400> SEQUENCE: 83
tacacactgg ttatcactgg gaagaagatc acgaagatcc cattgaatgg cttgggctgc       60
agacatttcc agtcctgcag tcaatgcctc tctgccccac cctttgttca gtgtggctgg      120
tgccacgaca aatgtgtgcg atcggaggaa tgcctgagcg ggacatggac tcaacagatc      180
tgtctgcctg caatctacaa ggttttccca aatagtgcac cccttgaagg agggacaagg      240
ctgaccatat gtggctggga ctttggattt cggaggaata taaatttga tttaaagaaa      300 actagagttc tccttggaaa tgagagctgc accttgactt aagtgagag cacgatgaat      360 acattgaaat gcacagttgg tcctgccatg aataagcatt tcaatatgtc cataattatt      420
tcaaatggcc acgggacaac acaatacagt acattctcct atgtggatcc tgtaataaca      480
agtatttcgc cgaaatacgg tcctatggct ggtggcactt tacttacttt aactggaaat      540
tacctaaaca gtgggaattc tagacacatt tcaattggtg aaaaacatg tactttaaaa      600 agtgtgtcaa acagtattct tgaatgttat accccagccc aaaccatttc aactgagttt      660
gctgttaaat tgaaaattga cttagccaac cgagagacaa gcatcttcag ttaccgtgaa      720
gatcccattg tctatgaaat tcatccaacc aaatctttta ttagtggtgg agcacaata      780 acaggtgttg ggaaaaacct gaattcagtt agtgtcccga aatggtcat aaatgtgcat      840 gaagcaggaa ggaactttac agtggcatgt caacatcgct ctaattcaga gataatctgt     900
tgtaccactc cttccctgca acagctgaat ctgcaactcc cctgaaaac caaagccttt      960 ttcatgttag atgggatcct ttccaaatac tttgatctca tttatgtaca taatcctgtg     1020
tttaagcctt tgaaaagcc agtgatgatc tcaatgggca atgaaaatgt actgaaatt     1080 aagggaaatg atattgaccc tgaagcagtt aaaggtgaag tgttaaaagt tggaaataag     1140
```

-continued

```
agctgtgaga atatacactt acattctgaa gccgttttat gcacggtccc caatgacctg    1200
ctgaaattga acagcgagct aaatatagag tggaagcaag caatttcttc aaccgtcctt    1260
ggaaaagtaa tagttcaacc agatcagaat ttcacagga                           1299
```

<210> SEQ ID NO 84
<211> LENGTH: 939
<212> TYPE: DNA
<213> ORGANISM: Artificial Sequence
<220> FEATURE:
<223> OTHER INFORMATION: Synthetic (polynucleotide encoding TyrKc domain of c-Met)

<400> SEQUENCE: 84

```
gtgcatttca atgaagtcat aggaagaggg cattttggtt gtgtatatca tgggactttg      60
ttggacaatg atggcaagaa aattcactgt gctgtgaaat ccttgaacag aatcactgac     120
ataggagaag tttcccaatt tctgaccgag ggaatcatca tgaaagattt tagtcatccc     180
aatgtcctct cgctcctggg aatctgcctg cgaagtgaag ggtctccgct ggtggtccta     240
ccatacatga acatggaga tcttcgaaat tcattcgaa atgagactca taatccaact      300
gtaaaagatc ttattggctt tggtcttcaa gtagccaaag catgaaaata tcttgcaagc     360
aaaaagtttg tccacagaga cttggctgca agaaactgta tgctggatga aaaattcaca     420
gtcaaggttg ctgattttgg tcttgccaga gacatgtatg ataaagaata ctatagtgta     480
cacaacaaaa caggtgcaaa gctgccagtg aagtggatgg ctttggaaag tctgcaaact     540
caaaagttta ccaccaagtc agatgtgtgg tcctttggcg tgctcctctg ggagctgatg     600
acaagaggag ccccacctta tcctgacgta aacacctttg atataactgt ttacttgttg     660
caagggagaa gactcctaca acccgaatac tgcccagacc ccttatatga agtaatgcta     720
aaatgctggc accctaaagc cgaaatgcgc ccatcctttt ctgaactggt gtcccggata     780
tcagcgatct tctctacttt cattggggag cactatgtcc atgtgaacgc tacttatgtg     840
aacgtaaaat gtgtcgctcc gtatccttct ctgttgtcat cagaagataa cgctgatgat     900
gaggtggaca cacgaccagc ctccttctgg gagacatca                            939
```

<210> SEQ ID NO 85
<211> LENGTH: 13
<212> TYPE: PRT
<213> ORGANISM: Artificial Sequence
<220> FEATURE:
<223> OTHER INFORMATION: Synthetic (heavy chain CDR3 of anti-c-Met antibody)

<400> SEQUENCE: 85

```
Asp Asn Trp Phe Ala Tyr Trp Gly Gln Gly Thr Leu Val
1               5                   10
```

<210> SEQ ID NO 86
<211> LENGTH: 10
<212> TYPE: PRT
<213> ORGANISM: Artificial Sequence
<220> FEATURE:
<223> OTHER INFORMATION: Synthetic (light chain CDR3 of anti-c-Met antibody)

<400> SEQUENCE: 86

```
Leu Thr Phe Gly Ala Gly Thr Lys Leu Glu
1               5                   10
```

```
<210> SEQ ID NO 87
<211> LENGTH: 117
<212> TYPE: PRT
<213> ORGANISM: Artificial Sequence
<220> FEATURE:
<223> OTHER INFORMATION: Synthetic (heavy chain variable region of
      monoclonal antibody AbF46)

<400> SEQUENCE: 87

Glu Val Lys Leu Val Glu Ser Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asp Thr Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ala
        115

<210> SEQ ID NO 88
<211> LENGTH: 114
<212> TYPE: PRT
<213> ORGANISM: Artificial Sequence
<220> FEATURE:
<223> OTHER INFORMATION: Synthetic (light chain variable region of
      anti-c-Met antibody)

<400> SEQUENCE: 88

Asp Ile Leu Met Thr Gln Ser Pro Ser Ser Leu Thr Val Ser Ala Gly
1               5                   10                  15

Glu Lys Val Thr Met Ser Cys Lys Ser Ser Gln Ser Leu Leu Ala Ser
            20                  25                  30

Gly Asn Gln Asn Asn Tyr Leu Ala Trp His Gln Gln Lys Pro Gly Arg
        35                  40                  45

Ser Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Asn Ser Val Gln Ala Glu Asp Leu Ala Val Tyr Tyr Cys Gln Gln
                85                  90                  95

Ser Tyr Ser Ala Pro Leu Thr Phe Gly Ala Gly Thr Lys Leu Glu Leu
            100                 105                 110

Lys Arg

<210> SEQ ID NO 89
<211> LENGTH: 17
<212> TYPE: PRT
<213> ORGANISM: Artificial Sequence
<220> FEATURE:
<223> OTHER INFORMATION: Synthetic (light chain CDR3 of anti-c-Met
      antibody)

<400> SEQUENCE: 89
```

Gln Gln Ser Tyr Ser Ala Pro Leu Thr Phe Gly Ala Gly Thr Lys Leu
1               5                   10                  15

Glu

<210> SEQ ID NO 90
<211> LENGTH: 117
<212> TYPE: PRT
<213> ORGANISM: Artificial Sequence
<220> FEATURE:
<223> OTHER INFORMATION: Synthetic (heavy chain variable region of
      AT-VH1)

<400> SEQUENCE: 90

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 91
<211> LENGTH: 117
<212> TYPE: PRT
<213> ORGANISM: Artificial Sequence
<220> FEATURE:
<223> OTHER INFORMATION: Synthetic (heavy chain variable region of
      AT-VH2)

<400> SEQUENCE: 91

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 92
<211> LENGTH: 117
<212> TYPE: PRT

<213> ORGANISM: Artificial Sequence
<220> FEATURE:
<223> OTHER INFORMATION: Synthetic (heavy chain variable region of AT-VH3)

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Thr Tyr
            85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 93
<211> LENGTH: 117
<212> TYPE: PRT
<213> ORGANISM: Artificial Sequence
<220> FEATURE:
<223> OTHER INFORMATION: Synthetic (heavy chain variable region of AT-VH4)

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Thr Tyr
            85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 94
<211> LENGTH: 117
<212> TYPE: PRT
<213> ORGANISM: Artificial Sequence
<220> FEATURE:
<223> OTHER INFORMATION: Synthetic (heavy chain variable region of AT-VH5)

<400> SEQUENCE: 94

Glu Val Gln Leu Val Glu Ser Gly Gly Gly Leu Val Gln Pro Gly Gly
1               5                   10                  15

```
Ser Leu Arg Leu Ser Cys Ala Thr Ser Gly Phe Thr Phe Thr Asp Tyr
         20                  25                  30

Tyr Met Ser Trp Val Arg Gln Pro Gly Lys Gly Leu Glu Trp Leu
         35                  40                  45

Gly Phe Ile Arg Asn Lys Ala Asn Gly Tyr Thr Thr Glu Tyr Ser Ala
 50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Asp Asn Trp Phe Ala Tyr Trp Gly Gln Gly Thr Leu
                100                 105                 110

Val Thr Val Ser Ser
        115

<210> SEQ ID NO 95
<211> LENGTH: 114
<212> TYPE: PRT
<213> ORGANISM: Artificial Sequence
<220> FEATURE:
<223> OTHER INFORMATION: Synthetic (light chain variable region of anti
      c-Met humanized antibody(huAbF46-H4))

<400> SEQUENCE: 95

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
         20                  25                  30

Gly Asn Gln Asn Asn Tyr Leu Ala Trp His Gln Gln Lys Pro Gly Lys
         35                  40                  45

Ala Pro Lys Met Leu Ile Ile Trp Ala Ser Thr Arg Val Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Ala Pro Leu Thr Phe Gly Gln Gly Thr Lys Val Glu Ile
                100                 105                 110

Lys Arg

<210> SEQ ID NO 96
<211> LENGTH: 113
<212> TYPE: PRT
<213> ORGANISM: Artificial Sequence
<220> FEATURE:
<223> OTHER INFORMATION: Synthetic (light chain variable region of
      AT-Vk1)

<400> SEQUENCE: 96

Asp Ile Leu Met Thr Gln Ser Pro Ser Ser Leu Thr Ala Ser Val Gly
 1               5                  10                  15

Asp Arg Val Thr Met Thr Cys Lys Ser Ser Gln Ser Leu Leu Ala Ser
         20                  25                  30

Gly Asn Gln Asn Asn Tyr Leu Ala Trp His Gln Gln Lys Pro Gly Lys
         35                  40                  45

Ala Pro Lys Met Leu Ile Ile Trp Ala Ser Thr Arg Val Ser Gly Val
 50                  55                  60
```

```
Pro Asp Arg Phe Ile Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Ser Tyr Ser Ala Pro Leu Thr Phe Gly Gln Gly Thr Lys Leu Glu Ile
                100                 105                 110

Lys
```

<210> SEQ ID NO 97
<211> LENGTH: 113
<212> TYPE: PRT
<213> ORGANISM: Artificial Sequence
<220> FEATURE:
<223> OTHER INFORMATION: Synthetic (light chain variable region of AT-Vk2)

<400> SEQUENCE: 97

```
Asp Ile Leu Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
                 20                  25                  30

Gly Asn Gln Asn Asn Tyr Leu Ala Trp His Gln Lys Pro Gly Lys
             35                  40                  45

Ala Pro Lys Met Leu Ile Ile Trp Ala Ser Thr Arg Val Ser Gly Val
         50                  55                  60

Pro Asp Arg Phe Ile Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Ser Tyr Ser Ala Pro Leu Thr Phe Gly Gln Gly Thr Lys Leu Glu Ile
                100                 105                 110

Lys
```

<210> SEQ ID NO 98
<211> LENGTH: 113
<212> TYPE: PRT
<213> ORGANISM: Artificial Sequence
<220> FEATURE:
<223> OTHER INFORMATION: Synthetic (light chain variable region of AT-Vk3)

<400> SEQUENCE: 98

```
Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
                 20                  25                  30

Gly Asn Gln Asn Asn Tyr Leu Ala Trp His Gln Lys Pro Gly Lys
             35                  40                  45

Ala Pro Lys Met Leu Ile Ile Trp Ala Ser Thr Arg Val Ser Gly Val
         50                  55                  60

Pro Asp Arg Phe Ile Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Ser Tyr Ser Ala Pro Leu Thr Phe Gly Gln Gly Thr Lys Leu Glu Ile
                100                 105                 110

Lys
```

```
<210> SEQ ID NO 99
<211> LENGTH: 113
<212> TYPE: PRT
<213> ORGANISM: Artificial Sequence
<220> FEATURE:
<223> OTHER INFORMATION: Synthetic (light chain variable region of
      AT-Vk4)

<400> SEQUENCE: 99

Asp Ile Gln Met Thr Gln Ser Pro Ser Leu Ser Ala Ser Val Gly
1               5                   10                  15

Asp Arg Val Thr Ile Thr Cys Lys Ser Gln Ser Leu Leu Ala Ser
                20                  25                  30

Gly Asn Gln Asn Tyr Leu Ala Trp His Gln Lys Pro Gly Lys
                35                  40                  45

Ala Pro Lys Met Leu Ile Ile Trp Ala Ser Thr Arg Val Ser Gly Val
        50                  55                  60

Pro Asp Arg Phe Ser Gly Ser Gly Ser Gly Thr Asp Phe Thr Leu Thr
65              70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
                100                 105                 110

Lys

<210> SEQ ID NO 100
<211> LENGTH: 13
<212> TYPE: PRT
<213> ORGANISM: Artificial Sequence
<220> FEATURE:
<223> OTHER INFORMATION: Synthetic (modified hinge region(U7-HC6))

<400> SEQUENCE: 100

Glu Pro Ser Cys Asp Lys His Cys Cys Pro Pro Cys Pro
1               5                   10

<210> SEQ ID NO 101
<211> LENGTH: 13
<212> TYPE: PRT
<213> ORGANISM: Artificial Sequence
<220> FEATURE:
<223> OTHER INFORMATION: Synthetic (modified hinge region(U6-HC7))

<400> SEQUENCE: 101

Glu Pro Lys Ser Cys Asp Cys His Cys Pro Pro Cys Pro
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Synthetic (modified hinge region(U3-HC9))

<400> SEQUENCE: 102

Glu Arg Lys Cys Cys Val Glu Cys Pro Pro Cys Pro
1               5                   10

<210> SEQ ID NO 103
<211> LENGTH: 14
<212> TYPE: PRT
<213> ORGANISM: Artificial Sequence
<220> FEATURE:
<223> OTHER INFORMATION: Synthetic (modified hinge region(U6-HC8))
```

<400> SEQUENCE: 103

Glu Pro Arg Asp Cys Gly Cys Lys Pro Cys Pro Pro Cys Pro
1               5                   10

<210> SEQ ID NO 104
<211> LENGTH: 13
<212> TYPE: PRT
<213> ORGANISM: Artificial Sequence
<220> FEATURE:
<223> OTHER INFORMATION: Synthetic (modified hinge region(U8-HC5))

<400> SEQUENCE: 104

Glu Lys Cys Asp Lys Thr His Thr Cys Pro Pro Cys Pro
1               5                   10

<210> SEQ ID NO 105
<211> LENGTH: 15
<212> TYPE: PRT
<213> ORGANISM: Artificial Sequence
<220> FEATURE:
<223> OTHER INFORMATION: Synthetic (human hinge region)

<400> SEQUENCE: 105

Glu Pro Lys Ser Cys Asp Lys Thr His Thr Cys Pro Pro Cys Pro
1               5                   10                  15

<210> SEQ ID NO 106
<211> LENGTH: 17
<212> TYPE: PRT
<213> ORGANISM: Artificial Sequence
<220> FEATURE:
<223> OTHER INFORMATION: Synthetic (CDR-L1 of antibody L3-11Y)

<400> SEQUENCE: 106

Lys Ser Ser Gln Ser Leu Leu Ala Trp Gly Asn Gln Asn Asn Tyr Leu
1               5                   10                  15

Ala

<210> SEQ ID NO 107
<211> LENGTH: 114
<212> TYPE: PRT
<213> ORGANISM: Artificial Sequence
<220> FEATURE:
<223> OTHER INFORMATION: Synthetic (amino acid sequence of light chain
      variable region of antibody L3-11Y)

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Trp
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg

```
<210> SEQ ID NO 108
<211> LENGTH: 220
<212> TYPE: PRT
<213> ORGANISM: Artificial Sequence
<220> FEATURE:
<223> OTHER INFORMATION: Synthetic (amino acid sequence of light chain
      of antibody L3-11Y)

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Trp
            20                  25                  30

Gly Asn Gln Asn Asn Tyr Leu Ala Trp Tyr Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65              70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130             135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```